United States Patent
Phan et al.

(10) Patent No.: US 9,844,571 B2
(45) Date of Patent: Dec. 19, 2017

(54) ISOLATION, CULTIVATION AND USES OF STEM/PROGENITOR CELLS

(71) Applicant: CELLRESEARCH CORPORATION PTE LTD, Singapore (SG)

(72) Inventors: Toan-Thang Phan, Singapore (SG); Ivor Jiun Lim, Singapore (SG)

(73) Assignee: CELLRESEARCH CORPORATION PTE LTD, Singapore (SG)

( * ) Notice: Subject to any disclaimer, the term of this patent is extended or adjusted under 35 U.S.C. 154(b) by 0 days.

(21) Appl. No.: 14/953,266

(22) Filed: Nov. 27, 2015

(65) Prior Publication Data

US 2016/0250257 A1 Sep. 1, 2016

Related U.S. Application Data

(62) Division of application No. 11/205,248, filed on Aug. 15, 2005.

(60) Provisional application No. 60/602,208, filed on Aug. 16, 2004, provisional application No. 60/632,209, filed on Dec. 1, 2004.

(51) Int. Cl.
| | | |
|---|---|---|
| *A61K 35/28* | (2015.01) | |
| *A61K 35/36* | (2015.01) | |
| *A61K 35/51* | (2015.01) | |
| *A61K 9/06* | (2006.01) | |
| *A61K 9/00* | (2006.01) | |
| *C12N 5/071* | (2010.01) | |
| *C12N 5/073* | (2010.01) | |
| *C12N 5/0735* | (2010.01) | |
| *C12N 5/0775* | (2010.01) | |

(52) U.S. Cl.
CPC ............ *A61K 35/28* (2013.01); *A61K 9/0014* (2013.01); *A61K 9/06* (2013.01); *A61K 35/36* (2013.01); *A61K 35/51* (2013.01); *C12N 5/063* (2013.01); *C12N 5/0603* (2013.01); *C12N 5/0605* (2013.01); *C12N 5/0606* (2013.01); *C12N 5/0629* (2013.01); *C12N 5/0668* (2013.01); *C12N 2506/025* (2013.01); *C12N 2506/1392* (2013.01)

(58) Field of Classification Search
CPC ........ A61K 35/28; A61K 35/51; A61K 35/36; A61K 9/06; A61K 9/0014; C12N 5/0603; C12N 5/0606; C12N 5/0629; C12N 5/0668; C12N 5/063; C12N 5/0605; C12N 2506/1392; C12N 2506/025
See application file for complete search history.

(56) References Cited

U.S. PATENT DOCUMENTS

2003/0096409 A1  5/2003  Yasumoto et al.

OTHER PUBLICATIONS

The Office Action issued by the USPTO in U.S. Appl. No. 14/715,441 dated May 26, 2016.
Beer et al. "Expression and function of keratinocyte growth factor and activin in skin morphogenesis and cutaneous wound repair", J Investig Dermatol Symp Proc. Dec. 2000;5(1):34-9.
Froget et al., "Wound healing mediator production by human dermal fibroblasts grown within a collagen-GAG matrix for skin repair in humans", Eur Cytokine Netw. Jan.-Mar. 2003;14(1):60-4.
Lin et al., "Essential involvement of IL-6 in the skin wound-healing process as evidenced by delayed wound healing in IL-6-deficient mice", J Leukoc Biol. Jun. 2003;73(6):713-21.
Low et al., "Wound healing in MIP-1alpha(-/-) and MCP-1(-/-) mice", Am J Pathol. Aug. 2001;159(2):457-63.
Rennekampff et al., "Role of melanoma growth stimulatory activity (MGSA/gro) on keratinocyte function in wound healing", Arch Dermatol Res. Mar. 1997;289(4):204-12.
Schultz et al., "EGF and TGF-alpha in wound healing and repair", J Cell Biochem. Apr. 1991;45(4):346-52.
Yoshida et al., "Neutralization of hepatocyte growth factor leads to retarded cutaneous wound healing associated with decreased neovascularization and granulation tissue formation", J Invest Dermatol. Feb. 2003;120(2):335-43.

*Primary Examiner* — Taeyoon Kim
(74) *Attorney, Agent, or Firm* — Acuity Law Group, PC; Michael A. Whittaker

(57) ABSTRACT

The present invention relates to a method of treating a subject having a disorder comprising administering to the subject an effective amount of a stem/progenitor cell isolated from the amniotic membrane of the umbilical cord or an effective amount of a cellular extract thereof.

6 Claims, 67 Drawing Sheets

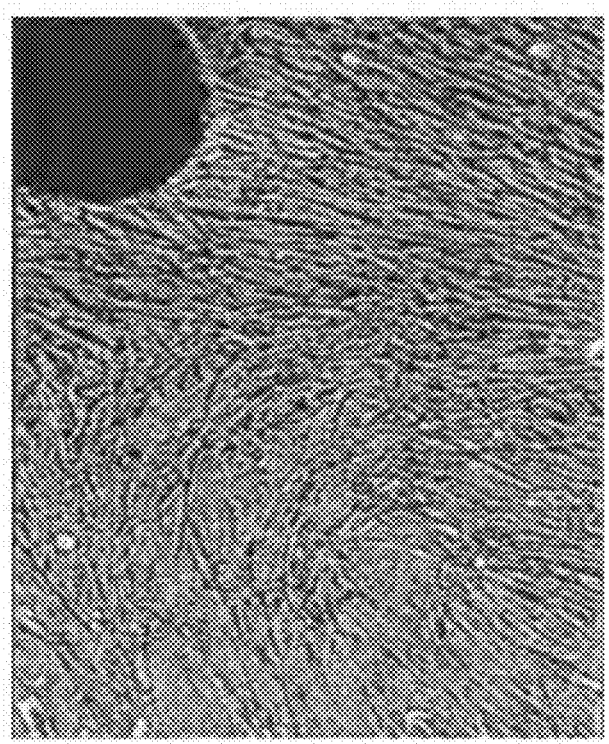
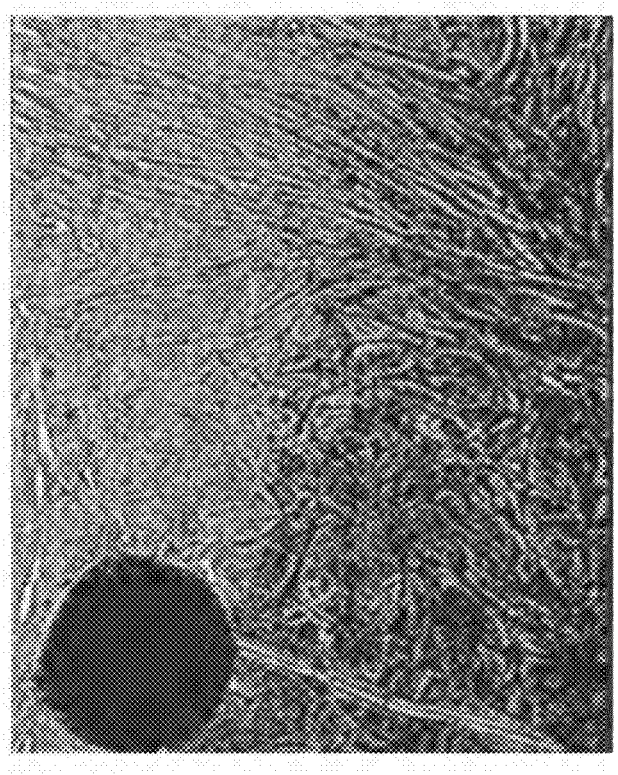

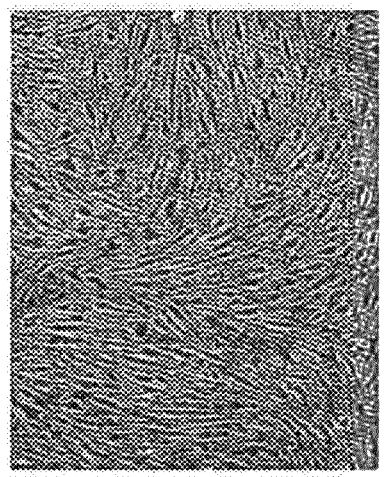
FIG.5B NF109 in DMEM
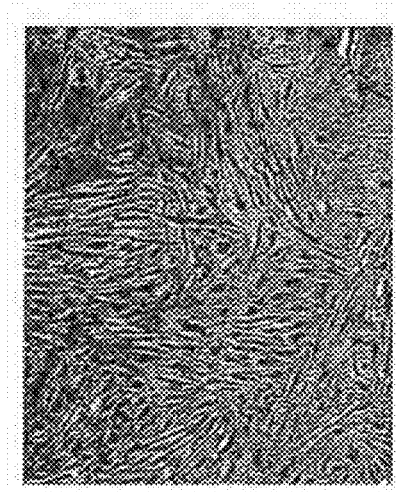
FIG.5D ADMC in DMEM
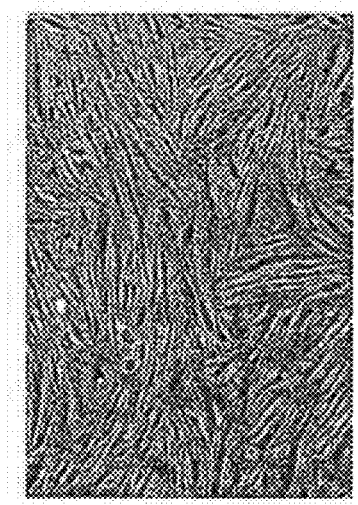
FIG.5A NF109 in 10% FCS
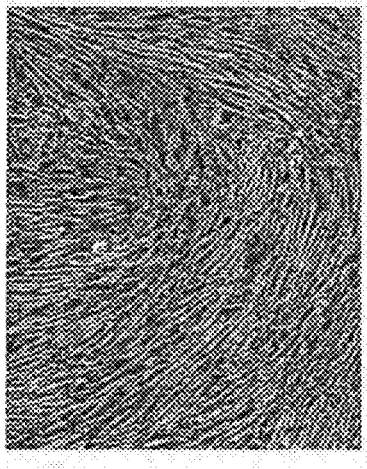
FIG.5C ADMC3 in 10% FCS UCMC3 in DMEM UCMC4 in DMEM UCMC3 in DMEM/10%FCS UCMC4 in DMEM/10%FCS Colony formation of umbilical cord mesenchymal stem cells cultured in non-feeder layer condition in DMEM/10%FCS Day 3

Day 7

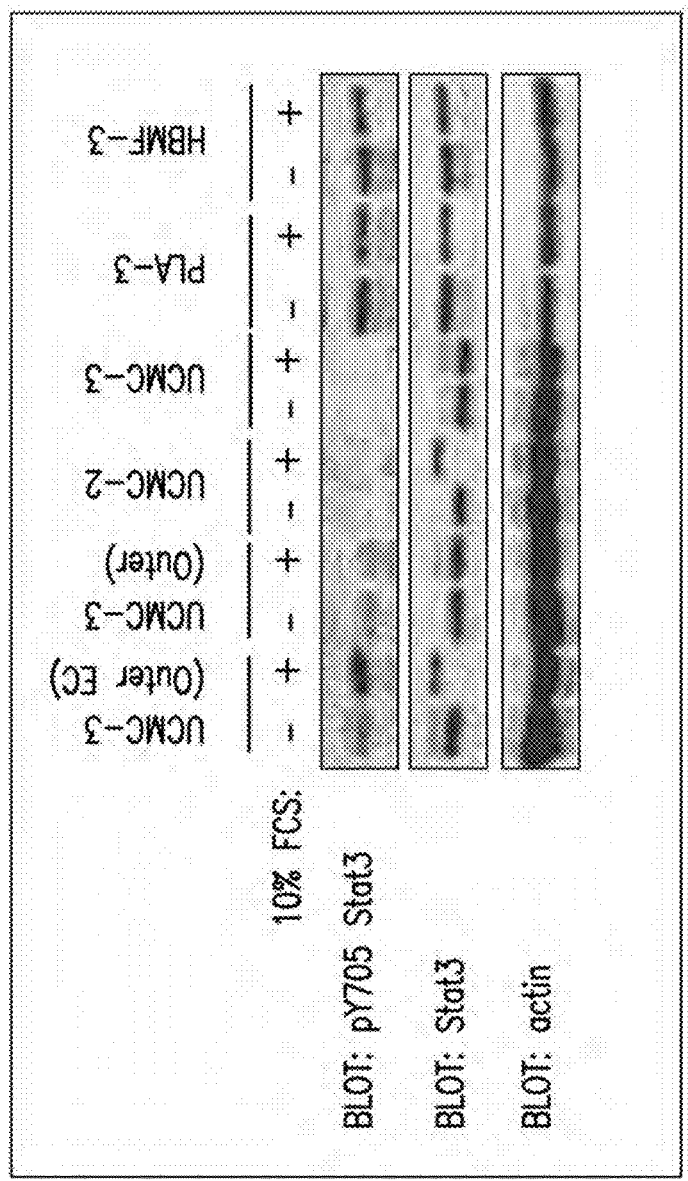

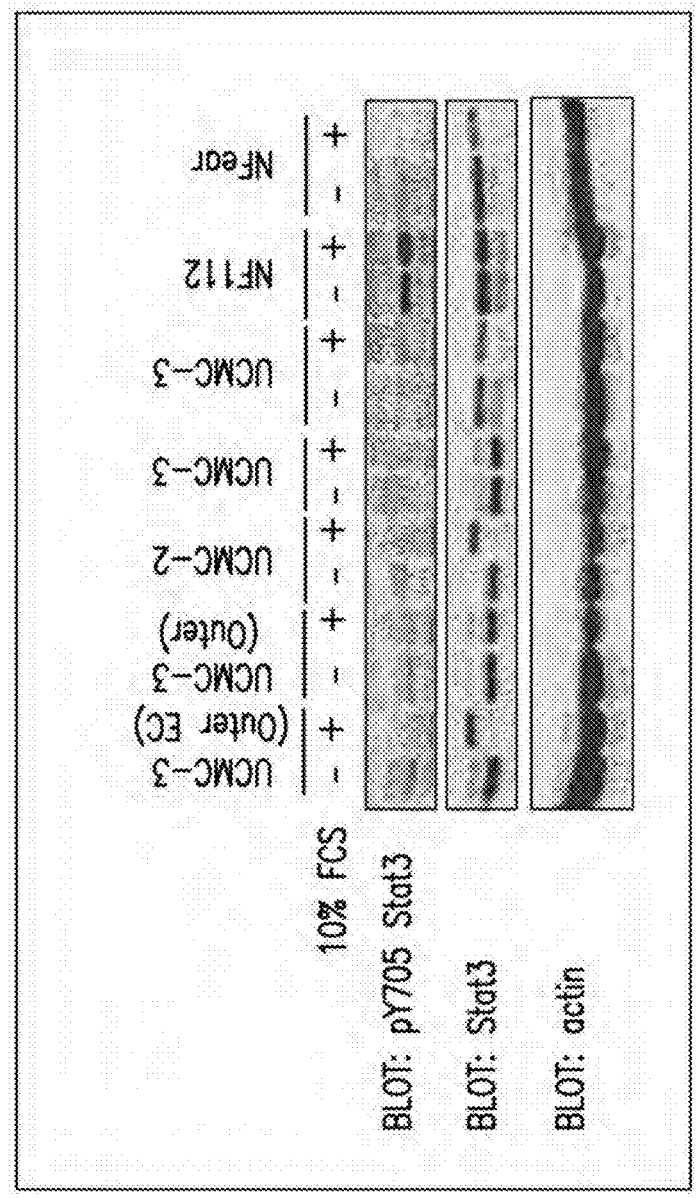

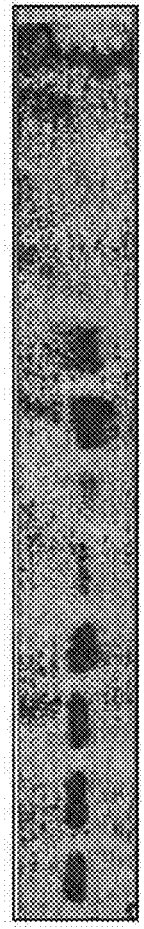
FIG. 9-5 Expression of Placental Growth Factor (PLGF) Stem Cells (UCMC)
1 UCMC-3
2 UCMC-3
3 UCMC-2
4 UCMC-2
5 UCMC-3
6 UCMC-3
7 UCMC-4
8 UCMC-4
9 NF 111
10 NF 111
11 NF 113
12 NF 113

Expression of Connective Tissue Growth Factor (CTFG) in Umbilical Cord Mesenchymal Stem Cells (UCMC)

1 UCMC-3
2 UCMC-3
3 UCMC-4
4 UCMC-4
5 NF 106
6 NF 106
7 NF 112
8 NF 112
9 NF 101
10 NF 101

Expression of Connective Tissue Growth Factor (CTFG) in Umbilical Cord Mesenchymal Stem Cells (UCMC)

1 UCMC-3
2 UCMC-3
3 UCMC-3
4 UCMC-3
5 UCMC-2
6 UCMC-2
7 UCMC-3
4 UCMC-4

9 hBMSC-1
10 hBMSC-1
11 ADMC
12 ADMC
13 hBMSC-3
14 hBMSC-3

Expression of Vascular Endothelial Growth Factor (VGF) in Umbilical Cord Mesenchymal Stem Cells (UCMC)

1 UCMC-3
2 UCMC-3
3 UCMC-4
4 UCMC-4
5 hBMSC-1
6 hBMSC-1
7 ADMC
8 ADMC
9 hBMSC-3
10 hBMSC-3

Expression of Hepatoma Derived Growth Factor (HDGF) in Umbilical Cord Mesenchymal Stem Cells (UCMC)

1: UCMC-3
2: UCMC-3
3: UCMC-2
4: UCMC-2
5: UCMC-3
6: UCMC-3
7: NF-111
8: NF-111
9: NF-105
10: NF-105

Expression of alpha-Smooth Muscle Actin (α-SMA) in Umbilical Cord Mesenchymal Stem Cells (UCMC)

1. UCMC4
2. UCMC4
3. UCMC7
4. UCMC7
5. CBMC4
6. CBMC4
7. CBMC12
8. CBMC12
9. UCEC10
10. NK (ar)
11. NFmix
12. NFmix
13. NF6
14. NF6

Expression of Syndecan-1 in Umbilical Cord Mesenchymal Stem Cells (UCMC)

1 UCMC-3
2 UCMC-3
3 UCMC-3
4 UCMC-3
5 UCMC-2
6 UCMC-2

Expression of Syndecan-2 in Umbilical Cord Mesenchymal Stem Cells (UCMC)

1 UCMC-1
2 UCMC-1
3 UCMC-3
4 UCMC-3
5 UCMC-2
6 UCMC-2
7 UCMC-4
8 UCMC-4
9 UCMC-5
10 UCMC-5
11 NF 106
12 NF 106
13 NF 112
14 NF 112

Expression of Syndecan-2 in Umbilical Cord Mesenchymal Stem Cells (UCMC)

1 UCMC-1
2 UCMC-1
3 UCMC-3
4 UCMC-3
5 UCMC-2
6 UCMC-2
7 UCMC-4
8 UCMC-4
9 UCMC-5
10 UCMC-5
11 NF 106
12 NF 106
13 NF 112
14 NF 112

Expression of Syndecan-4 in Umbilical Cord Mesenchymal Stem Cells (UCMC)

1 UCMC-1
2 UCMC-1
3 UCMC-3
4 UCMC-3
5 UCMC-2
6 UCMC-2
7 UCMC-4
8 UCMC-4
9 UCMC-5
10 UCMC-5
11 NF 106
12 NF 106
13 NF 112
14 NF 112

Expression of Stem cell marker Bmi-1 in Umbilical Cord Mesenchymal Stem Cells and Epithelial Stem Cells 1. UCMC-3,
2. UCMC-16
3. UCMC-15
4. UCMC-14
5. UCMC-17
6. UCMC-10
7. NF2
8. hBMSC-3
9. hBMSC-2

Expression of Leukemia Inhibitory Factor (LIF) in Umbilical Cord Mesenchymal Stem Cells and Epithelial Stem Cells 1. UCMC-14,
2. UCMC-14
3. UCMC-15
4. UCMC-15
5. UCEC-10
6. NK-ear
7. NF-mix
8. NF-mix
9. NF-6
10. NF-6

Highly Secreted ActivinA and Follistatin in Umbilical Cord Mesenchymal (UCMC) and Epithelial Stem Cells (UCMC) in Comparison with Bone Marrow (hBMF-3), Adiposed Derived Stem Cells (hMBSC-3), Human Dermal Fibroblasts (NF) and Epidermal Keratnicytes (NK)

| | ActivinA (ng/ml) | Follistatin (ng/ml) |
|---|---|---|
| UCMC-3 | 2.975 | 13.50 |
| UCMC-2 | 6.350 | 14.97 |
| UCMC-3 | 1.161 | 8.65 |
| UCMC-16 | 2.520 | 6.22 |
| hBMF-3 | 0.707 | 8.84 |
| hBMSC-3 | 0.061 | 11.24 |
| PLA-3 | 0.135 | 10.29 |
| NF-109 | <0.010 | 21.80 |
| nscF-1 | 0.032 | 14.95 |
| NF-112 | 0.040 | 11.54 |
| NF | <0.010 | 4.71 |
| NF-113 | <0.010 | 16.54 |
| NF-115 | 0.196 | 5.66 |
| NF-6 | <0.010 | 8.35 |
| UCEC-10 | 1.017 | 87.84 |
| UCEC-12 | 0.722 | 74.02 |
| UCEC-10 | 0.536 | 33.78 |
| UCEC-3 | 0.691 | 32.07 |
| UCEC-3 | 1.032 | 14.04 |
| UCEC-10 | 0.505 | 88.66 |
| UCEC-3 | 0.221 | 5.61 |
| NK-103 | 0.428 | 69.04 |

FIG.9-30

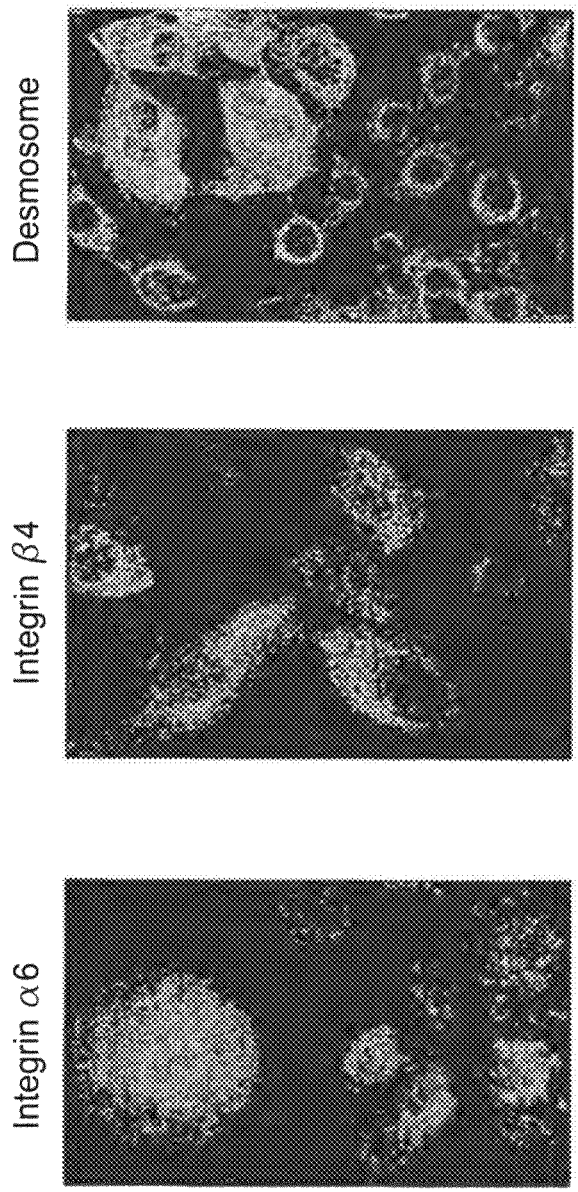

Spotting of Chip used for Cytokine Array (6.1)

| | A | B | C | D | E | F | G | H | I | J | K | L | M | N |
|---|---|---|---|---|---|---|---|---|---|---|---|---|---|---|
| 1 | POS | POS | POS | POS | Blank | Angiogenin | BDNF | BLC | BMP-4 | BMP-6 | CK b 8-1 | CNTF | EGF | Eotaxin |
| 2 | NEG | NEG | NEG | NEG | Blank | Angiogenin | BDNF | BLC | BMP-4 | BMP-6 | CK b 8-1 | CNTF | EGF | Eotaxin |
| 3 | Eotaxin-2 | Eotaxin-3 | FGF-6 | FGF-7 | Flt-3 Ligand | Fractalkine | GCP-2 | GDNF | GM-CSF | I-309 | IFN-g | IGFBP-1 | IGFBP-2 | IGFBP-4 |
| 4 | Eotaxin-2 | Eotaxin-3 | FGF-6 | FGF-7 | Flt-3 Ligand | Fractalkine | GCP-2 | GDNF | GM-CSF | I-309 | IFN-g | IGFBP-1 | IGFBP-2 | IGFBP-4 |
| 5 | IGF-I | IL-10 | IL-13 | IL-15 | IL-16 | IL-1a | IL-1b | IL-1ra | IL-2 | IL-3 | IL-4 | IL-5 | IL-6 | IL-7 |
| 6 | IGF-I | IL-10 | IL-13 | IL-15 | IL-16 | IL-1a | IL-1b | IL-1ra | IL-2 | IL-3 | IL-4 | IL-5 | IL-6 | IL-7 |
| 7 | Leptin | LIGHT | MCP-1 | MCP-2 | MCP-3 | MCP-4 | M-CSF | MDC | MIG | MIP-1d | MIP-3a | NAP-2 | NT-3 | PARC |
| 8 | Leptin | LIGHT | MCP-1 | MCP-2 | MCP-3 | MCP-4 | M-CSF | MDC | MIG | MIP-1d | MIP-3a | NAP-2 | NT-3 | PARC |
| 9 | PDGF-BB | RANTES | SCF | SDF-1 | TARC | TGF-b1 | TGF-b3 | TNF-a | TNF-b | Blank | Blank | Blank | Blank | Blank |
| 10 | PDGF-BB | RANTES | SCF | SDF-1 | TARC | TGF-b1 | TGF-b3 | TNF-a | TNF-b | Blank | Blank | Blank | POS | POS |

FIG. 12-6

Spotting of Chip used for Cytokine Array (7.1)

| | A | B | C | D | E | F | G | H | I | J | K | L | M | N |
|---|---|---|---|---|---|---|---|---|---|---|---|---|---|---|
| 1 | POS | POS | POS | POS | Blank | Acrp30 | AgRP | Angiopoietin-2 | Amphiregulin | Axl | bFGF | b-NGF | BTC | CCL-28 |
| 2 | NEG | NEG | NEG | NEG | Blank | Acrp30 | AgRP | Angiopoietin-2 | Amphiregulin | Axl | bFGF | b-NGF | BTC | CCL-28 |
| 3 | CTACK | Dtk | EGF-R | ENA-78 | FAS | FGF-4 | FGF-9 | GCSF | GITR Ligand | GITR | GRO | GRO-α | HCC-4 | HGF |
| 4 | CTACK | Dtk | EGF-R | ENA-78 | FAS | FGF-4 | FGF-9 | GCSF | GITR Ligand | GITR | GRO | GRO-α | HCC-4 | HGF |
| 5 | ICAM-1 | ICAM-3 | IGFBP-3 | IGFBP-6 | IGF-1 SR | IL-1 R4/ST2 | IL-1 RI | IL-11 | IL-12 p40 | IL-12 p70 | IL-17 | IL-2 Ra | IL-6 R | IL-8 |
| 6 | ICAM-1 | ICAM-3 | IGFBP-3 | IGFBP-6 | IGF-1 SR | IL-1 R4/ST2 | IL-1 RI | IL-11 | IL-12 p40 | IL-12 p70 | IL-17 | IL-2 Ra | IL-6 R | IL-8 |
| 7 | I-TAC | Lymphotactin | MIF | MIP-1a | MIP-1b | MIP-3b | MSP-α | NT-4 | Osteoprotegerin | Oncostatin M | PIGF | sgp130 | sTNF RII | sTNF-RI |
| 8 | I-TAC | Lymphotactin | MIF | MIP-1a | MIP-1b | MIP-3b | MSP-α | NT-4 | Osteoprotegerin | Oncostatin M | PIGF | sgp130 | sTNF RII | sTNF-RI |
| 9 | TECK | TIMP-1 | TIMP-2 | Thrombopoietin | TRAIL R3 | TRAIL R4 | uPAR | VEGF | VEGF-d | Blank | Blank | Blank | Blank | Blank |
| 10 | TECK | TIMP-1 | TIMP-2 | Thrombopoietin | TRAIL R3 | TRAIL R4 | uPAR | VEGF | VEGF-d | Blank | Blank | Blank | POS | POS |

FIG.12-7

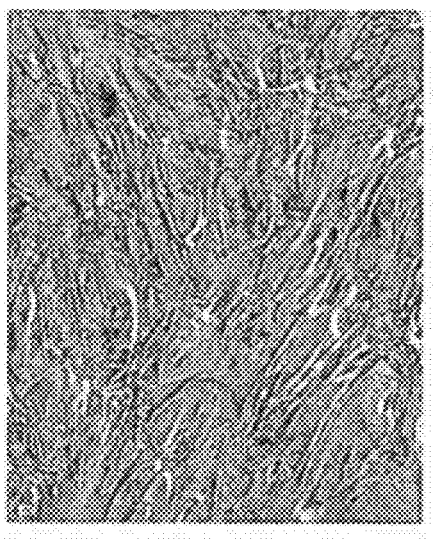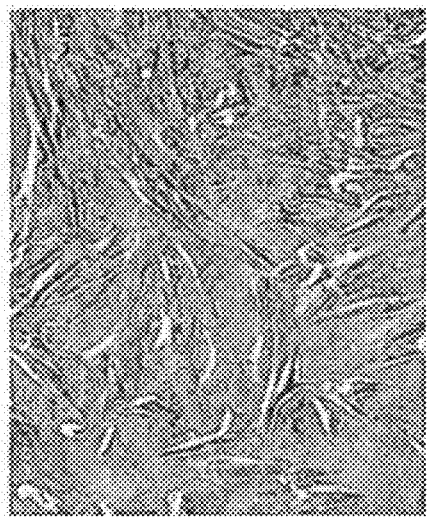
UCMC-16 cultured in DMEM/10%FCS, at day 10
FIG. 13-1

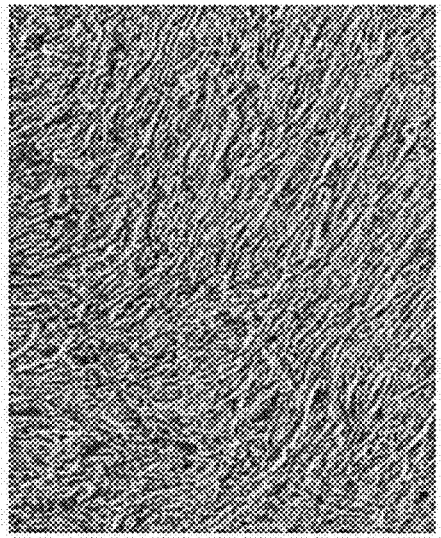
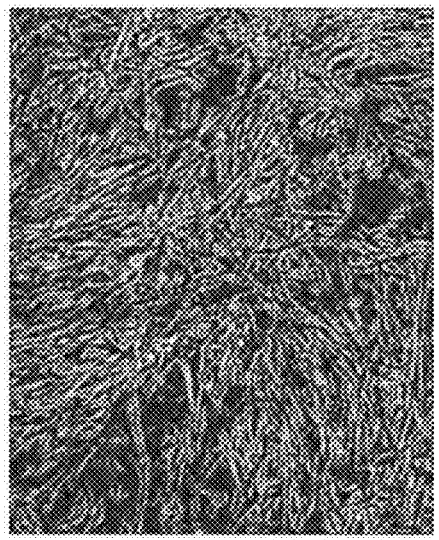
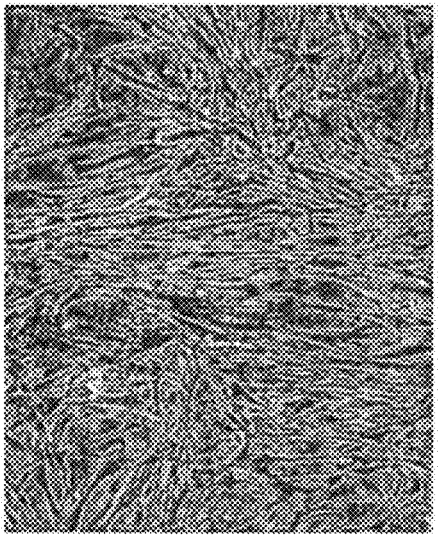
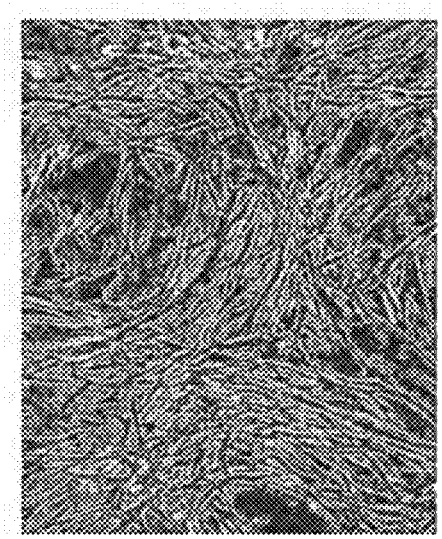
UCMC-16 cultured in PTT-2 at day 10
FIG. 13-4

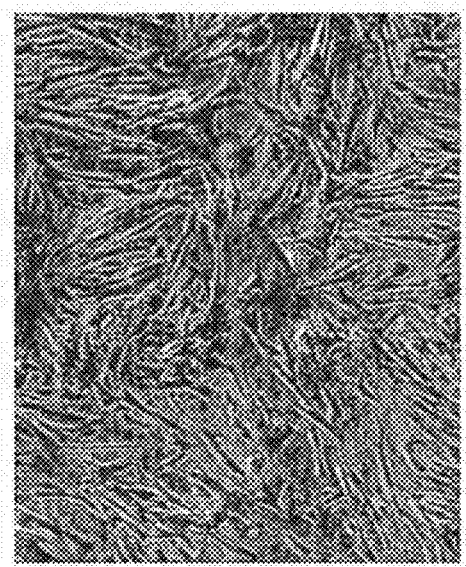
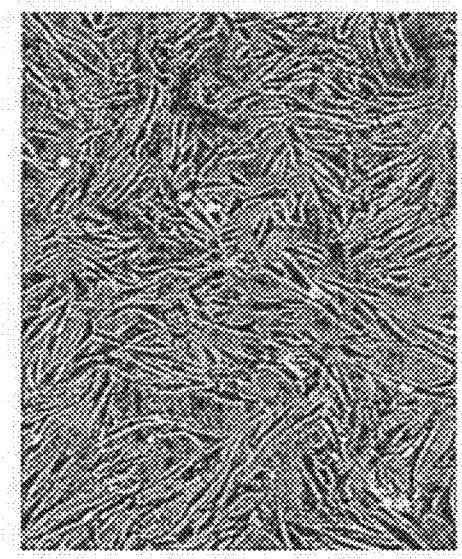
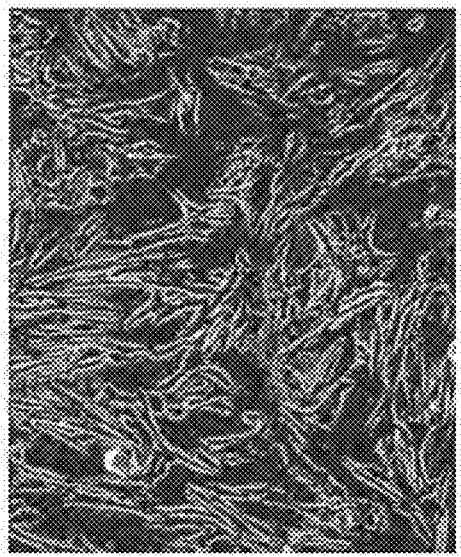
UCMC-16 cultured in PTT-3 at day 10
FIG. 13-5

Adipose-derived stromal cells cultured in PTT-3 at day 10. Cells did not grow well in serum free medium

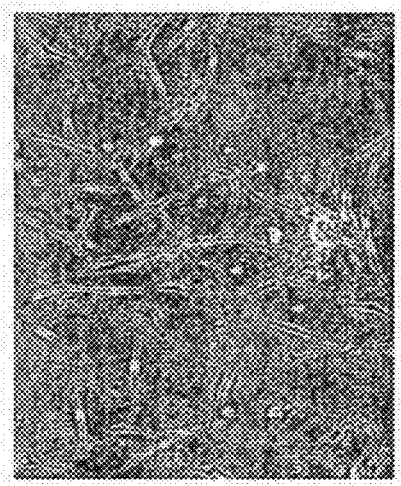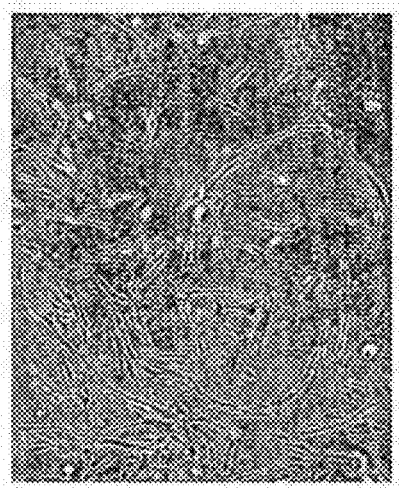
FIG. 13-7 Bone marrow-derived stromal cells cultured in PTT-3 (MeE) at day 10. Cells did not grow well in serum free medium

ISOLATION, CULTIVATION AND USES OF STEM/PROGENITOR CELLS

CROSS-REFERENCE TO RELATED APPLICATIONS

This application is a divisional of U.S. patent application Ser. No. 11/205,248 filed Aug. 15, 2005, which claims the benefit of U.S. Provisional Application No. 60/602,208, filed Aug. 16, 2004, and of U.S. Provisional Application No. 60/632,209, filed Dec. 1, 2004, the contents of each being hereby incorporated by reference it its entirety for all purposes.

FIELD OF THE INVENTION

The present invention relates to a method for isolating stem/progenitor cells from the amniotic membrane of umbilical cord, wherein the method comprises separating the amniotic membrane from the other components of the umbilical cord in vitro, culturing the amniotic membrane tissue under conditions allowing cell proliferation, and isolating the stem/progenitor cells from the tissue cultures. In particular, the invention relates to the isolation and cultivation of stem cells having embryonic properties such as epithelial and/or mesenchymal stem/progenitor cells under conditions allowing the cells to undergo mitotic expansion. Furthermore, the invention is directed to a method for the differentiation of the isolated stem/progenitor cells into epithelial and/or mesenchymal cells and therapeutic uses of these stem/progenitor cells.

BACKGROUND OF THE INVENTION

Stem cells are a cell population possessing the capacities to self-renew indefinitely and to differentiate in multiple cell or tissue types. Embryonic stem cells (from approximately days 3 to 5 after fertilisation) proliferate indefinitely and can differentiate spontaneously into all tissue types: they are thus termed pluripotent stem cells (reviewed, for example, in Smith, A. G. (2001) *Annu. Rev. Cell. Dev. Biol.* 17, 435-462). Adult stem cells, however, are more tissue-specific and may have less replicative capacity: they are thus termed multipotent stem cells (reviewed, for example, in Paul, G. et al. (2002) *Drug Discov. Today* 7, 295-302). The "plasticity" of embryonic and adult stem cells relies on their ability to trans-differentiate into tissues different from their origin and, perhaps, across embryonic germ layers.

The ability of stem cells to self-renew is critical to their function as reservoir of primitive undifferentiated cells. In contrast, most somatic cells have a limited capacity for self-renewal due to telomere shortening (reviewed, for example, in Dice, J. F. (1993) *Physiol. Rev.* 73, 149-159). Stem cell-based therapies thus have the potential to be useful for the treatment of a multitude of human and animal diseases.

Stem cells as well as stem/progenitor cells can be derived from different sources. The "multi-lineage" potential of embryonic and adult stem cells has been extensively characterized. Even though the potential of embryonic stem cells is enormous, their use implies many ethical problems. Therefore, non-embryonic stem cells derived from the bone marrow stroma, fat tissue, dermis and umbilical cord blood have been proposed as alternative sources. These cells can differentiate inter alia into chondrocytes, adipocytes, osteoblasts, myoblasts, cardiomyocytes, astrocytes, and tenocytes in vitro and undergo differentiation in vivo, making these stem cells—in general referred to as mesenchymal stem cells—promising candidates for mesodermal defect repair and disease management.

In clinical use, however, harvesting of such mesenchymal stem cells causes several problems. The collection of the cells is a mental and physical burden to the patient as a surgical procedure is required to obtain the cells (for example, the collection of bone marrow is an invasive technique performed with a biopsy needle that requires local or even general anesthesia). Furthermore, in many cases the number of stem cells extracted is rather low. More importantly, no epithelial cells are derived or differentiated from these cells. This prompted the search for other possible sources of stem cells.

Umbilical cord blood has been identified as a rich source of haematopoetic stem/progenitor cells. However, the existence of mesenchymal stem/progenitor cells is discussed controversially. On the one hand, such cells could not be isolated or successfully cultured from term umbilical cord blood (Mareschi, K. et al. (2001) *Haematologica* 86, 1099-1100). At the same time, results obtained by Campagnoli, C. et al. (*Blood* (2001) 98, 2396-2402) as well as Erices, A. et al. (*Br. J. Haematol.* (2000) 109, 235-242) suggest that mesenchymal stem cells are present in several fetal organs and circulate in the blood of pre-term fetuses simultaneously with hematopoietic precursors. Accordingly, International Patent Application WO 03/070922 discloses isolation and culture-expansion methods of mesenchymal stem/progenitor cells from umbilical cord blood and a differentiation method of such cells into various mesenchymal tissues. Isolation efficiencies of about 60% have been reported (Bieback, K. et al. (2004) *Stem Cells* 22, 625-634). In the same study, both the time period from collection of the umbilical cord blood to isolation of the cells and the volume of the blood sample used have been determined as crucial parameters for achieving such a yield. However, it is still a matter of debate whether these stem/progenitor cells are indeed derived of umbilical cord tissue.

Recently, mesenchymal stem/progenitor cells have been successfully isolated from umbilical cord tissue, namely from Wharton's jelly, the matrix of umbilical cord, (Mitchell, K. E. et al. (2003) *Stem Cells* 21, 50-60; U.S. Pat. No. 5,919,702; US Patent Application 2004/0136967). These cells have been shown to have the capacity to differentiate, for example, into a neuronal phenotype and into cartilage tissue, respectively. Furthermore, mesenchymal stem/progenitor cells have also been isolated from the endothelium and the subendothelial layer of the umbilical cord vein, one of the three vessels (two arteries, one vein) found within the umbilical cord (Romanov, Y. A. et al. (2003) *Stem Cells* 21, 105-110; Covas, D. T. et al. (2003) *Braz. J. Med. Biol. Res.* 36, 1179-1183).

However, none of these approaches employed thus far has resulted in the isolation or cultivation of epithelial stem/progenitor cells as a source for epithelial cell-based therapies such as skin resurfacing, liver repair, bladder tissue engineering and other engineered surface tissues. Thus, there is still a need for methods and reliable sources useful for the isolation and cultivation of epithelial stem/progenitor cells. Furthermore, rapid and efficient methods which are ethically acceptable and do not pose a biomedical burden on the patient for the isolation of epithelial and mesenchymal stem/progenitor cells are still required in order to provide such cells in a sufficient amount for various applications in regenerative medicine and tissue engineering.

SUMMARY OF THE INVENTION

The invention provides a method for isolating stem/progenitor cells from the amniotic membrane of umbilical cord, the method comprising:
(a) separating the amniotic membrane from the other components of the umbilical cord in vitro;
(b) culturing the amniotic membrane tissue obtained in step (a) under conditions allowing cell proliferation; and
(c) isolating the stem/progenitor cells.

In one embodiment, the invention provides a method, further comprising:
(a) separating the cells from the amniotic membrane tissue before cultivation by a technique selected from the group consisting of enzymatic digestion and direct tissue explant.

In one preferred embodiment, the invention provides a method for isolating stem/progenitor cells that have embryonic stem cell-like properties.

In another preferred embodiment, the invention provides a method for isolating epithelial and/or mesenchymal stem/progenitor cells.

In another embodiment, the invention provides a method further comprising:
(d) culturing the stem/progenitor cells under conditions allowing the cells to undergo clonal expansion.

In yet another embodiment, the invention provides a method further comprising:
(e) culturing the stem/progenitor cells under conditions allowing the differentiation of said cells into epithelial cells and/or mesenchymal cells; and
(f) isolating the differentiated cells.

In yet another embodiment, the invention provides a method, further comprising:
(g) preserving the isolated stem/progenitor cells for further use.

In yet a further embodiment, the invention comprising a method of cultivating stem/progenitors cells of the invention, comprising:
Obtaining a tissue explant from the amniotic membrane of umbilical cord;
Cultivating the tissue explant in suitable cultivation media and cultivation conditions over a suitable period of time.

In yet other embodiments, the invention is directed to therapeutic uses of the stem/progenitor cells or cells differentiated therefrom or cellular secretions or extracts thereof. One of these embodiments provide a method of treating a subject having a disorder comprising administering to the subject an effective amount of a stem/progenitor cell isolated by the inventive method of explained above. Another embodiment comprises administering to the subject an effective amount of a cell differentiated from a stem/progenitor cell of the invention. Other embodiments provide a corresponding pharmaceutical composition, i.e. a pharmaceutical composition comprising a stem progenitor cell or a cell differentiated therefrom, as well as cellular secretions into the cell medium and extracts.

BRIEF DESCRIPTION OF THE DRAWINGS

The invention will be better understood with reference to the detailed description when considered in conjunction with the non-limiting examples and the drawings, in which:

FIG. 1A depicts epithelial cell outgrowth of tissue culture from umbilical cord amniotic membrane by the method of direct tissue explant (40× magnification) at day 2, while

FIG. 2A and FIG. 2C depict enzymatic digestion of the umbilical cord segments yielding similar epithelial (40× magnification) cells at day 2, while

FIG. 3A and FIG. 3C show that cellular outgrowth was observed as early as 48 hours after placement in tissue culture dishes using DMEM supplemented with 10% fetal calf serum (FCS) as culture medium (40× magnification). The explants were submerged in 5 ml DMEM (Invitrogen) supplemented with 10% fetal bovine serum (Hyclone) (DMEM/10% FBS). Medium was changed every 2 or 3 days. Cell outgrowth was monitored under light microscopy. Microphotographs were taken at different time intervals. FIG. 3B and FIG. 3D show that the cells were characterized by their spindle shaped morphology, and migrated and expanded both easily and quickly in vitro, closely resembling fibroblasts.

FIG. 4A and FIG. 4B depict mesenchymal cells from umbilical cord amniotic membrane cells isolated by collagenase enzymatic digestion. FIG. 4A shows mesenchymal cells isolated from umbilical cord amniotic membrane at day 2. FIG. 4B (40× magnification) shows that cell proliferation was observed at day 5. Umbilical cord amniotic membrane was divided into small pieces of 0.5 cm×0.5 cm and digested in 0.1% (w/v) collagenase type1 solution (Roche Diagnostics) at 37° C. for 6 hours. The samples were vortexed every 15 min for 2 min. Cells were harvested by centrifugation at 4000 rpm for 30 min. Cell pellets were resuspended in DMEM/10% FBS, counted and seeded on 10 cm tissue culture dish at density of 1×10$^6$ cells/dish. Medium was changed every 2 or 3 days. Cell outgrowing was monitored under light microscopy. Microphotographs were taken at different time intervals. Once again, cells demonstrated spindle shaped morphology typical of mesenchymal cells as fibroblasts.

FIG. 5A to FIG. 5H (40× magnification) depict the morphology in serum-free culture condition (DMEM) and serum culture condition (DMEM/10% FCS) of umbilical cord amniotic membrane mesenchymal cells (UCMC) isolated according to the method of the invention, normal dermal fibroblasts (NF109 cells) and adipose-derived mesenchymal cells (ADMC). In more detail, FIG. 5A and FIG. 5B both show normal dermal fibroblasts (NF109 cells), FIG. 5C and FIG. 5D both show adipose-derived mesenchymal cells (ADMC), and each of FIG. 5E, FIG. 5F, FIG. 5G, and FIG. 5H show umbilical cord amniotic membrane mesenchymal cells (UCMC) isolated in the invention.

FIG. 8-B (40× magnification) shows the colony forming efficiency assay of the umbilical cord mesenchymal cells.

FIG. 9-16 shows expression of stem cell factor (SCF), FIG. 9-17 shows expression of alpha-Smooth Muscle Actin (α-SMA), FIG. 9-18 and FIG. 9-19 show expression of Fibronectin, FIG. 9-20 shows expression of Decorin, FIG. 9-21 shows expression of Syndecan-1, FIG. 9-22 and FIG. 9-23 both show expression of Syndecan-2, FIG. 9.24 and FIG. 9-25 both show expression of Syndecan-3, and FIG. 9-26 shows expression of Syndecan-4). FIG. 9-27 shows expression of Bmi-1, and FIG. 9.28 shows expression of Leukemia inhibitory factor (LIF).

FIG. 9-29 shows secretion of Leukemia inhibitory factor detected by Western blot analysis.

FIG. 9-30 shows highly secreted Activin A and Follistatin detected by ELISA assay, respectively in supernatants of umbilical cord mesenchymal and epithelial stem cell culture in comparison with bone marrow, adipose derived stem cells, human dermal fibroblasts and epidermal keratinocytes.

FIG. 10-1 to FIG. 10-4 show indirect immunofluorescent analysis of markers of epithelial cells expressed in umbilical cord epithelial stem cells, with FIG. 10-1 showing analysis of markers such as cytokeratins (CK)-general, CK17, CK6, CK10, CK19, CK18, CK16, CK15, FIG. 10-2 showing analysis of Hemidesmosome components-integrin alpha6, integrin beta4; Desmosome components, FIG. 10-3 showing analysis of basement membrane components-laminin1, laminin5, collagen IV, collagen VII and FIG. 10-4 showing analysis of other important extracellular matrix components as integrin-beta1 and fibronectin.

FIG. 11-1 to FIG. 11-4 show cytokine array analysis of secreted cytokines and growth factors by umbilical cord mesenchymal stem cells (UCMC) in comparison with human bone-marrow mesenchymal stem cells. In more detail, FIG. 11-1 shows an expression profile of secreted cytokines and growth factors by umbilical cord mesenchymal cells, FIG. 11-2 also shows an expression profile of secreted cytokines and growth factors by umbilical cord mesenchymal cells, FIG. 11-3 further shows an expression profile of secreted cytokines and growth factors by umbilical cord mesenchymal cells, and also FIG. 11-4 shows an expression profile of secreted cytokines and growth factors by umbilical cord mesenchymal cells.

FIG. 12-1 to FIG. 12-7 show cytokine array analysis of secreted cytokines and growth factors by umbilical cord epithelial stem cells (UCEC) in comparison with human epidermal keratinocytes. In more detail, FIG. 12-1 shows an expression profile of secreted cytokines and growth factors by umbilical cord epithelial cells, FIG. 12-2 also shows an expression profile of secreted cytokines and growth factors by umbilical cord epithelial cells, FIG. 12-3 shows an expression profile of secreted cytokines and growth factors by human epidermal keratinocytes, FIG. 12-4 also shows an expression profile of secreted cytokines and growth factors by human epidermal keratinocytes, FIG. 12-5 shows an expression profile of secreted cytokines and growth factors by umbilical cord epithelial cells, FIG. 12-6 shows a spotting of a chip used for cytokine array, and FIG. 12-7 also shows a spotting of a chip used for cytokine array.

FIG. 13-1 shows UCMC cells cultured in DMEM supplemented with 10% fetal calf serum (FCS), FIG. 13-2 shows UCMC cells cultured in serum-free media PTT-1 at day 4, FIG. 13-3 shows UCMC cells cultured in serum-free media PTT-1 at day 10, FIG. 13-4 shows UCMC cells cultured in serum-free media PTT-2, and FIG. 13-5 shows UCMC cells cultured in serum-free media PTT-3. FIG. 13-6 shows the growth of adipose derived stromal cells in serum free medium PTT-3 and FIG. 13-7 shows the growth of bone marrow derived stromal cells in serum free medium PTT-3.

FIG. 14 shows global gene expression in umbilical cord epithelial and mesenchymal stem cells analyzed by DNA microarray. UCEC expressed a total of 28055 genes and UCMC expressed a total of 34407 genes. There are 27308 overlapping genes expressing in both cell types. 747 genes expressed were unique to UCEC and 7099 genes expressed were unique to UCMC. The selected genes of interest are presented in this Figure. Both stem cell types expressed 140 genes related to embryonic stem cells and embryonic development.

FIG. 15 shows a schematic illustration of expansion of umbilical cord epithelial and mesenchymal stem cells using repetitive explants of umbilical cord lining membrane tissues.

FIG. 16 depicts a cross section of an umbilical cord demonstrating the umbilical cord amniotic lining membrane (LM), the contained Wharton's jelly (WJ), as well as two umbilical arteries (UA) and one umbilical vein (UV) supported within this jelly.

DETAILED DESCRIPTION

Figure 1A:
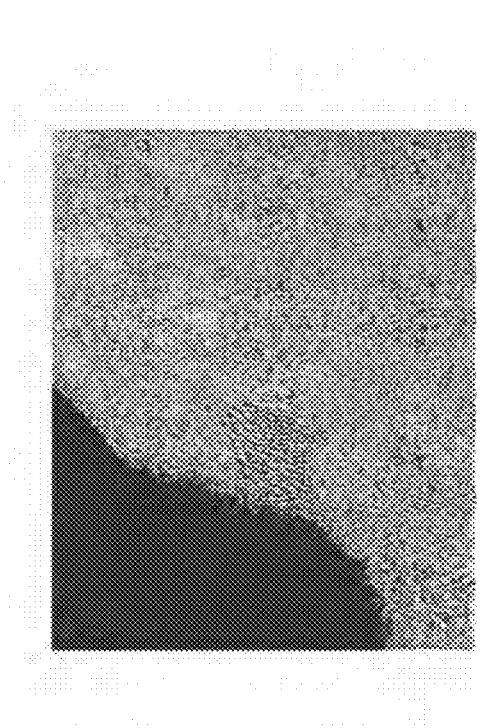

The invention is based on the surprising finding that the amniotic membrane of umbilical cord represents a source, from which stem/progenitor cells such as mesenchymal and epithelial stem/progenitor cells can be successfully isolated and expanded under in vitro conditions. Even more surprising is the finding that these cells show embryonic stem cell-like characteristics. The amniotic membrane (also called amniotic lining membrane), i.e. thin innermost membranous sac enclosing the placenta and developing embryo of mammals, has recently been used as a natural substrate in ocular surface reconstruction and as a biological substrate for expanding limbal epithelial stem cells (cf., e.g., Anderson, D. F. et al. (2001) *Br. J. Ophthalmol.* 85, 567-575; Grüterich, M. et al. (2003) *Surv. Ophthalmol.* 48, 631-646). However, no methods have been described thus far for the isolation of stem/progenitor cells from the amniotic membrane, at least for humans, nor has the amniotic membrane covering the umbilical cord been reported as a source for stem cells.

The invention provides a method for isolating stem/progenitor cells from the amniotic membrane of umbilical cord, the method comprising:

(a) separating the amniotic membrane from the other components of the umbilical cord in vitro;

(b) culturing the amniotic membrane tissue obtained in step (a) under conditions allowing cell proliferation; and (c) isolating the stem/progenitor cells.

For isolation of the cells of the invention from umbilical cord, the umbilical cord or a part thereof is usually collected immediately after birth (of a child in the case of humans) and for transport to the laboratory transferred in a medium that is suitable for handling of mammalian tissue. Examples of such media include, but are not limited to Leibovitz media which are commercially available from suppliers such as Sigma Aldrich, Saint Louis, USA or HyClone, Logan, Utah, USA. The umbilical cord is then typically processed under sterile conditions. Processing of the cord typically includes removing the blood that has remained on the surface or within the blood vessels of the umbilical cord by washing with a suitable buffer such as phosphate buffered saline. The umbilical cord is then typically reduced to smaller pieces, for example by cutting, and washed again before separating the amniotic membrane from the other components. In this conjunction, it is noted that it is not necessary to process the umbilical cord of a mammalian donor immediately after birth but it is also possible, to collect the umbilical cord and, optionally after washing under sterile conditions and reducing it into smaller pieces, to preserve the umbilical cord or parts thereof by cryo-preservation and to store the so obtained specimen, for example in liquid nitrogen, for later isolation of the cells of the invention from the umbilical cord. Accordingly, an (intact) umbilical cord or a portion of an intact umbilical cord that is treated by cryo-preservation is also encompassed in the present invention. In addition, the umbilical cord amniotic membrane that has been separated from the other components of the umbilical cord and is then treated by cryo-preservation is also encompassed in the present invention.

The term "cryo-preservation" is used herein in its regular meaning to describe a process where cells or whole tissues are preserved by cooling to low sub-zero temperatures, such as (typically) $-80°$ C. or $-196°$ C. (the boiling point of liquid nitrogen). Cryo-preservation can be carried out as known to the person skilled in the art and can include the use of cryo-protectors such as dimethylsulfoxide (DMSO) or glycerol, which slow down the formation of ice-crystals in the cells of the umbilical cord.

The term "stem/progenitor cell" as used herein refers to any cell derived of umbilical cord having the capacities to self-renew indefinitely and to differentiate in multiple cell or tissue types such as endothelial cells, epithelial cells, fibroblasts, myocytes or neurons. Furthermore, the cells may be derived of any mammalian species, such as mouse, rat, guinea pig, rabbit, goat, dog, cat, sheep, monkey or human, with cells of human origin being preferred in one embodiment.

The term "embryonic stem cell-like properties" refers to the ability of the cells derived of umbilical cord that they can—almost like or exactly like embryonic stem cells—differentiate spontaneously into all tissue types, meaning that they are pluripotent stem cells.

The term "amniotic membrane" as used herein refers to the thin innermost membranous sac enclosing the developing embryo of mammals. During pregnancy, the fetus is surrounded and cushioned by a liquid called amniotic fluid. This fluid, along with the fetus and the placenta, is enclosed within a sac called the amniotic membrane, which also covers the umbilical cord. The amniotic fluid is important for several reasons. It cushions and protects the fetus, allowing the fetus to move freely. The amniotic fluid also allows the umbilical cord to float, preventing it from being compressed and cutting off the fetus' supply of oxygen and nutrients derived from the circulating blood within the placental blood vessels. The amniotic sac contains the amniotic fluid which maintains a homeostatic environment protecting the fetal environment from the outside world. This barrier additionally protects the fetus from organisms (like bacteria or viruses) that could travel up the vagina and potentially cause infection.

Media and reagents for tissue culture are well known in the art (cf., for example, Pollard, J. W. and Walker, J. M. (1997) *Basic Cell Culture Protocols, Second Edition*, Humana Press, Totowa, N.J.; Freshney, R.I. (2000) *Culture of Animal Cells, Fourth Edition*, Wiley-Liss, Hoboken, N.J.). Examples of suitable media for incubating/transporting umbilical cord tissue samples include, but are not limited to, Dulbecco's Modified Eagle Medium (DMEM), RPMI media, Hanks' Balanced Salt Solution (HBSS) phosphate buffered saline (PBS), and L-15 medium, with the latter one being preferred in some embodiments. Examples of appropriate media for culturing stem/progenitor cells according to the invention include, but are not limited to, Dulbecco's Modified Eagle Medium (DMEM), DMEM-F12, RPMI media, EpiLIfe medium, and Medium 171, with the latter being preferred in some embodiments. The media may be supplemented with fetal calf serum (FCS) or fetal bovine serum (FBS) as well as antibiotics, growth factors, amino acids, inhibitors or the like, which is well within the general knowledge of the skilled artisan.

In one embodiment, the invention provides a method, further comprising:

(a) separating these stem/progenitor cells from the amniotic membrane tissue by a enzymatic digestion and/or direct tissue explant technique before cultivation. The term "enzymatic digestion technique" as used herein means that enzymes are added to cleave the cells from the main tissue mass (here the amniotic membrane of the umbilical cord). The separated cells are subsequently collected. The term "direct tissue explant technique" as used herein means that the tissue is first placed in media without enzymes. Then under careful conditions the cells separate from the main tissue mass by itself- and the cells are then harvested for collection.

Methods for separating cells of a particular tissue or organ by treatment with enzymes or by direct tissue explant are well known in the art (cf., for example, Pollard, J. W. and Walker, J. M. (1997) *Basic Cell Culture Protocols, Second Edition*, Humana Press, Totowa, N.J.; Freshney, R.I. (2000) *Culture of Animal Cells, Fourth Edition*, Wiley-Liss, Hoboken, N.J.). Any enzyme catalyzing tissue dissociation may be used for performing the methods of the present invention. In some embodiments, collagenase is used for that purpose. The enzyme may be used as a crude preparation or in purified form. It may be purified from any prokaryotic or eukaryotic organism (with *Clostridium histolyticum* being most preferred) or produced recombinantly by means of gene technology. Any type of collagenase may be employed, i.e. type 1, type 2, type 3, type 4, or any combination thereof. In some embodiments the use of collagenase type 1 is being preferred.

In one embodiment, the invention provides a method for isolating stem/progenitor cells that have embryonic stem cell-like properties. These cells can ultimately be differentiated into, but not limited to, by morphology, epithelial or mesenchymal cells.

Accordingly, in another embodiment, the invention provides a method for isolating epithelial and/or mesenchymal stem/progenitor cells, wherein in accordance with the above disclosure these cells may have embryonic stem cell-like properties.

Epithelial stem/progenitor cells include any cells exhibiting a epithelial cell like morphology (i.e. a polyhedral shape) that can be differentiated into any type of epithelial cell such as, but not limited to, skin epithelial cells, hair follicular cells, cornea epithelial cells, conjunctival epithelial cells, retinal epithelial cells, liver epithelial cells, kidney epithelial cells, pancreatic epithelial cells, oesophageal epithelial cells, small intestinal epithelial cells, large intestinal epithelial cells, lung and airway epithelial cells, bladder epithelial cells or uterine epithelial cells.

Mesenchymal stem/progenitor cells include any cells exhibiting a mesenchymal cell like morphology (i.e. a spindle-like shape) that can be differentiated into any type of mesenchymal cell such as, but not limited to, skin fibroblasts, chondrocytes, osteoblasts, tenocytes, ligament fibroblasts, cardiomyocytes, smooth muscle cells, skeletal muscle cells, adipocytes, cells derived from endocrine glands, and all varieties and derivatives of neurectodermal cells.

In another embodiment, the invention provides a method further comprising:

(d) culturing the stem/progenitor cells under conditions allowing the cells to undergo clonal expansion.

The term "clonal expansion" (sometimes also referred to as "mitotic clonal expansion") relates to a process that occurs early in the differentiation program of a cell, by which stem/progenitor cells become committed to a particular lineage and then undergo terminal differentiation. It is well known in the art that the conditions to induce clonal expansion of progenitor cells may vary significantly between different cell types. Without being limited to a particular method, the induction of clonal expansion is generally achieved by cultivating the stem/progenitor cells in a medium that has been optimized for cell proliferation. Such media are commercially available from many providers. Non-limiting examples of such media are KGM®-Keratinocyte Medium (Cambrex), MEGM-Mammary Epithelial Cell Medium (Cambrex), EpiLife medium (Cascade Biologics) or Medium 171 (Cascade Biologics). Alternatively, a culture medium may be supplemented with reagents inducing cell proliferation such as growth factors. Such reagents may be admixed in a single solution such as the Human Keratinocyte Growth Supplement Kit (Cascade Biologics), to name one example, or may be supplemented individually. Such reagents include, but are not limited to, growth factors (such as epidermal growth factor, insulin-like growth factor-1, platelet-derived growth factor-BB, transforming growth factor-β1, insulin, for example), hormones (such as a bovine pituitary extract), hydrocortisone, transferrin and the like in any suitable combination to induce clonal expansion of a given cell type. The term "clonal expansion" also includes cultivation of the cell in vivo, for example, by injection of the cells into mammals such as humans, mice, rats, monkeys, apes to name only a few.

In yet another embodiment, the invention provides a method further comprising:

(e) culturing the stem/progenitor cells under conditions allowing the differentiation of said cells into epithelial cells and/or mesenchymal cells; and (f) isolating the differentiated cells.

Thus, the invention also provides for a method of differentiating a stem/progenitor cell into a differentiated cell.

In yet another embodiment, the invention provides a method, further comprising:

(g) preserving the isolated stem/progenitor cells for further use.

Methods and protocols for preserving and storing of eukaryotic cells, and in particular mammalian cells, are well known in the art (cf., for example, Pollard, J. W. and Walker, J. M. (1997) *Basic Cell Culture Protocols, Second Edition*, Humana Press, Totowa, N.J.; Freshney, R.I. (2000) *Culture of Animal Cells, Fourth Edition*, Wiley-Liss, Hoboken, N.J.). Any method maintaining the biological activity of the isolated stem/progenitor cells such as epithelial or mesenchymal stem/progenitor cells may be utilized in connection with the present invention. In one preferred embodiment, the stem/progenitor cells are maintained and stored by using cryo-preservation.

Accordingly, the invention is also directed to a progenitor/stem cell derived from the amniotic membrane of umbilical cord by means of the above methods and to a cell differentiated from the progenitor/stem cell. In addition, the invention is also directed to a cell bank comprising or consisting of one or more progenitor/stem cells that have been isolated as described here. This cell bank of progenitor/stem cells may be autologous to an individual or pooled (the latter for subsequent allogeneic transplantation, for example), and subsequently can be employed by further differentiation for regenerative medicine, tissue repair and regeneration, for example.

In accordance with the above, the invention is also directed to a pharmaceutical composition comprising a stem/progenitor cell isolated from the amniotic membrane of umbilical cord by the above inventive method. The pharmaceutical composition can also include a cell differentiated from the stem/progenitor cell. The pharmaceutical composition can be of any kind, and usually comprises the stem/progenitor cells, a cell differentiated therefrom or a cellular secretion or cellular extract thereof together with a suitable therapeutically acceptable carrier/excipient. In case of a cellular secretion, the desired compound(s) can be used in some embodiments in the form of the supernatant into which the compound(s) is/are secreted. In other embodiment, the supernatant might be processed, for example, by purification and concentration prior to be included in a pharmaceutical composition. In some embodiments, the pharmaceutical composition is adapted for systemic or topical application.

A pharmaceutical composition adapted for topical application may be in liquid or viscous form. Examples thereof include an ointment, a cream, and a lotion and the like. Examples for pharmaceutical compositions that are suitable for systemic use are liquid compositions, wherein the stem/progenitor cells or the cellular extract are dissolved in a buffer that is acceptable for injection or infusion, for example. The preparation of such pharmaceutical compositions is within the knowledge of the person skilled in the art and described in Gennaro, A. L. and Gennaro, A. R. (2000) *Remington: The Science and Practice of Pharmacy*, 20th Ed., Lippincott Williams & Wilkins, Philadelphia, Pa., for example.

Accordingly, the invention also relates to a method of treating a subject having a disorder. This method comprises administering to the subject an effective amount either of a stem/progenitor cell isolated as explained herein or of a cellular extract derived from such a cell.

In principle, any condition or disorder which is suitable for being treated by means of stem cells/progenitor cells can be treated with a cell or a cellular extract of present invention. It is also possible to differentiate cells of the invention into a desired type of cell, for example, but not limited to, a skin cell, a bone cell, an hormone producing cell such as a beta islet insulin producing cell, and use the differentiated cell therapeutically. In some embodiments, the disorder is selected from the group consisting of neoplastic disease, accelerated skin aging and skin disorders, tissue disorders, visceral endocrine deficiencies, and neural disorders.

The tissue disorder to be treated can be a congenital or an acquired tissue deficiency. Examples of visceral endocrine deficiency that can be treated with a cell of the invention include, but are not limited to, Diabetes mellitus associated with insulin deficiency, testosterone deficiency, anemia, hypoglycemia, hyperglycemia, pancreatic deficiency, adrenal deficiency, and thyroid deficiencies.

Examples of neural disorders that can be treated include, but are not limited to, Alzheimer's disease, Parkinson's disease, Jacob Kreutzfeld's disease, Lou Gehrig's disease, Huntington's disease and neural neoplastic conditions.

An example of a skin disease is a wound or a damaged part of the skin, for example, sun burned skin. Also aging of the skin is considered to be a skin disease herein. Topical or similar delivery of stem/progenitor cells of the invention or cellular extracts thereof, for example, as a constituent in lotions or creams or any other suitable vehicle may thus be used for repair of sun damaged skin and in addition may slow also down the aging process of skin (anti-aging properties) by replenishing, and thus fortifying, deficient growth factors and related peptide elements, without which skin aging would be accelerated. The stem/progenitor cells may also migrate to injured regions of the body such as surface wounds to form the necessary required cellular elements necessary for the local reparative processes (cf. *The Journal of Immunology*, 2001, 166: 7556-7562; or *International Journal of Biochemical and Cell Biology* 2004; 36: 598-606.

The neoplastic disease may be cancer, in particular as recent studies have demonstrated that stem cells may selectively target neoplastic tumor tissue (*Journal of the National Cancer Institute* 2004; 96 (21): 1593-1603) allowing for directed delivery of antineoplastic agents such as interferon to neoplastic foci. The cancer can be any kind of cancer, including those cancers that are able to form solid tumors, ranging from skin cancer to cancer of the internal organs. Examples of cancers to be treaded include, squamous cell carcinoma, breast ductal and lobular carcinoma, hepatocellular carcinoma, nasopharyngeal carcinoma, lung cancer, bone cancer, pancreatic cancer, skin cancer, cancer of the head or neck, cutaneous or intraocular malignant melanoma, uterine cancer, ovarian cancer, rectal cancer, cancer of the anal region, stomach cancer, colon cancer, breast cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemias, solid tumors of childhood, lymphocytic lymphoma, cancer of the bladder, cancer of the kidney or ureter, renal cell carcinoma, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer or any combination of such cancers, including disseminated (metastasising) forms thereof. In case of treatment of a neoplastic disease the umbilical cord amnion derived stem cells and/or their cellular extracts disclosed herein can be administered systemically both as a direct treatment and/or as a carrier vehicle. In the latter case of anti-neoplastic tumor therapy, the cells comprise an anti-neoplastic agent.

In another pharmaceutical use, stem/progenitor cells of the present invention can be used for gene therapy. For this purpose, the cells can be transformed with a nucleic acid encoding the protein that is to be produced in the cells. The nucleic acid can be introduced into a cells of the invention using any of the various methods that are well known to the skilled person, for example, using a viral vector and/or a lipid containing transfection composition such as as IBAfect (IBA GmbH, Göttingen, Germany), Fugene (Roche), GenePorter (Gene Therapy Systems), Lipofectamine (Invitrogen), Superfect (Qiagen), Metafecten (Biontex) or those ones described in the PCT application WO 01/015755). In a related embodiment, the cells of the invention, after being transformed with a nucleic acid encoding a polypeptide of choice, can be used of recombinantly producing this polypeptide.

As mentioned above, stem cell extracts are rich in a variety of growth factors and peptides that are relevant for normal tissue physiology. Such growth factors and/or peptides may be deficient in exposed parts of the body, such as the skin, which is the surface layer of all human beings protecting the body from external elements for the maintenance of internal homeostasis. Therefore in a further embodiment, stem/progenitor cells of the invention or cellular extracts thereof are suitable for the treatment and/or maintenance of internal homeostasis.

In a further embodiment and in line with the above disclosure, the stem/progenitor cells of the invention can be used for the production of any biological molecule. The biological molecule can be, for instance, any molecule that is naturally produced in the cells or a molecule the coding nucleic acid of which has been introduced into the cells via recombinant DNA technology. Examples of molecules that can be produced by the cells of the invention include, but are not limited to, a protein such as a cytokine, a growth factor such as insulin-like growth factor (IGF), epidermal growth factor (EGF), transforming growth factor beta (TGF-beta), Activin A, a bone morphogenetic protein (BMP), PDGF or a hormone as insulin or erythropoietin or a transporter protein such transferrin, a peptide such a growth factor or hormone (e.g. luteinic hormone (LSH), follicle stimulating hormone (FSH)), a small organic molecule such as a steroid hormone, an oligo- or polysaccharide, for example, heparin or heparan sulfate (cf., example WO 96/23003, or WO 96/02259 in this regard), a proteoglycan, a glycoprotein such as collagen or laminin, or a lipid, to name only a few.

In a further aspect and in accordance with recent approaches (see, for example, Amit, M et al., Human feeder layers for human embryonic stell cells, Biol Reprod 2003; 68: 2150-2156), the stem/progenitor cells described here can be used as feeder layer for the cultivation of other embryonic stem cells, in particular human embryonic stem cells. In one of these embodiments the cells of the present invention are preferably of human origin, since using human cells as feeder layer minimizes the risk of contaminating the cell culture with animal-derived components such as animal pathogens or immunogens. In this respect, it is to be noted that the cells of the invention can be cultivated under serum free conditions. Accordingly, employing the cells as feeder layer and cultivating the cell culture under with serum free media as the one described herein later, or in Draper et al. (Culture and characterization of human embryonic stem cell lines, Stem Cells Dev 2004, 13:325-336) or in the International patent application WO 98/30679, for example.

Figures 1, 9:
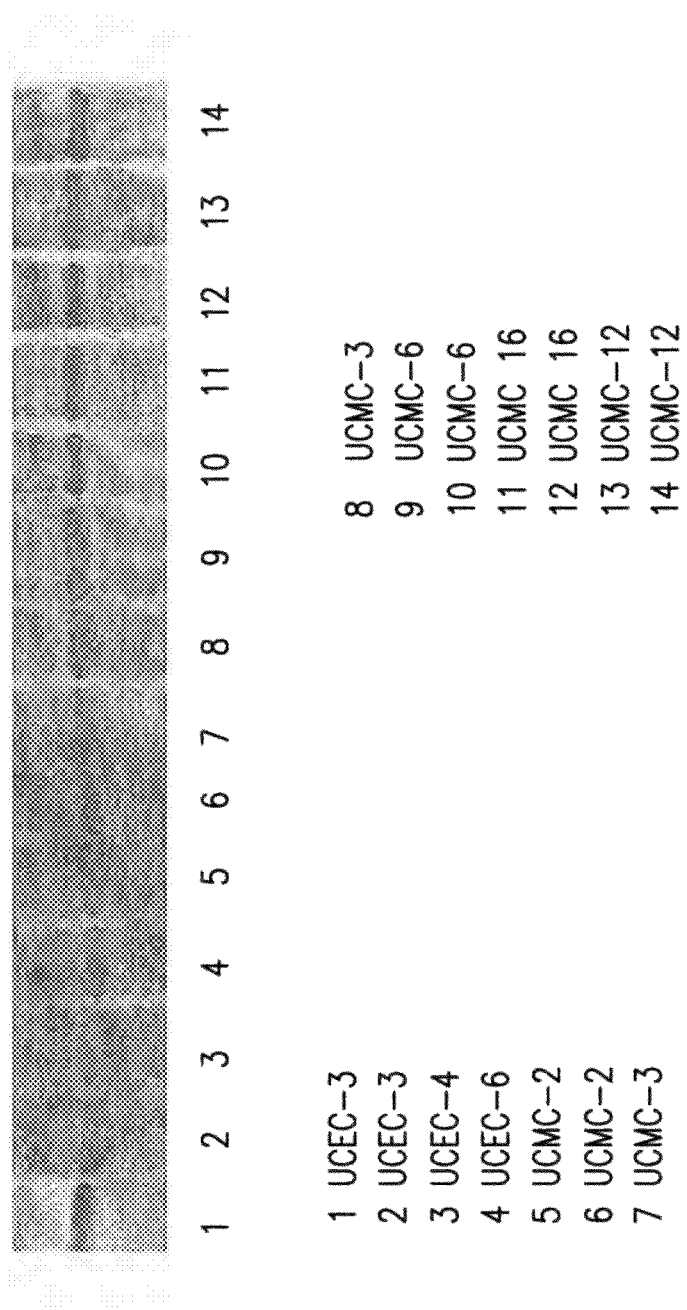
FIG. 9-1 to FIG. 9-28 show Western blot analysis by which the expression of several embryonic stem cell markers in UCEC and UCMC isolated according to the invention, was compared to the expression of these markers in human dermal fibroblasts (NF), in bone marrow mesenchymal cells (BMSC) and adipose-derived mesenchymal cells (ADMC). In more detail, FIG. 9.1 shows expression of Oct-4, FIG. 9-2 and FIG. 9-3 both show expression of STAT3, FIG. 9-4 and FIG. 9-5 both show expression of placenta-like growth factor PLGF), FIG. 9-6 and FIG. 9-7 both expression of connective tissue growth factor (CTGF), FIG. 9-8 and FIG. 9-9 both show expression of Platelet-derived Growth Factor (PDGF), FIG. 9-10 and FIG. 9-11 both show expression of vascular endothelial growth factor (VEGF), FIG. 9-12 and FIG. 9-13 both show expression of Fibroblast Growth Factor-2 (FGF-2), FIG. 9-14 and FIG. 9-15 both show expression of Hepatoma-derived Growth Factor (HDGF)
Figures 4, 9:
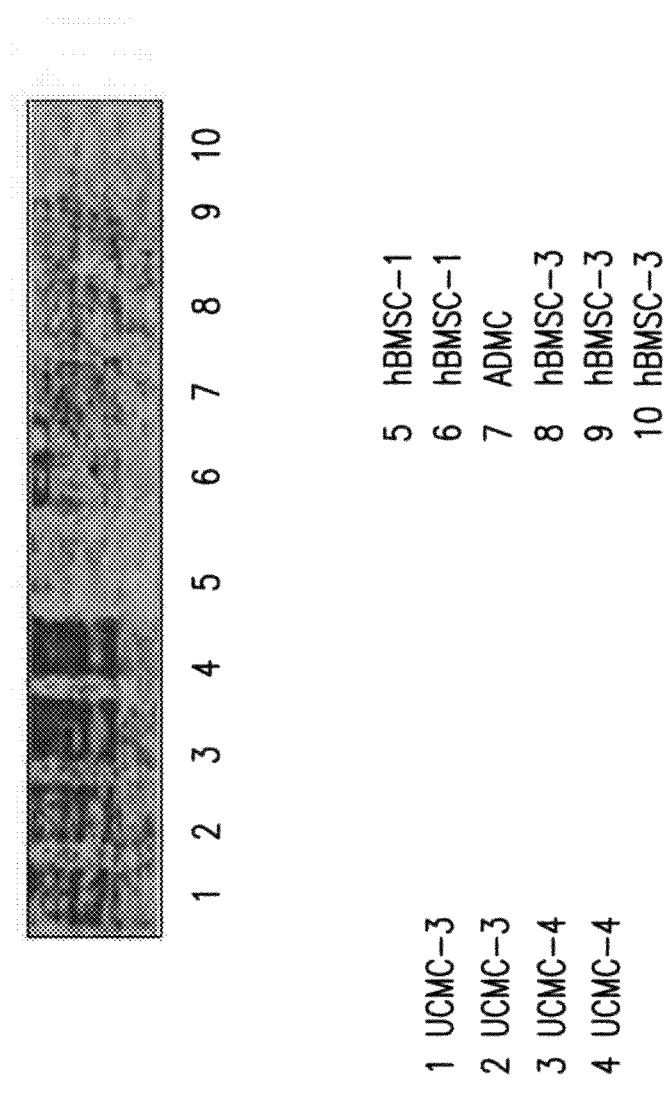
Figures 6, 9:
Figures 7, 9:
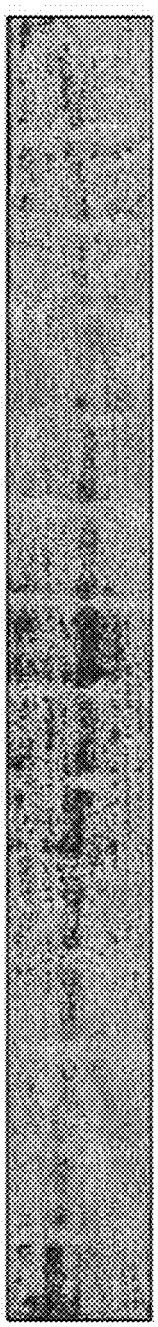
Figures 8, 9:
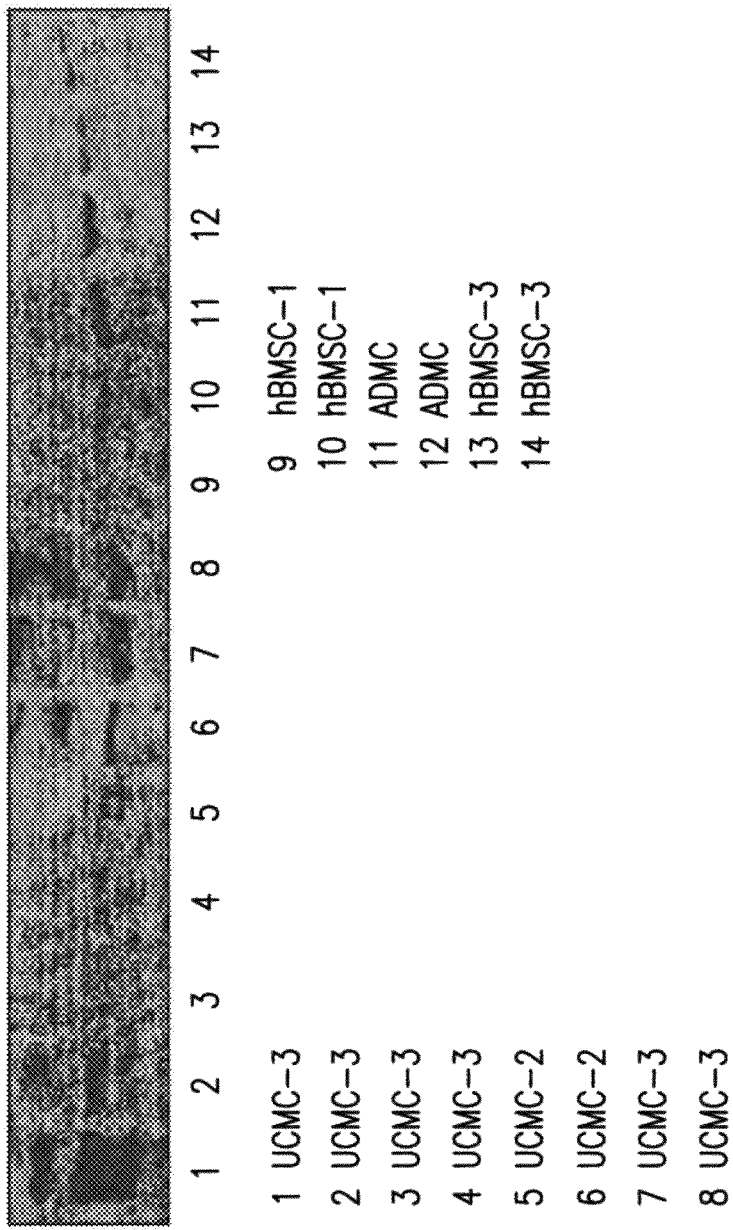
Figure 9:
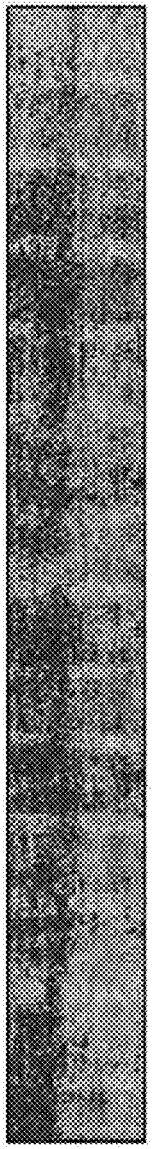
Figures 9, 10:
Figures 9, 10, 11:
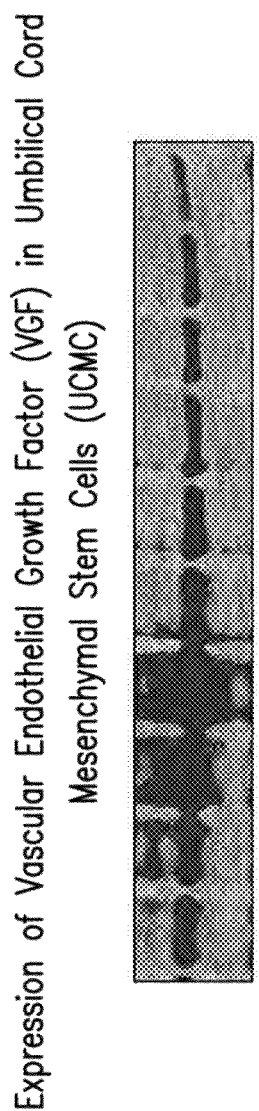
Figures 9, 10, 11, 12:
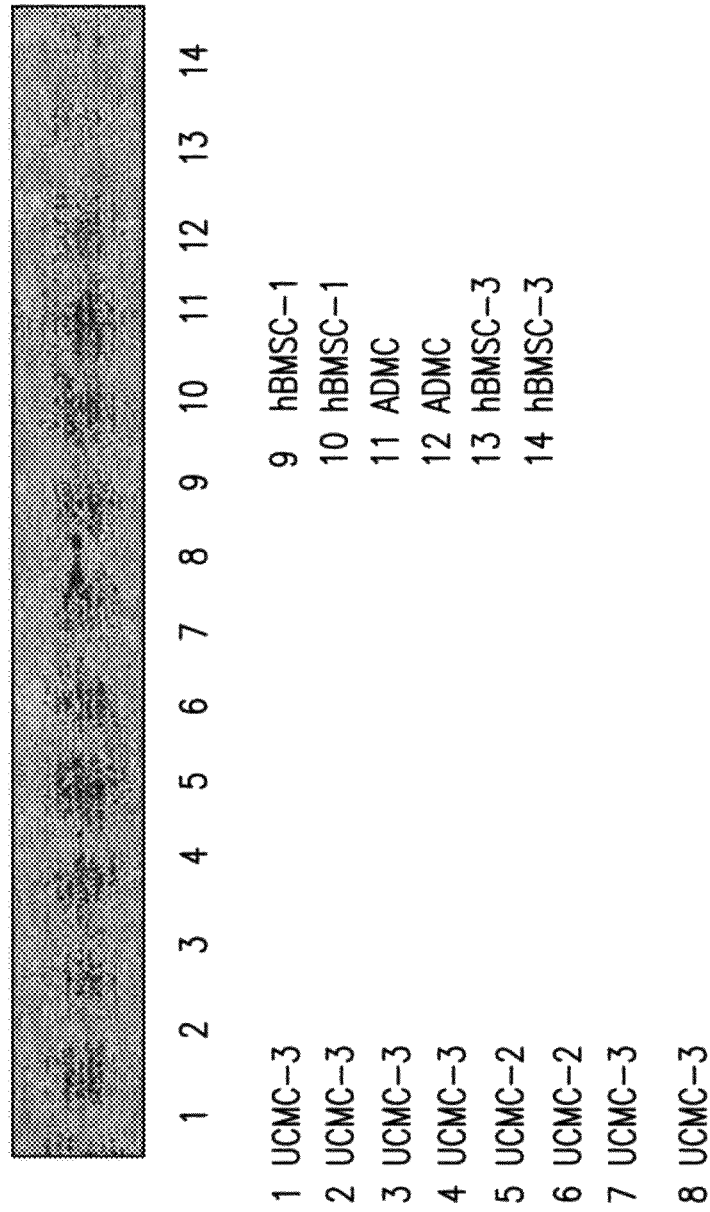
Figures 9, 10, 11, 12, 13:
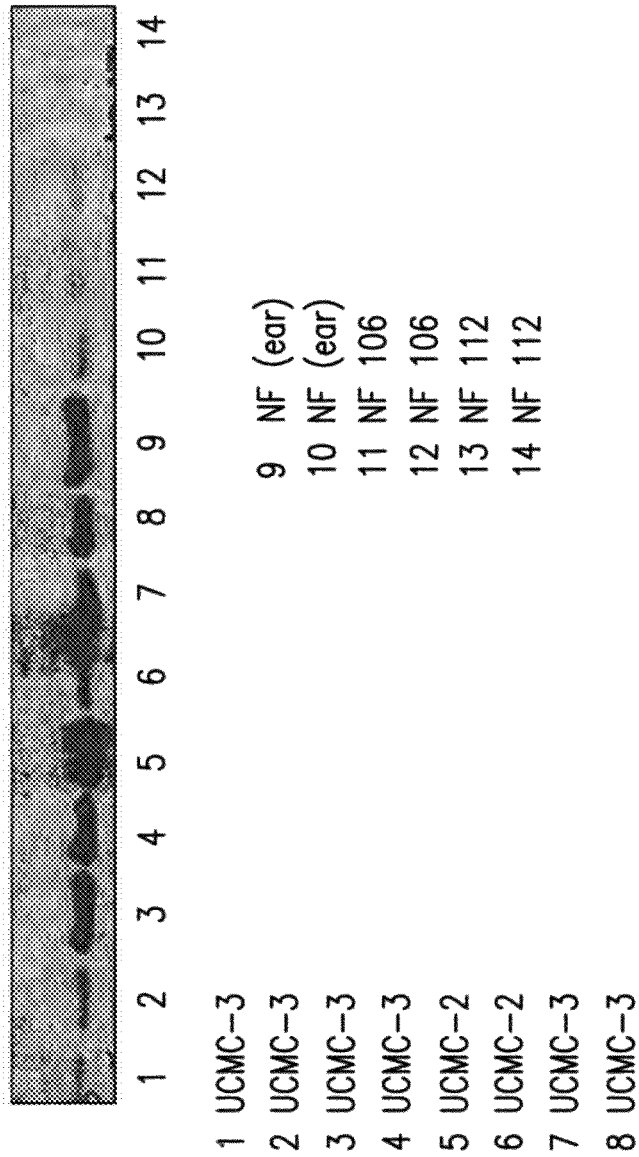
Figures 9, 10, 11, 12, 13, 14:
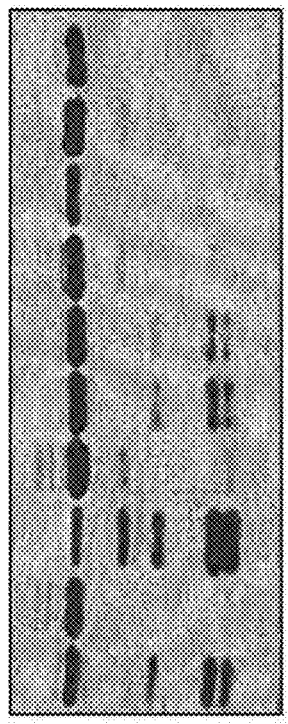
Figures 9, 10, 11, 12, 13, 14, 15:
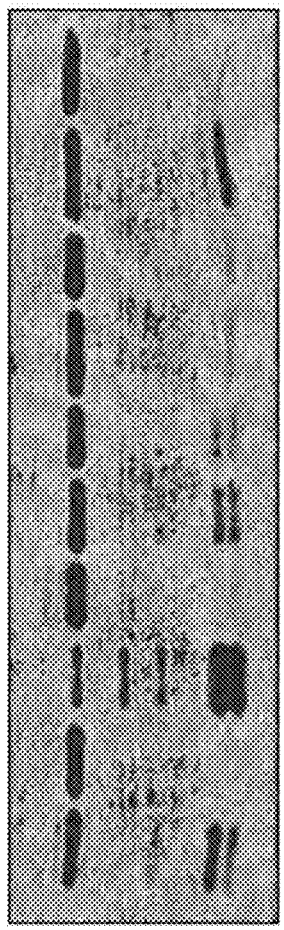

In this connection, it is noted that in transplantation surgery and cell-based therapy high quantities of low passage cells with a minimal proportion of senescent cells (i.e., large proportion of high quality cells) are crucial and are required to be derived within the shortest possible time during cell expansion. For example, mesenchymal stem cells from bone marrow and cord blood are low in quantity and therefore require expansion over many passages for a long period of time in order to achieve the sufficient number of cells required for cell transplant. The high passage cells however tend to deteriorate in quality and may lead to cell senescence or cancerous transformation. It has been found here that high quantities of cells of the present invention can be obtained by low passage numbers using a repetitive explanation technique. The present invention thus also relates to a method of cultivating stem/progenitors cells of the invention, wherein this method comprises:

Obtaining a tissue explant from the amniotic membrane of umbilical cord;

Cultivating the tissue explant in suitable cultivation media and cultivation conditions over a suitable period of time, Optionally exposing the tissue explant to fresh cultivation media and continuing the cultivation under suitable conditions over a suitable period of time (cf., FIG. 15).

The cultivation can be carried out in for as many cycles (passages) as wanted and be stopped once the desired number of cells has been obtained. Exposing the tissue explant to fresh cultivation can be carried out by removing the used cell cultivation medium from the vessel used for growing the cells and adding fresh media to that vessel. Instead of replacing the media in the used vessel, exposing to fresh cultivation media can be achieved by transferring the tissue explant to a new vessel which is filled with cultivation media. The tissue explant used for cultivation/propagation of the cells can be obtained by any suitable method, for example by the "direct tissue explant technique" as explained above (in which the tissue is first placed in media without enzymes, and then under careful conditions the cells separate from the main tissue mass by itself- and the cells are then harvested for collection).

The cultivation of the tissue explants can be carried out in any media that is suitable for cultivation of mammalian cells. Examples include the conventional and commercially available media that are given above with respect to the cultivation or the clonal expansion of the cells of the invention such as, but not limited to, KGM®-Keratinocyte Medium (Cambrex), MEGM-Mammary Epithelial Cell Medium (Cambrex) EpiLife medium (Cascade Biologics), Medium 171 (Cascade Biologics), DMEM, DMEM-F12 or RPMI media. The cultivation is typically carried out at conditions (temperature, atmosphere) that are normally used for cultivation of cells of the species of which the cells are derived, for example, at 37° C. in air atmosphere with 5% $CO_2$. In one embodiment, the cultivation is carried out using serum free, in particular bovine serum free media. The cultivation (in one passage) is performed for any suitable time the cells need for growth, typically, but by no means limited to, for about 1 to several days, for example to about 7 or about 8 days.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXAMPLES

Example 1

Collection of Umbilical Cord Tissue

Umbilical cord tissue is collected immediately after delivery of the child. The specimen is rinsed clean and immediately transferred into a 500 ml sterile glass bottle containing culture transport medium (L-15 medium supplemented with 50 IU/ml penicillin, 50 µg/ml streptomycin, 250 µg/ml fungizone, 50 µg/ml gentamicin; all reagents purchased from Invitrogen) prior to transport to the laboratory. In the laboratory, stem cell extraction is conducted in a laminar flow hood under sterile conditions. The specimen is first transferred to a sterile stainless steel tray. All remaining blood in the cord vessels is removed by multiple syringing washes using warm phosphate-buffered saline (PBS) supplemented with 5 IU/ml heparin (from Sigma). Plain PBS without heparin is used in the final washes. The umbilical cord tissue specimen is then cut into pieces 2 cm in length and transferred into 10 cm diameter cell culture dishes, where further washing and disinfection is performed with 70% ethanol followed by multiple washes using PBS containing an antibiotic mixture (50 IU/ml penicillin, 50 µg/ml streptomycin, 250 µg/ml fungizone, 50 µg/ml gentamicin; all purchased from Invitrogen) until the solution becomes clear.

Example 2

Cell Separation/cultivation

Dissection of umbilical cord tissue is first performed to separate the umbilical cord amniotic membrane from Wharton's jelly (i.e. the matrix of umbilical cord) and other internal components. The isolated amniotic membrane is then cut into small pieces (0.5 cm×0.5 cm) for cell isolation. Explant is performed by placing the pieces of umbilical cord amniotic membrane on tissue culture dishes at different cell culture conditions for isolation of either epithelial or mesenchymal stem cells.

For mesenchymal cell separation/cultivation, the explants were submerged in 5 ml DMEM (Invitrogen) supplemented with 10% fetal bovine serum (Hyclone) (DMEM/10% FBS) and maintained in a $CO_2$ cell culture incubator at 37° C. The medium was changed every 2 or 3 days. Cell outgrowth was monitored under light microscopy. Outgrowing cells were harvested by trypsinization (0.125% trypsin/0.05% EDTA) for further expansion and cryo-preservation using DMEM/10% FBS.

For epithelial cell separation/cultivation, cell culture plastic surfaces were coated with collagen 1/collagen 4 mixtures (1:2) before placing the tissue samples on the surface. The tissue samples were submerged in 5 ml EpiLife medium or Medium 171 (both from Cascade Biologics). The medium was changed every 2 or 3 days. Cell outgrowth from tissue culture explants was monitored under light microscopy. Outgrowing cells were harvested by trypsinization (0.125% trypsin/0.05% EDTA) using EpiLife medium or Medium 171.

For the enzymatic extraction method of cells, umbilical cord amniotic membrane was divided into small pieces of 0.5 cm×0.5 cm and digested in 0.1% (w/v) collagenase type1 solution (Roche Diagnostics) at 37° C. for 6 hours. The samples were vortexed every 15 min for 2 min. Cells were harvested by centrifugation at 4000 rpm for 30 min. Two different approaches were employed to isolate either epithelial or mesenchymal stem cells.

For isolation of epithelial stem cells, cell pellets were resuspended in EpiLife medium or Medium 171 (both from Cascade Biologics) supplemented with 50 µg/ml insulin-like growth factor-1 (IGF-1), 50 µg/ml platelet-derived growth factor-BB (PDGF-BB), 5 µg/ml transforming growth factor-β1 (TGF-β1), and 5 µg/ml insulin (all obtained from R&D Systems), counted and seeded on 10 cm tissue culture dishes pre-coated with collagen 1/collagen 4 mixtures (1:2; Becton Dickinson) at density of $1\times10^6$ cells/dish. After 24 hours, attached cells were washed with warm PBS and medium was replaced with supplement-added EpiLife medium or Medium 171. The medium was changed every 2 or 3 days. Cell growth and expanding clonal formation was monitored under light microscopy. At a confluence of about 70%, cells were sub-cultured by trypsinization (0.125% trypsin/0.05% EDTA) for further expansion and cryo-preservation.

For isolation of mesenchymal stem cells, cell pellets were resuspended in DMEM/10% FBS, counted and seeded on 10 cm tissue culture dishes at density of $1\times10^6$ cells/dish. The culture medium was changed every 2 or 3 days. Cell growth and expansion was monitored under light microscopy. At a confluence of about 90%, cells were sub-cultured as outlined above.

For cultivation of epithelial and mesenchymal stem cells on feeder layer, umbilical cord lining membrane was digested by collagenase treatment, counted and seeded on 10 cm tissue culture dishes coated with lethally irradiated or Mitomycin C treated 3T3 fibroblasts (feeder layer) in Green's medium. The culture medium was changed every 2 or 3 days. Colony formation was monitored under light microscopy and photographed.

Example 3

Identification of Stem/progenitor Cells

Figure 1C:
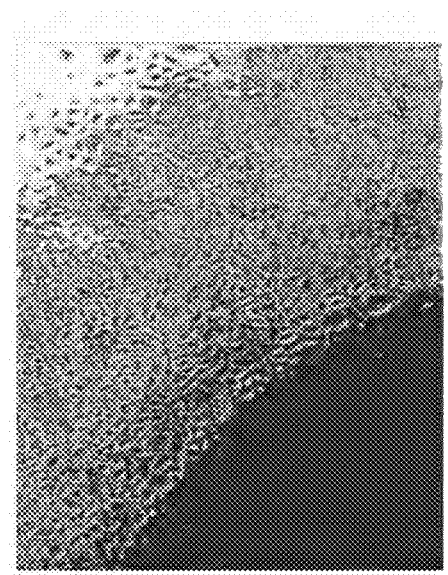
FIG. 1B and FIG. 1C show epithelial cell outgrowth of the tissue culture at day 5. Cell culture plastic surfaces were coated with collagen 1/collagen 4 mixtures (1:2; Becton Dickinson) before placing the amniotic membrane on the surface. The amniotic membrane specimens were submerged in 5 ml EpiLife medium or Medium 171 (both from Cascade Biologics). Medium was changed every 2 or 3 days and cell outgrowth by explant was monitored under light microscopy. Microphotographs were taken at different time intervals as stated above. The observed polyhedral cell morphology is typical of epithelial cells.
Figure 1B:
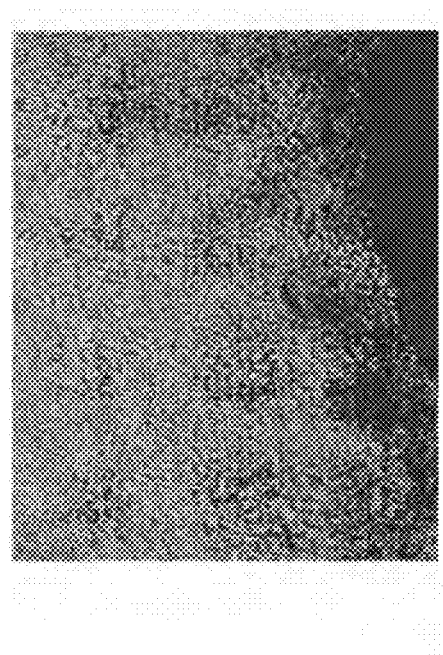
Figure 2B:
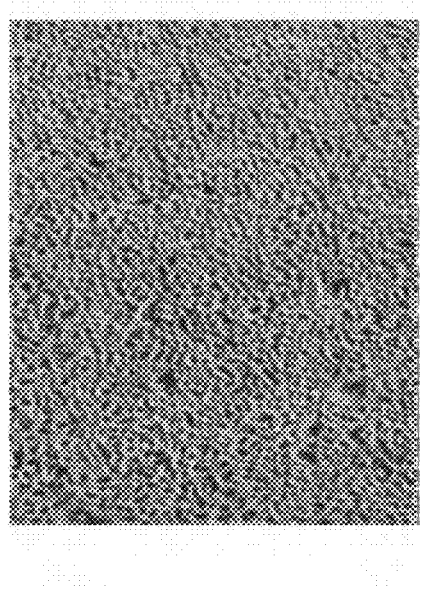
FIG. 2B and FIG. 2D depict this enzymatic digestion of the umbilical cord segments at day 5. Umbilical cord amniotic membrane was divided into small pieces of 0.5 cm×0.5 cm and digested in 0.1% (w/v) collagenase type 1 solution (Roche Diagnostics) at 37° C. for 8 hours. The samples were vortexed every 30 min for 3 min. Cells were harvested by centrifugation at 4000 rpm for 30 min. Cell pellets were resuspended in EpiLife medium or Medium 171 (both from Cascade Biologics) supplemented with 50 µg/ml insulin-like growth factor-1 (IGF-1), 50 µg/ml platelet-derived growth factor-BB (PDGF-BB), 5 µg/ml transforming growth factor-β1 (TGF-β1) and 5 µg/ml insulin (all obtained from R&D Systems), counted and seeded on 10 cm tissue culture dishes pre-coated with collagen 1/collagen 4 mixtures (1:2; Becton Dickinson) at density of 1×10$^6$ cells/dish. After 24 hours, attached cells were washed with warm phosphate buffered saline (PBS) and the culture medium was replaced with EpiLife medium or Medium 171 (both from Cascade Biologics). The medium was changed every 2 or 3 days, and cell outgrowth was monitored under light microscopy. Microphotographs were taken at different time intervals as stated above. Once again the cells demonstrated typical epithelial cell polyhedral morphology.
Figure 2D:
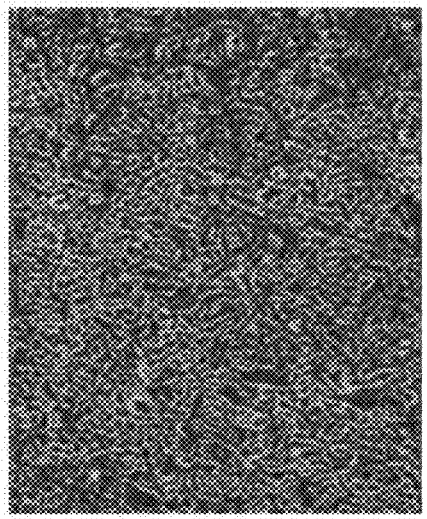
Figure 2A:
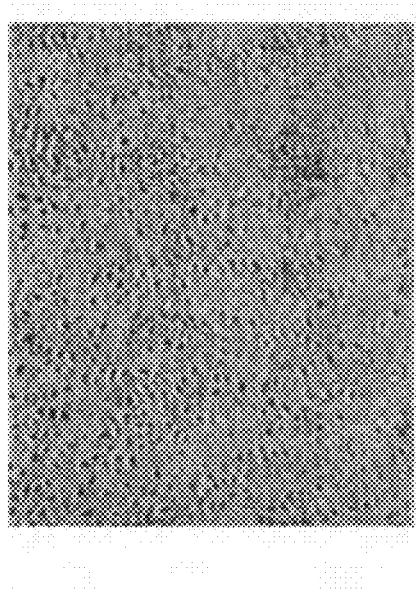
Figure 2C:
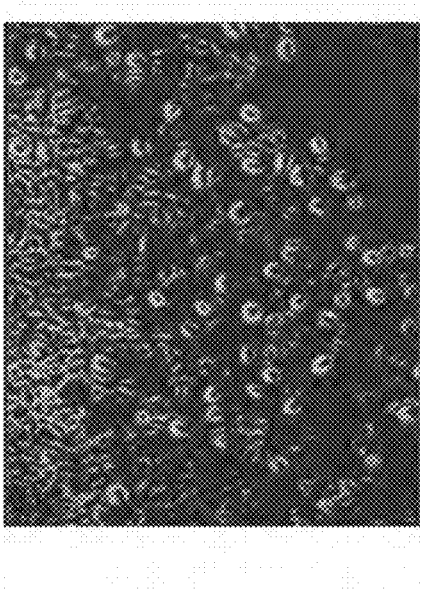
Figure 7:
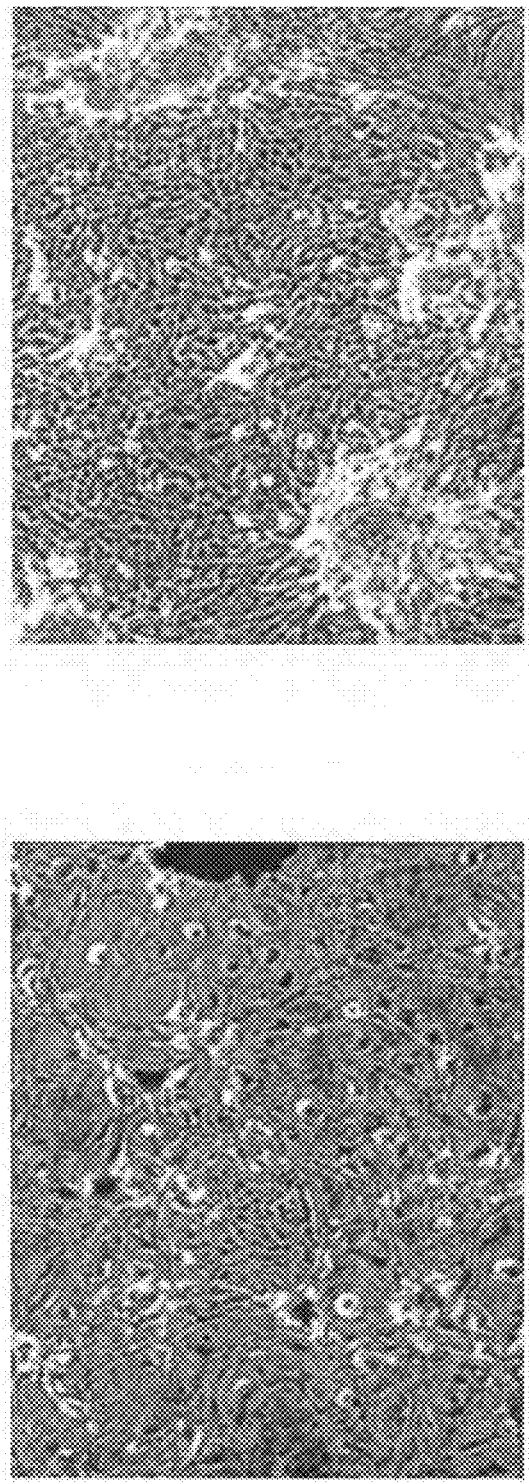
FIG. 7 (40× magnification) depicts colony formation of umbilical cord epithelial cells (UCEC) cultured on a 3T3 feeder layer at days 3 and 7. This appearance is similar to that of normal skin derived epithelial keratinocyte stem cells. In the latter, the 3T3 feeder layer maintains stemness of the cells.
Figure 8A:
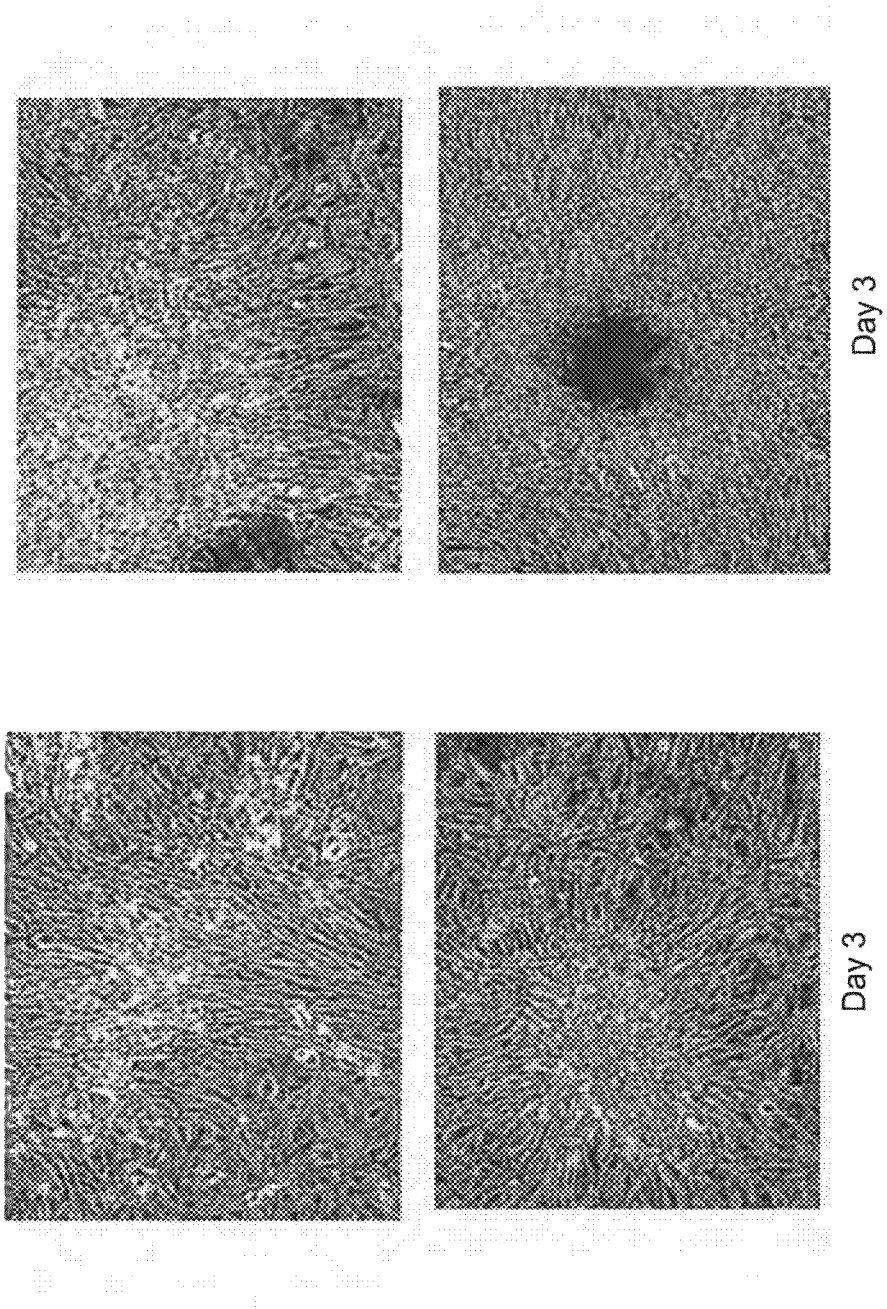
FIG. 8-A depicts obvious colony formation of umbilical cord mesenchymal cells (UCMC) isolated according to the invention cultured on a 3T3 feeder layer at days 3 and 7. The 3T3 feeder layer normally suppresses the growth of differentiated mesenchymal cells as human dermal fibroblasts. Once again, this indicates a difference in behavior of these mesenchymal cells as compared to their more differentiated counterparts.
Figure 8B:
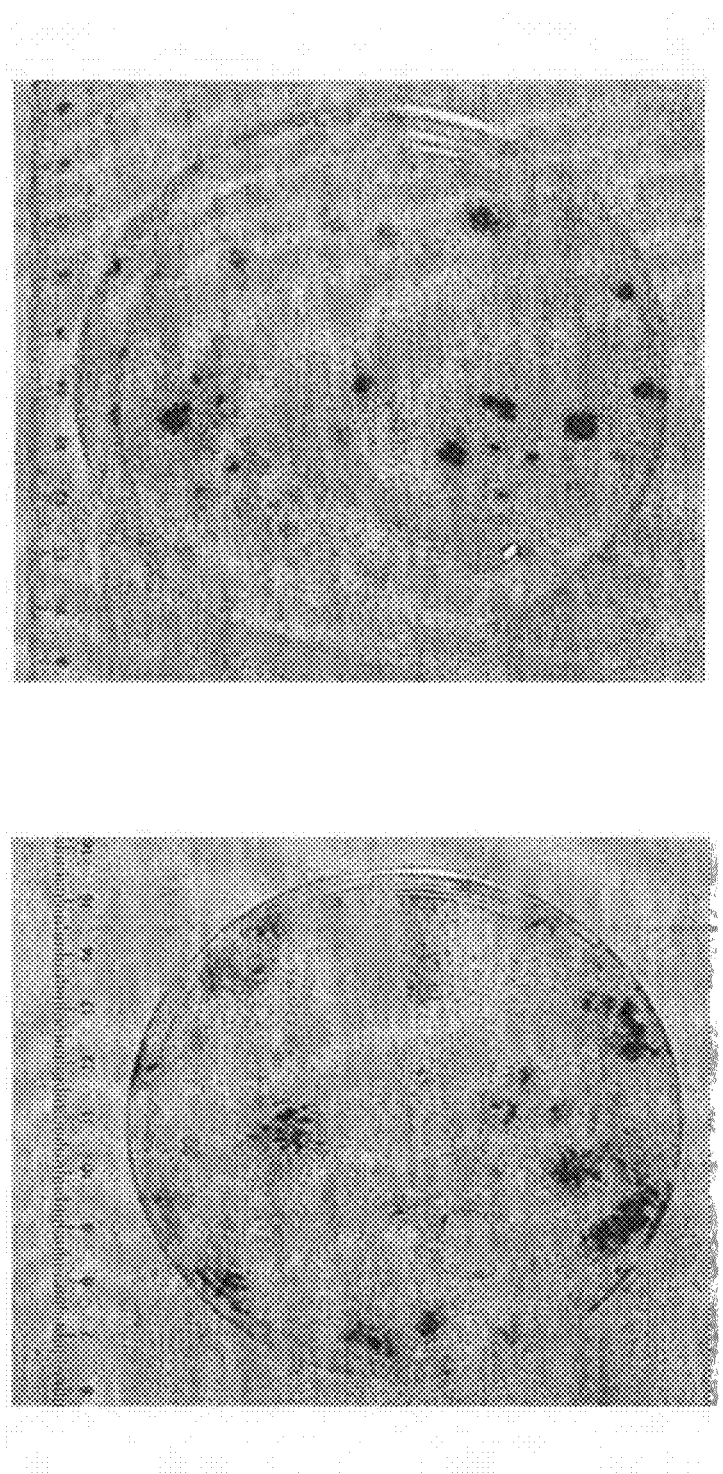

Epithelial Cells: FIG. 1A to FIG. 1C shows pictures of outgrowing epithelial cells from umbilical cord amniotic membrane prepared by the method using tissue explant (40× magnification). Pictures were taken at day 2 (FIG. 1A) and day 5 (FIG. 1B and FIG. 1C) of tissue culture. Cell morphology analysis demonstrated polyhedral shaped epithelial-like cells. Enzymatic digestion of the umbilical cord segments yielded similar (FIG. 2A to FIG. 2D), epithelial cells at day 2 (FIG. 2A and FIG. 2C) and day 5 (FIGS. 2B and 2D) (40× magnification). FIG. 7 shows pictures of colony formation of epithelial stem cells from umbilical cord amniotic membrane cultured on feeder layer using Green's method (40× magnification). A colony of polyhedral shaped epithelial-like cells expanded rapidly from day 3 to day 7.

Figure 3A:
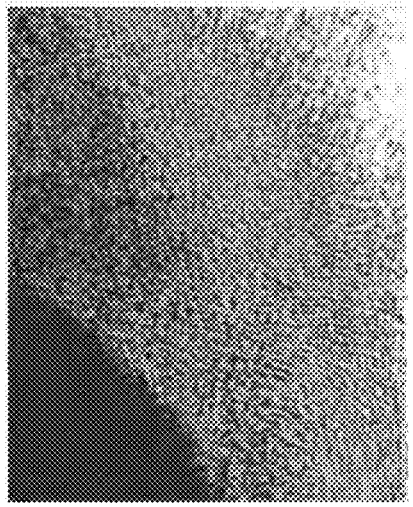
FIG. 3A to FIG. 3D depict outgrowing mesenchymal cells explanted from umbilical cord amniotic membrane.
Figure 3B:
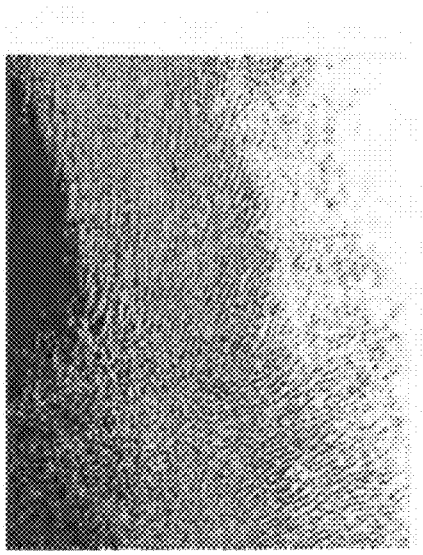
Figure 3C:
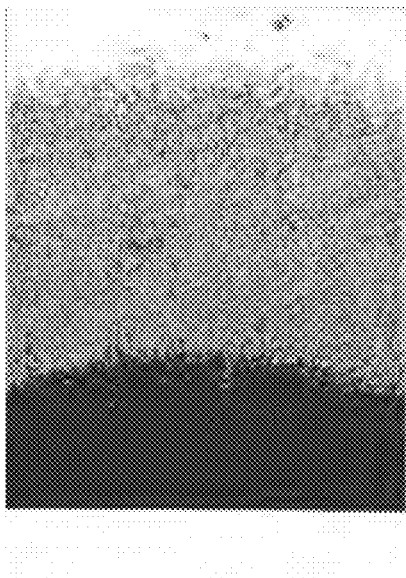
Figure 3D:
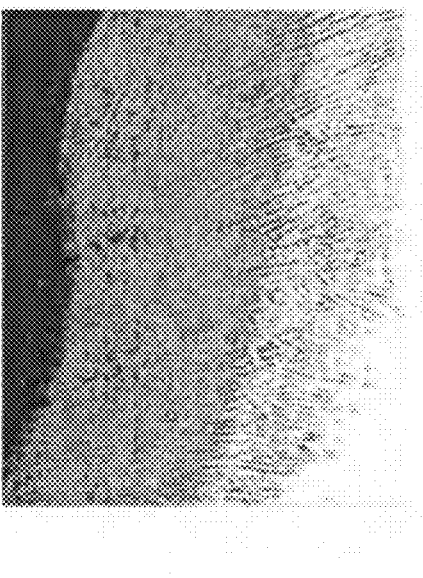
Figure 5F:
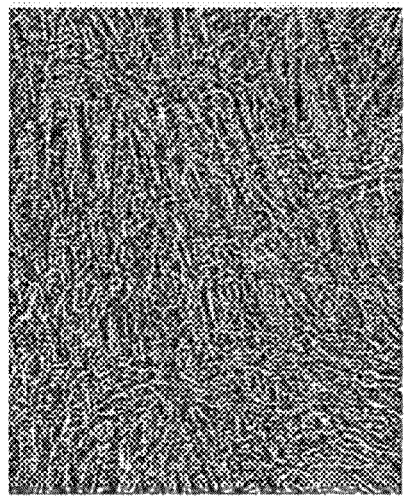
Figure 5H:
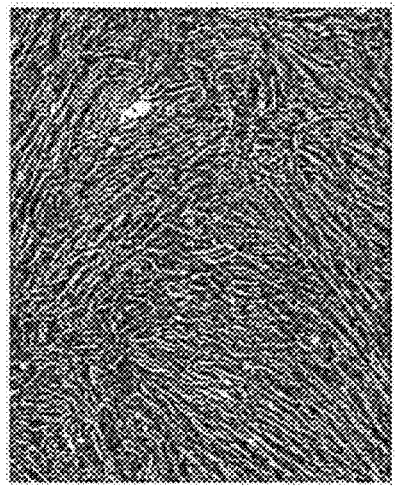
Figure 5E:
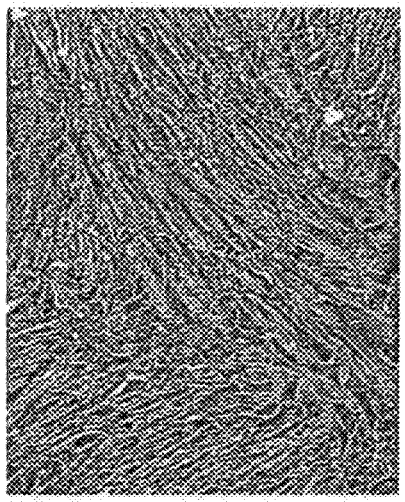
Figure 5G:
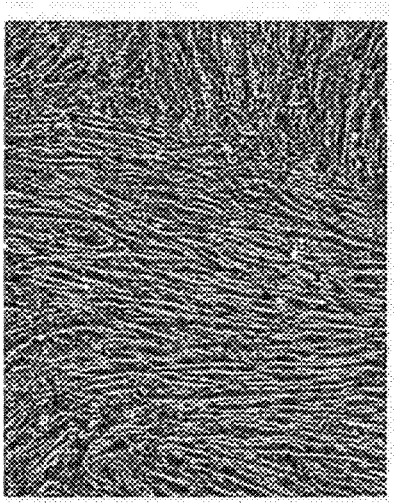
Figure 6:
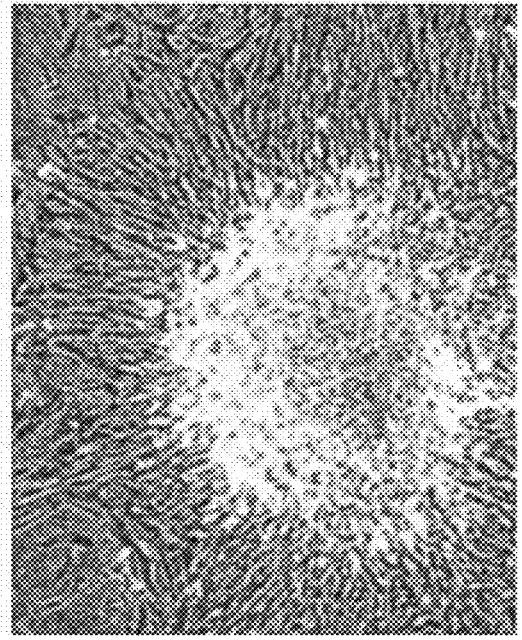
FIG. 6 (40× magnification) depicts UCMC isolated according to the invention cultured in DMEM/10% FCS at days 3 and 7 without a 3T3 feeder layer. The cells are seen to be growing well, and are forming a colony (vertical growth) instead of exhibiting radial spread. Once again, this indicates a difference in behavior of these mesenchymal cells as compared to their more differentiated counterparts.
Figure 6:
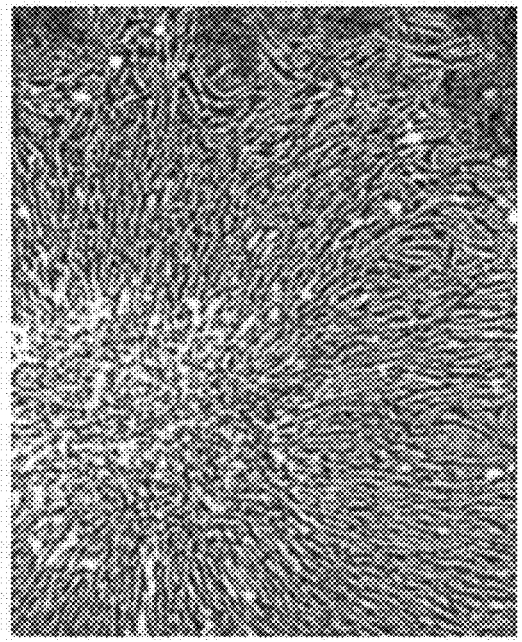

Mesenchymal Cells: Outgrowth of mesenchymal cells explanted from umbilical cord amniotic membrane was observed as early as 48 hours after placement in tissue culture dishes using DMEM supplemented with 10% fetal calf serum (FCS) as culture medium (FIG. 3A and FIG. 3C) (40× magnification). The cells were characterized by their spindle shaped morphology, and migrated and expanded both easily and quickly in vitro, closely resembling fibroblasts (FIG. 3B and FIG. 3D) (40× magnification). Similar observations were noted in the cell group isolated by collagenase enzymatic digestion (FIG. 4A and FIG. 4B). FIG. 4A shows mesenchymal cells isolated from umbilical cord amniotic membrane at day 2. Cell proliferation was observed at day 5 (FIG. 4B) (40× magnification). FIG. 6 and FIG. 8-A show pictures of colony formation of mesenchymal stem cells from umbilical cord amniotic membrane cultured on non-feeder layer (FIG. 6) and feeder layer condition (FIG. 8-A, using a 3T3 feeder layer) in DMEM/10% FCS (40× magnification). The colonies of elongated shaped fibroblastic-like cells expanded rapidly from day 3 to day 7. It is noted in this respect, that the 3T3 feeder layer normally suppresses the growth of mesenchymal cells as human dermal fibroblasts. Once again, this indicates a difference in the behavior of the mesenchymal cells of the invention as compared to more differentiated counterparts.

In further experiments the colony forming ability of the mesenchymal cells of the invention (UCMC) was studied. For colony forming efficiency assay, 100-200 single cells were seeded in 100 mm tissue culture dishes or T75 flasks without feeder layers. Cells were maintained in DMEM/10% FCS for 12 days. Single colony formation was monitored under the inverted light microscope (experiment was carried out in duplicate, experiments termed UCMC-16 and UCMC-17 in FIG. 8-B). Microphotographs were sequentially taken. At day 12, colonies were fixed and stained with Rhodamine. UCMC colony forming units were seen (FIG. 8-B). The multiple large colonies observed, indicated self-renewal of UMCM in-vitro (FIG. 8-B).

Figures 1, 10:
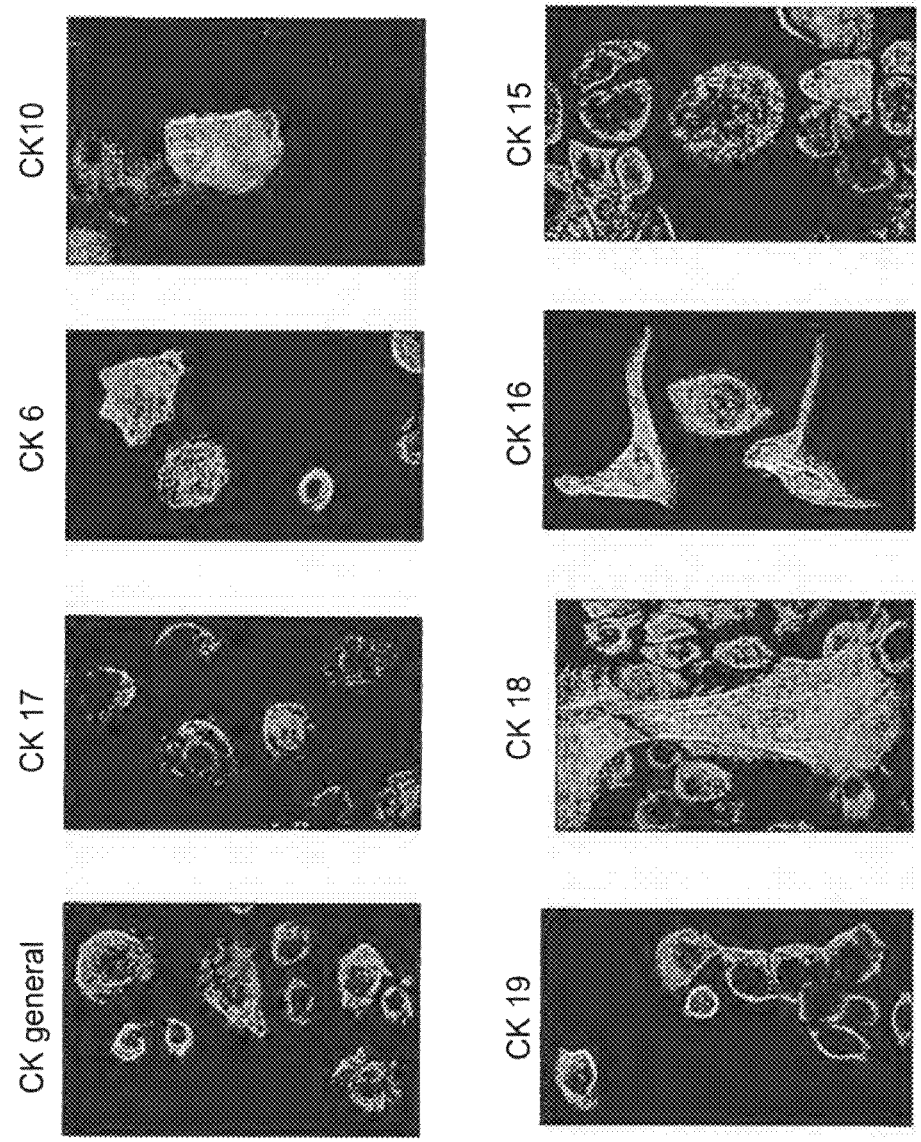
Figures 3, 10:
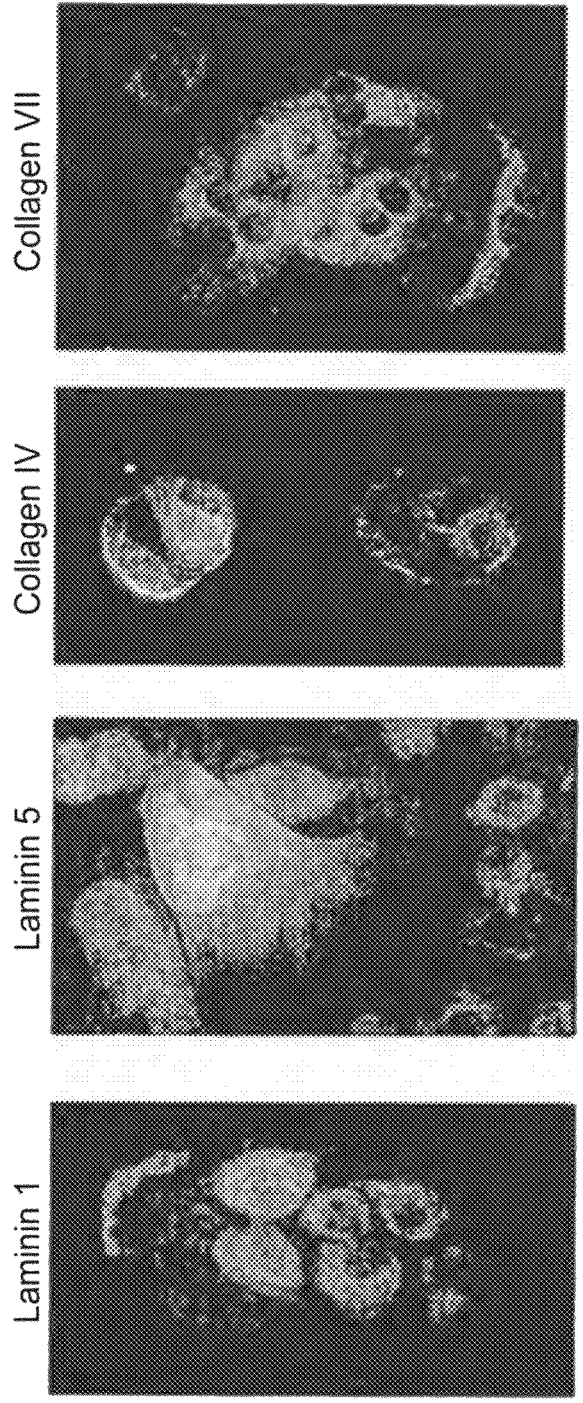
Figures 4, 10:
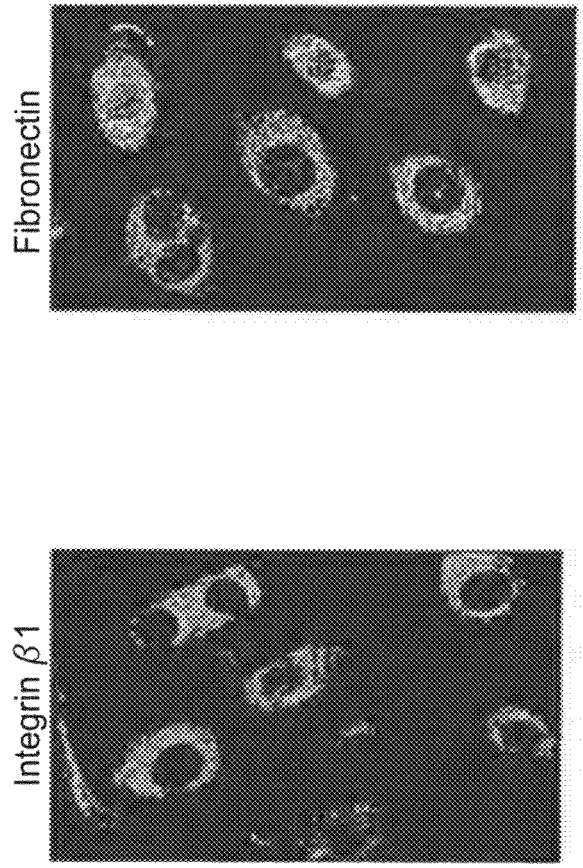
Figures 1, 11:
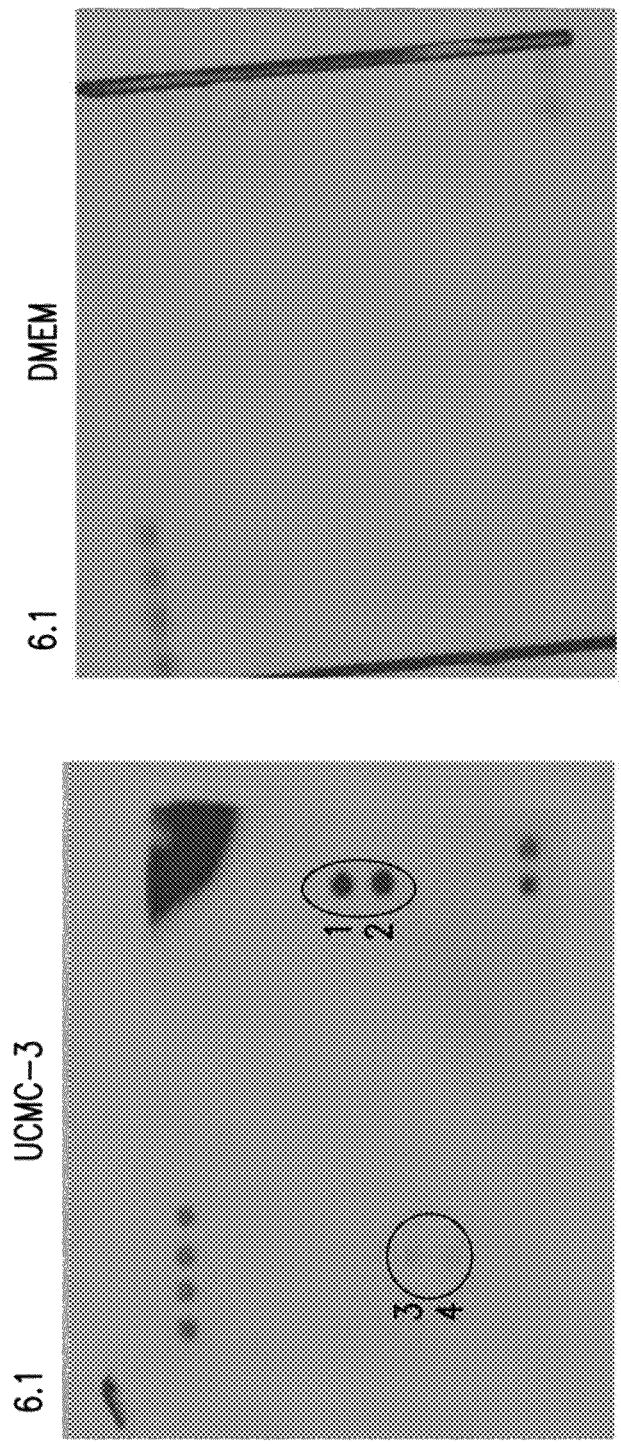
Figures 2, 11:
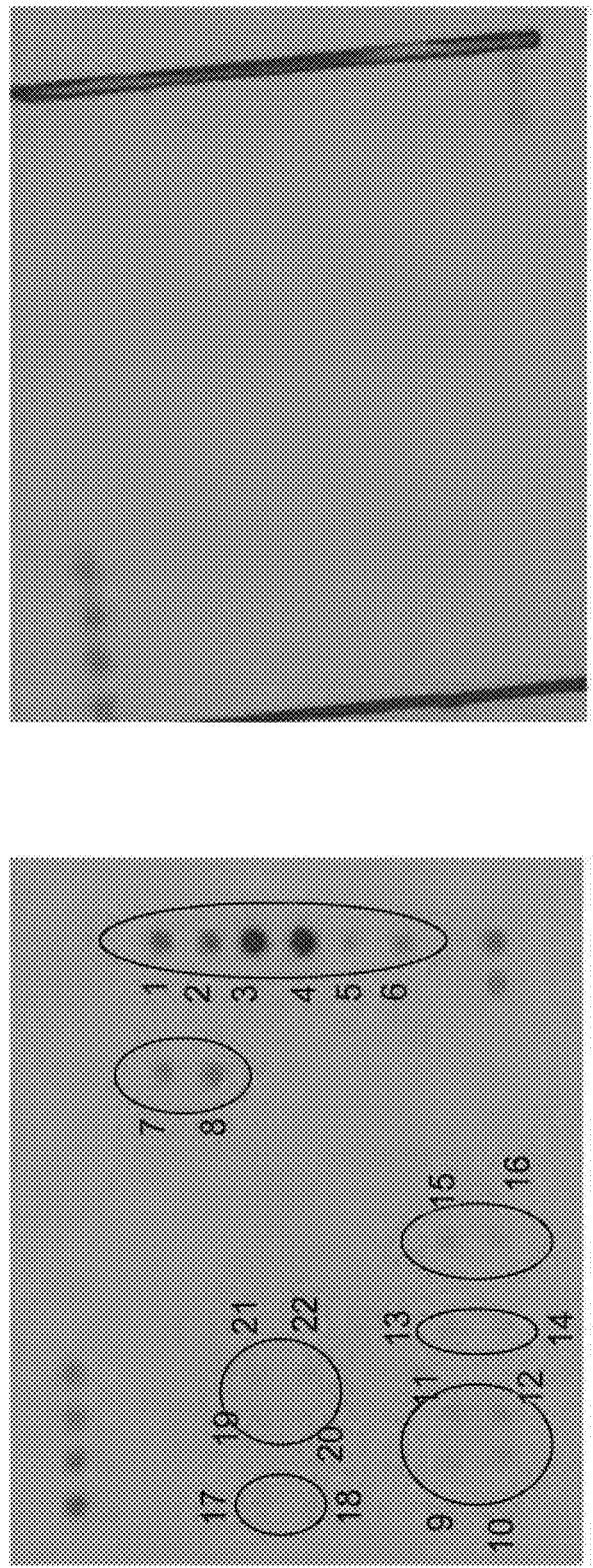
Figures 3, 11:
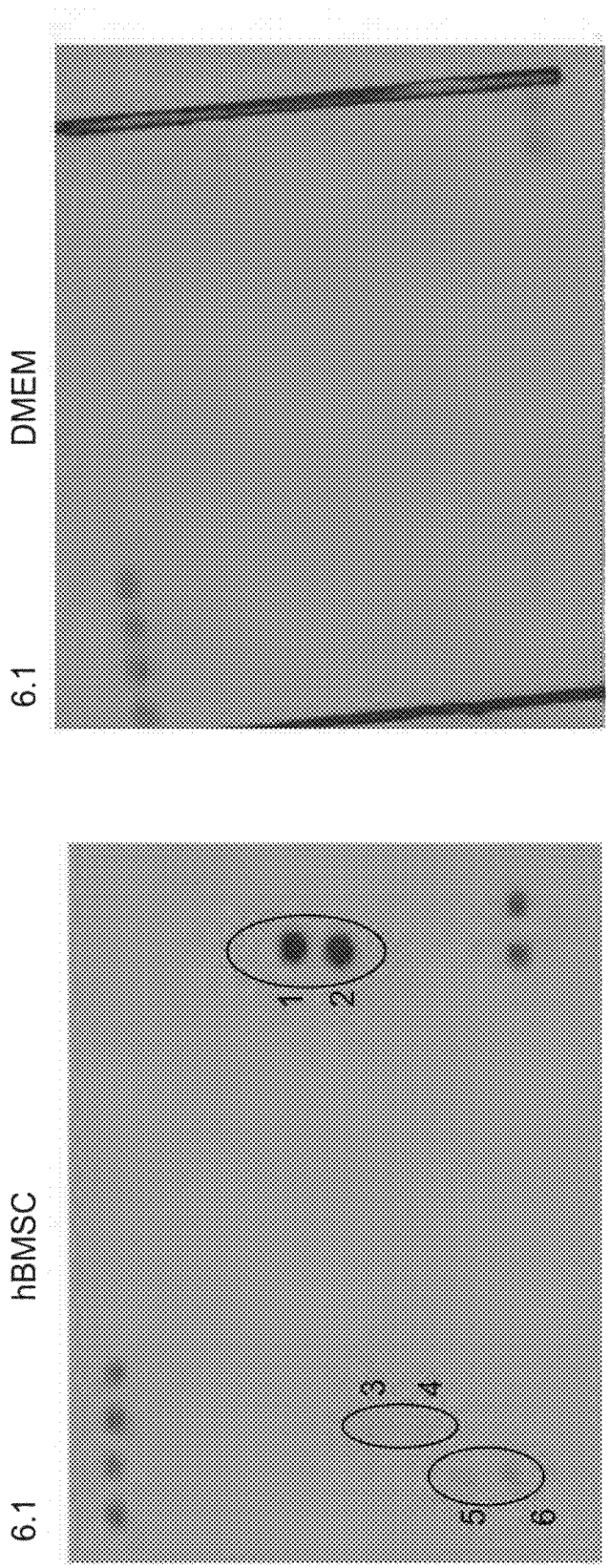
Figures 4, 11:
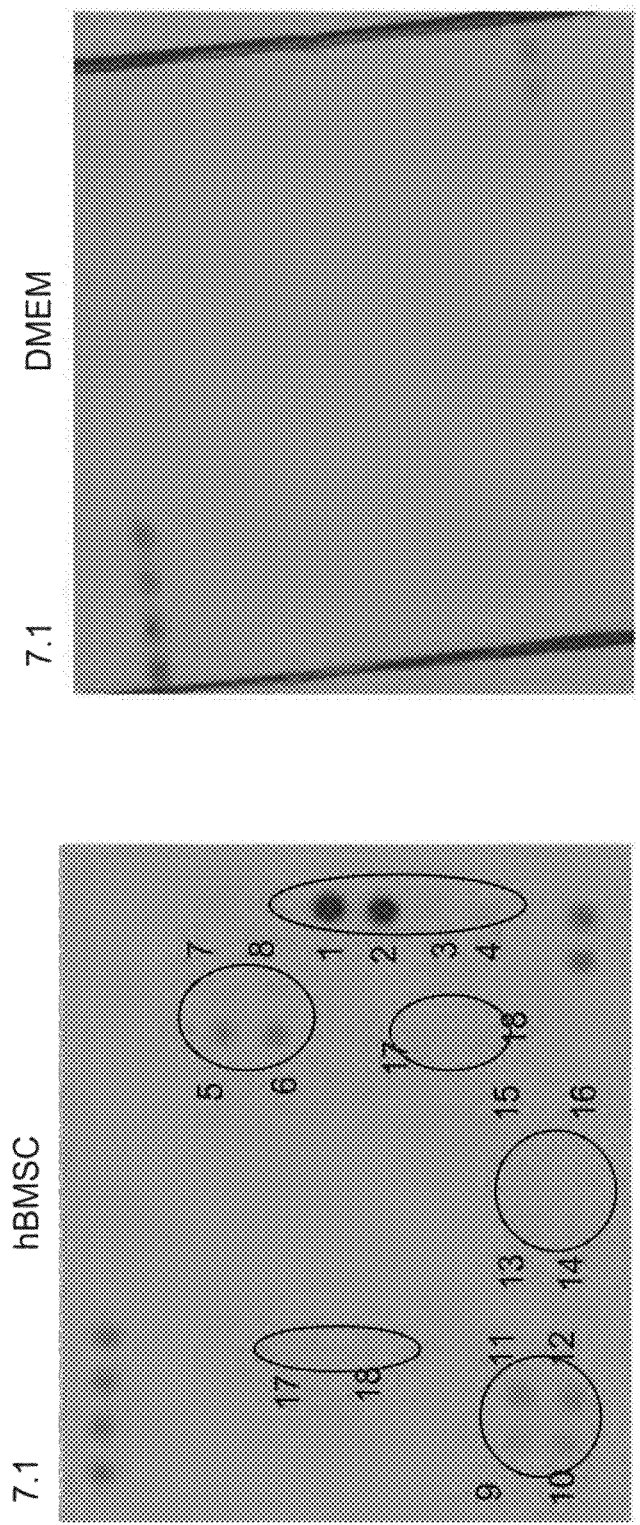
Figures 1, 12:
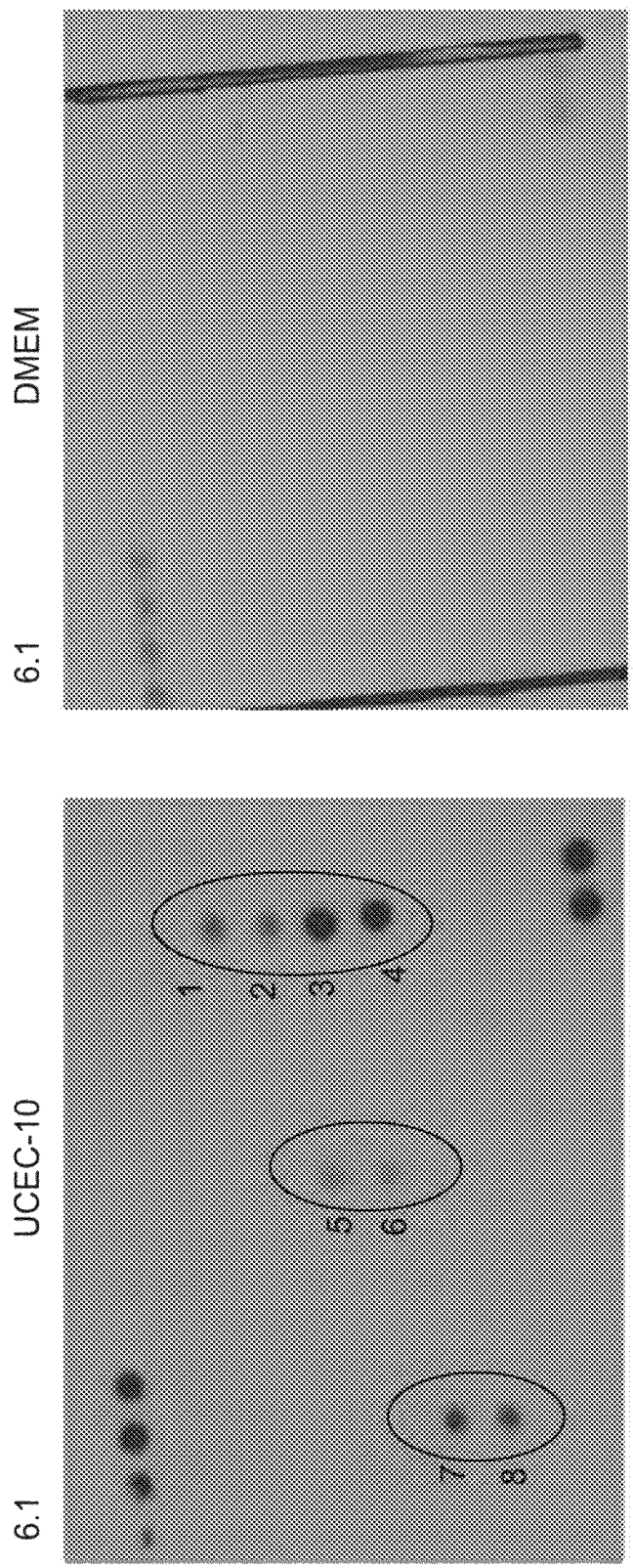
Figures 2, 12:
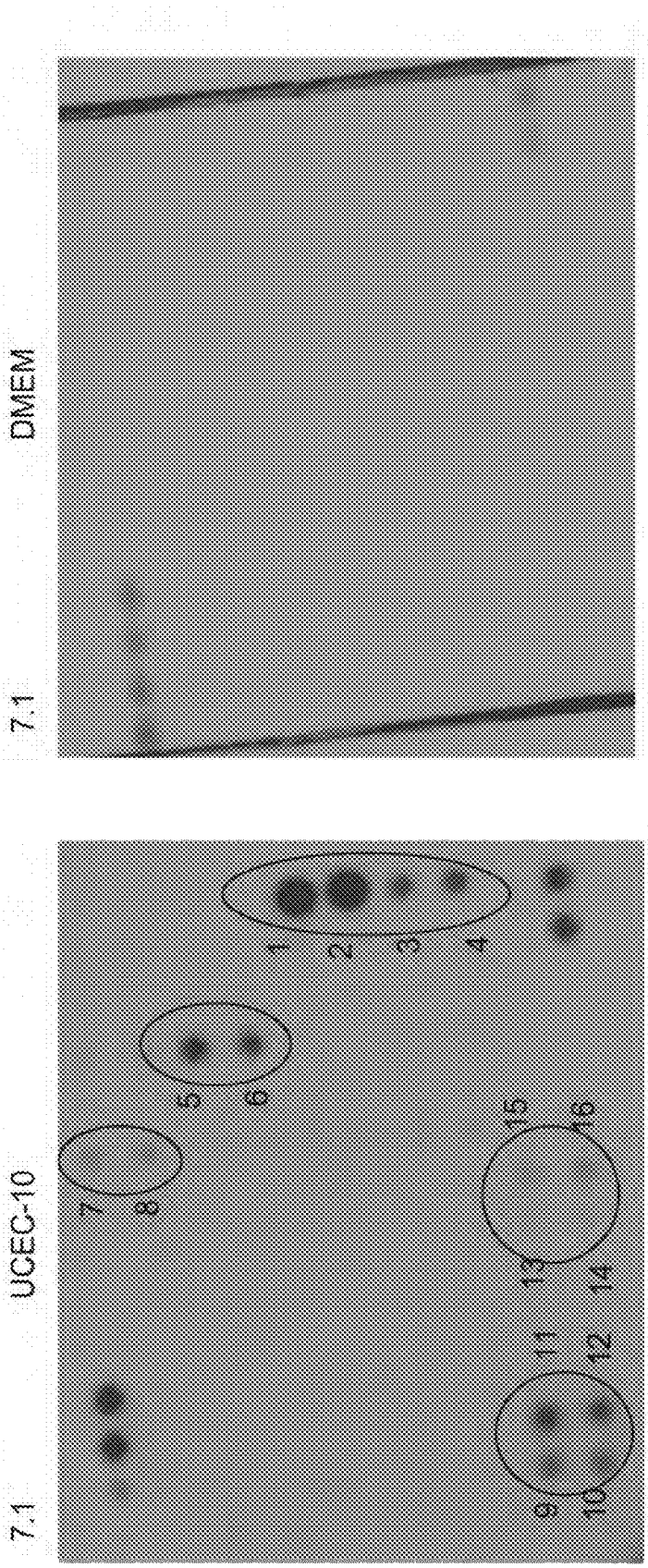
Figures 3, 12:
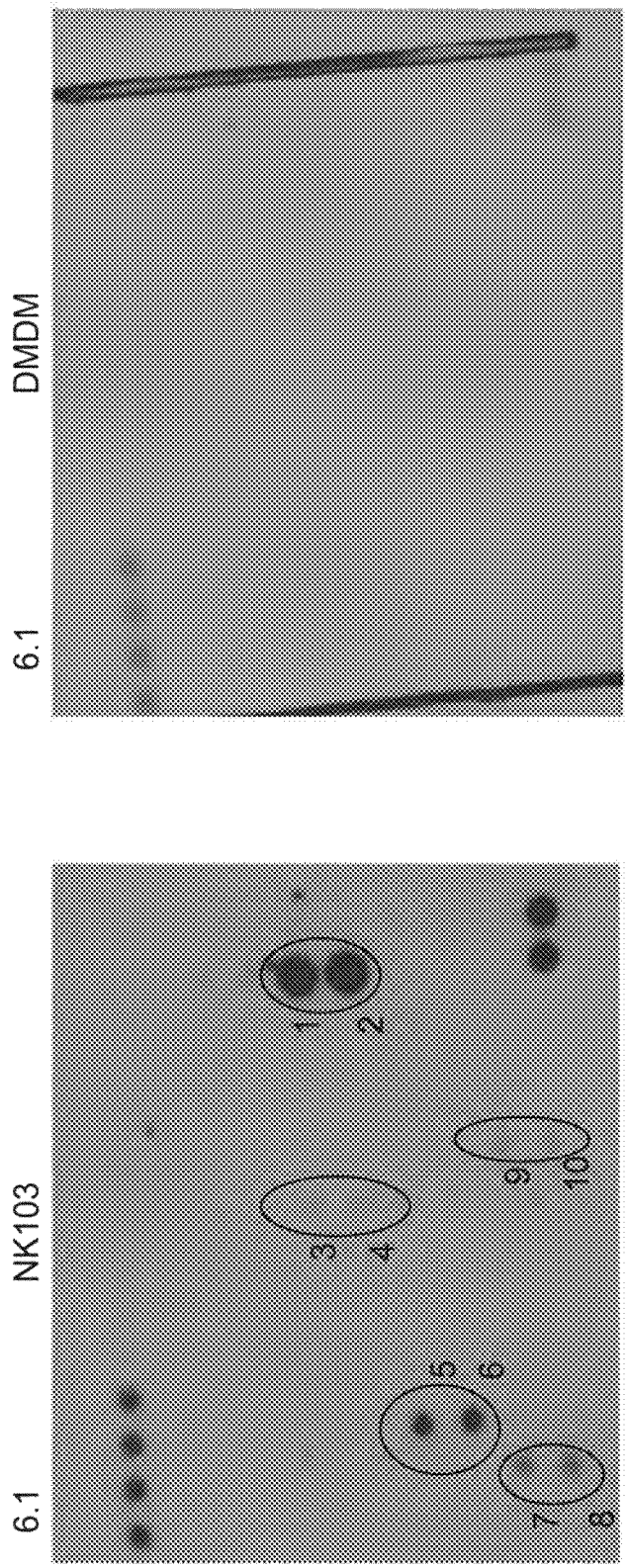
Figures 4, 12:
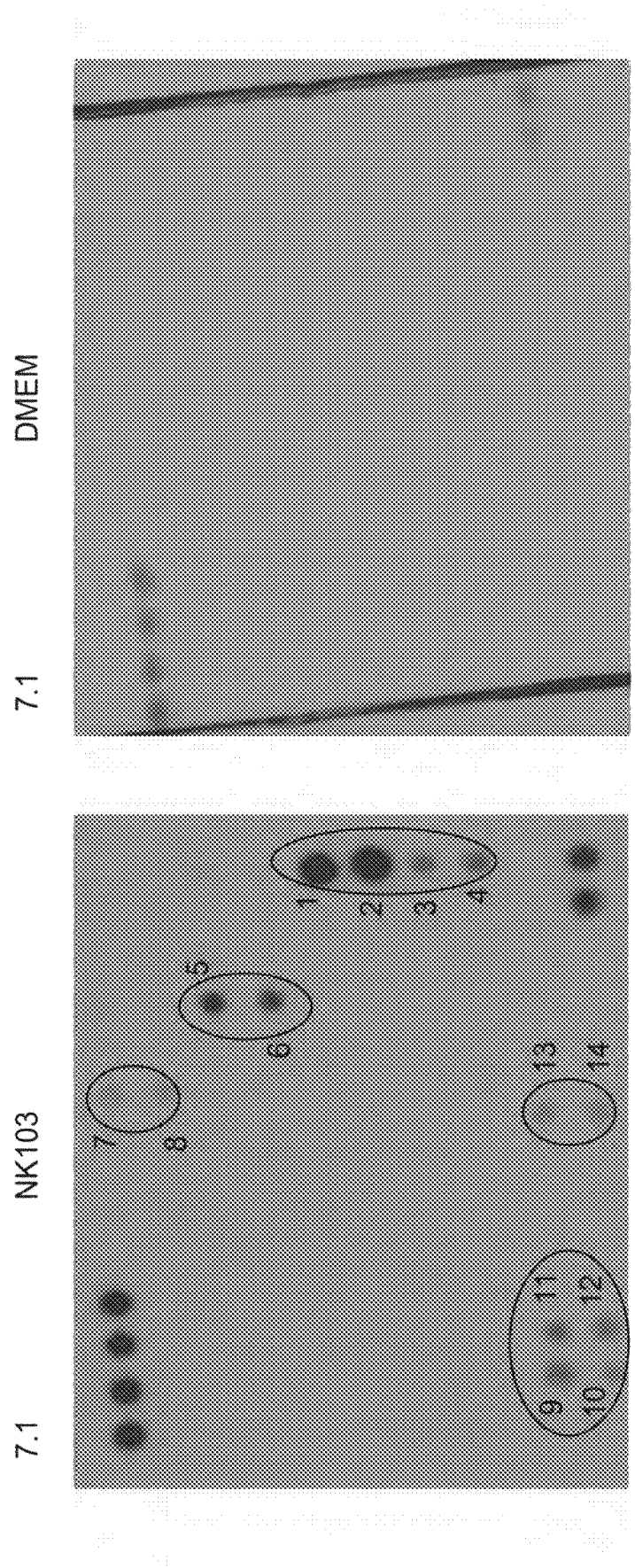
Figures 5, 12:
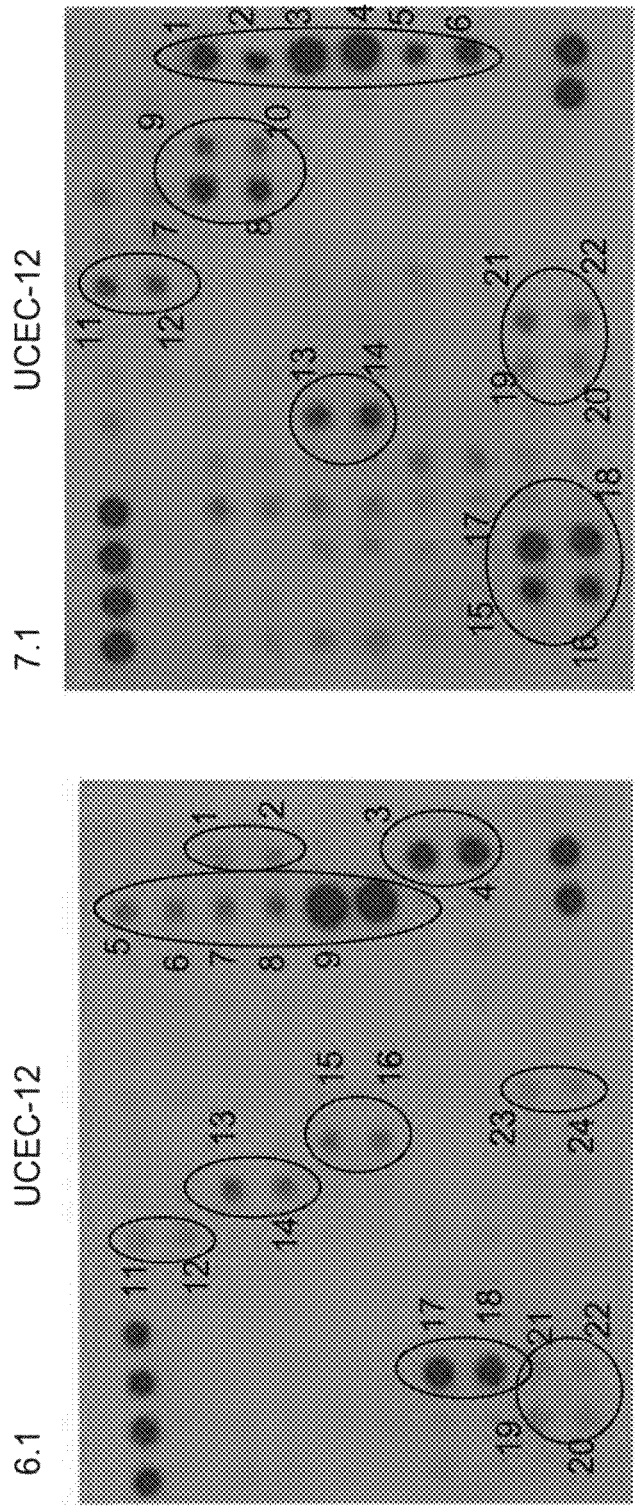
FIG. 5 shows changes in cell morphology of NF and ADMC cultured in serum starvation conditions (DMEM only) reflected by flatter cells and less dense cytoplasm as compared with serum rich conditions (DMEM/10% FCS) where cells are more rounded with a dense cytoplasm (FIG. 5A, B, C, D). No change in morphology was observed in both UCMC groups cultured under identical conditions of serum-free vs. serum rich media (FIG. 5E, F, G, H), indicating a difference in behavior and physiology of these latter mesenchymal cells.
Figures 2, 13:
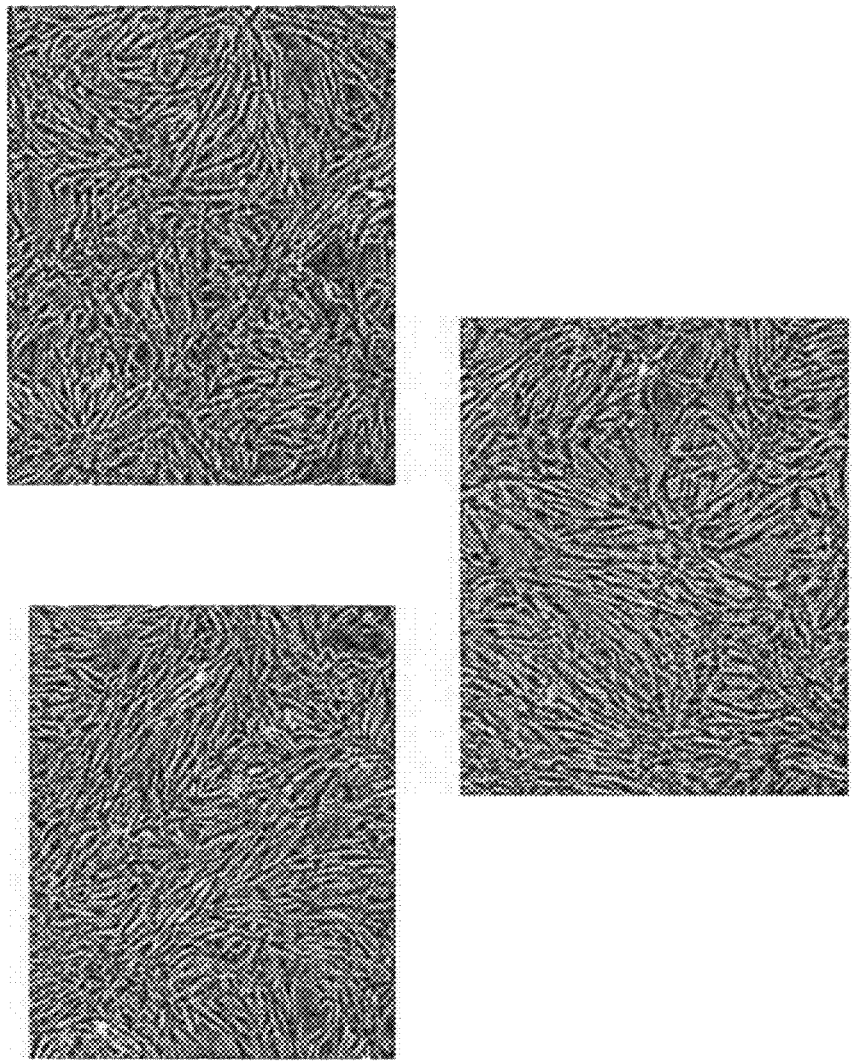
Figures 3, 13:
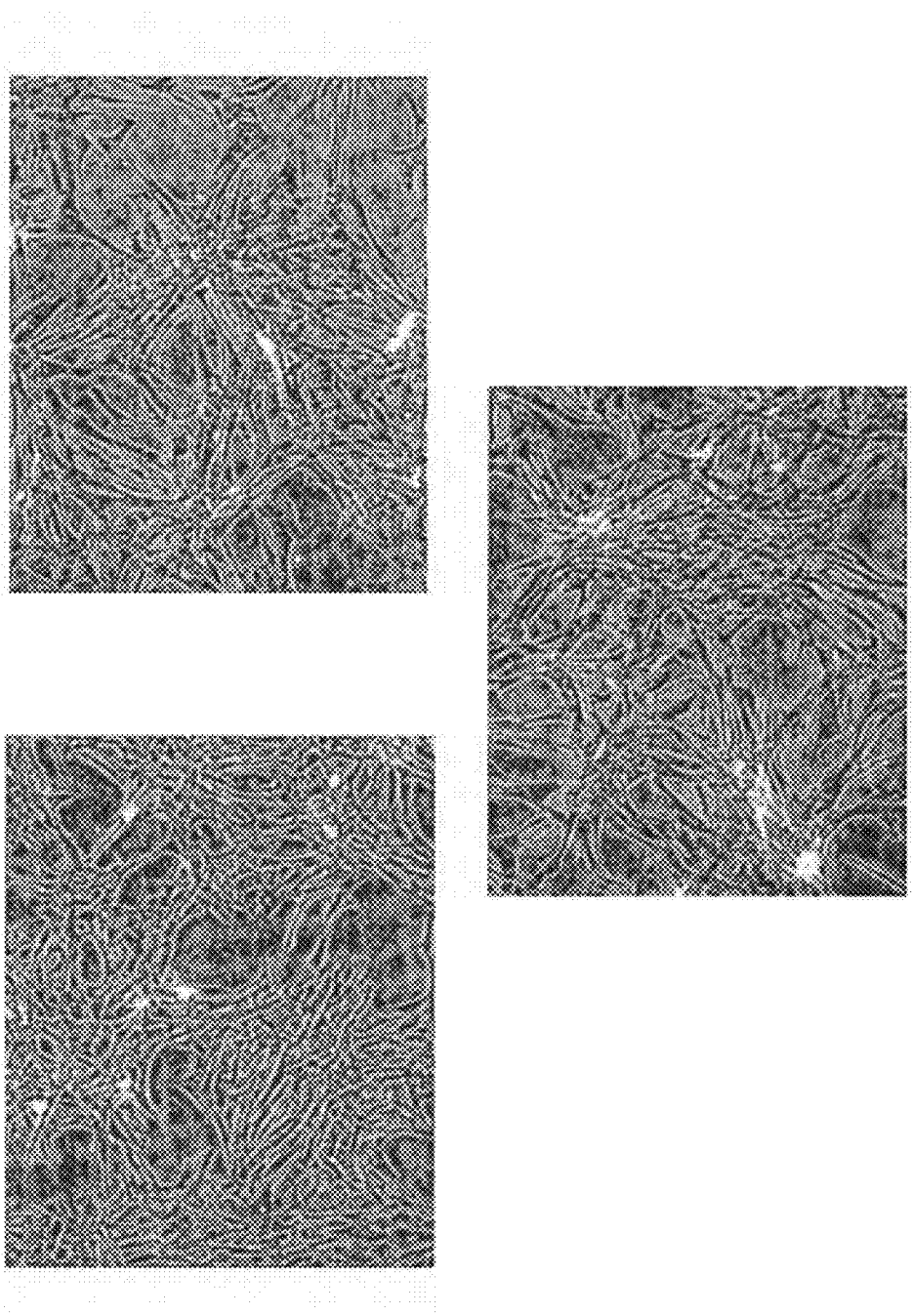
Figure 13:
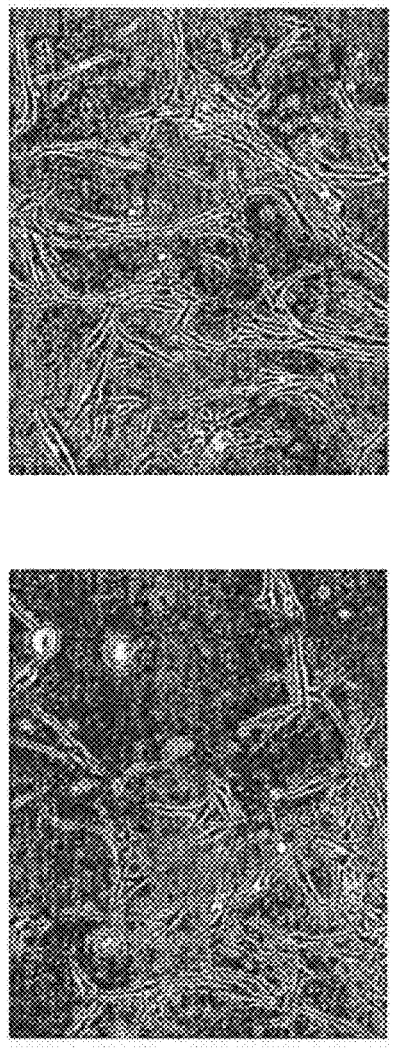
Figure 6:
Figure 14:
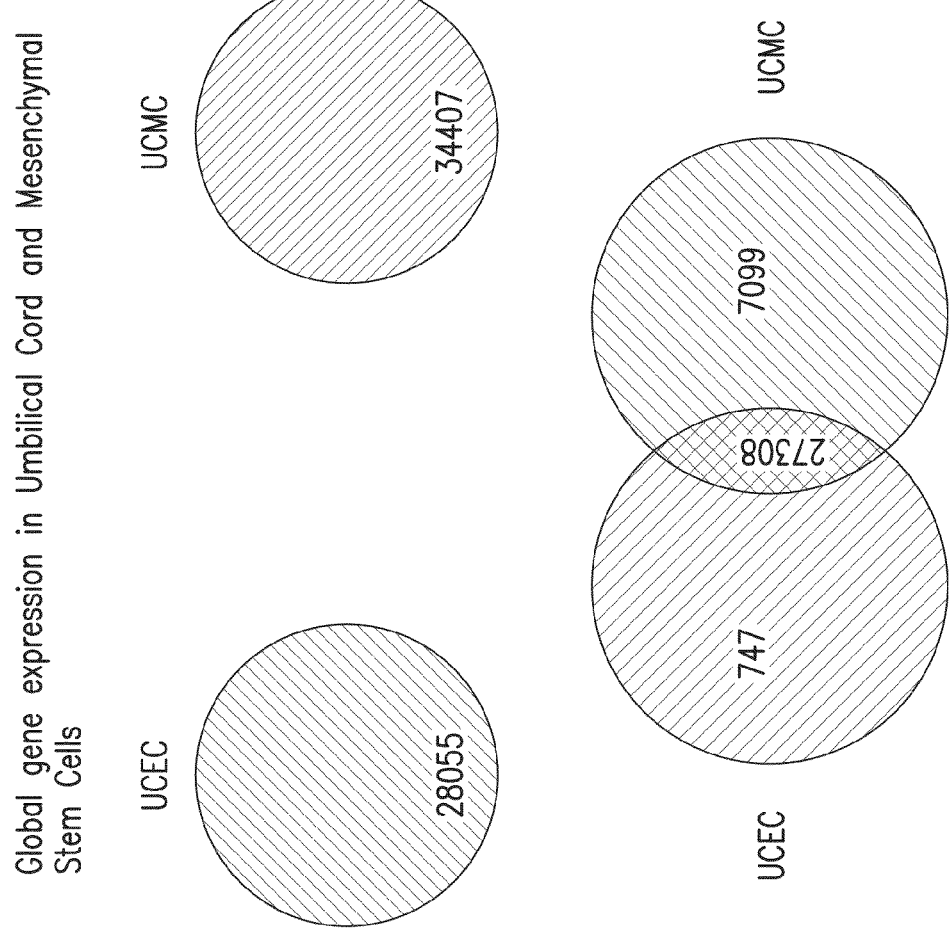
Figure 15:
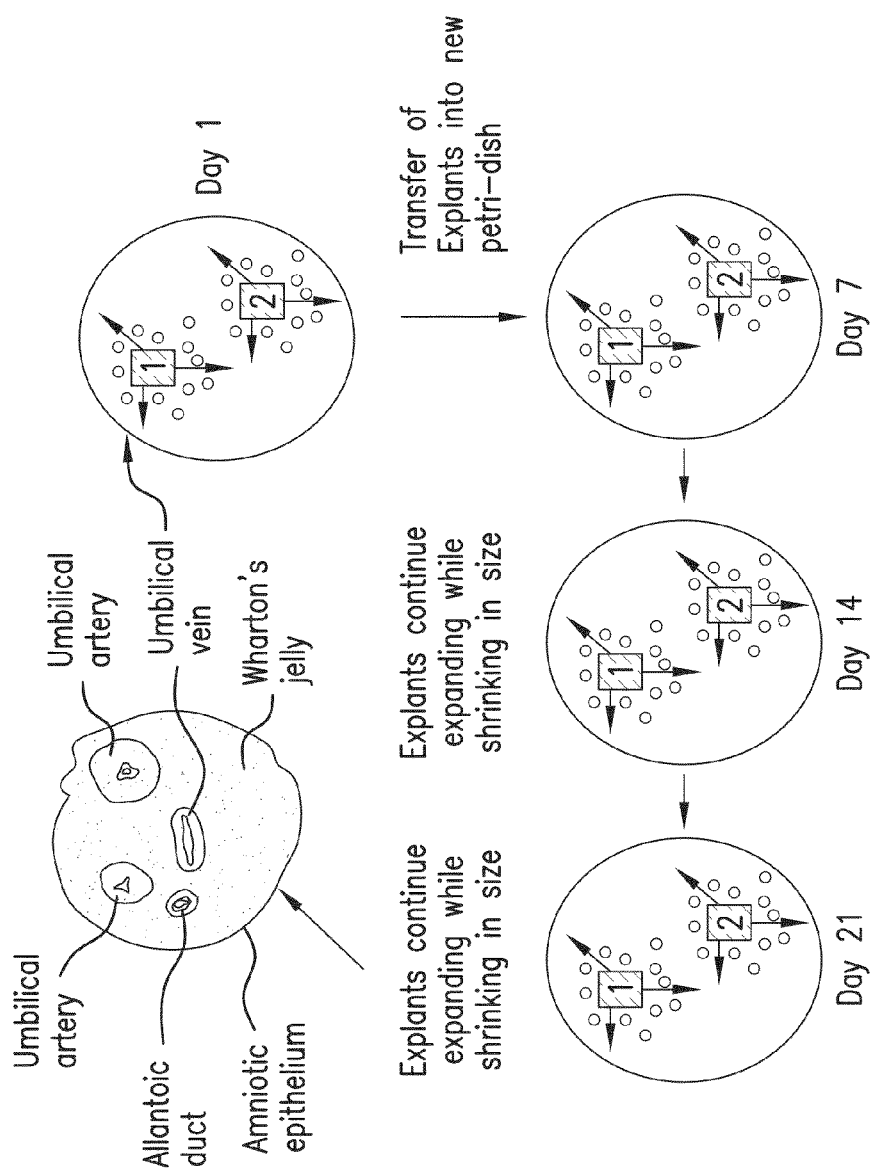
Figure 16:
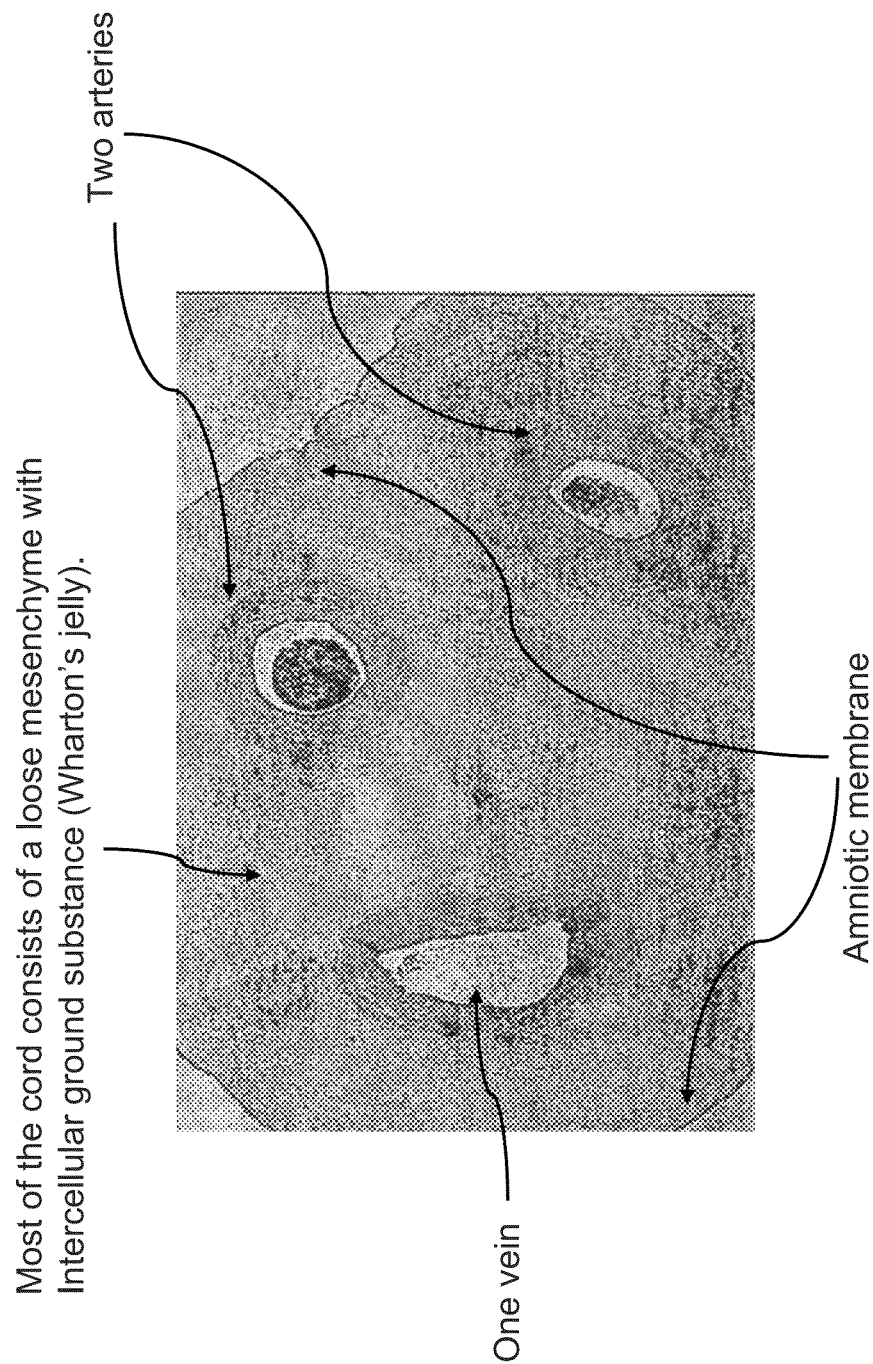

Western blot analysis (FIG. 9-1 to FIG. 9-30) shows that mesenchymal stem cells from umbilical cord amniotic membrane (UCMC) and umbilical cord epithelial cells (UCEC) isolated in accordance with the invention expressed the POU5f1 gene which encodes the transcription factor Octamer-4 (Oct-4) a specific marker of embryonic stem cells (cf. Niwa, H., Miyazaki, J., and Smith, A. G. (2000). Nat. Genet. 24, 372-376) (FIG. 9-1). Thus, this analysis indicates the embryonic-like properties of these stem cells. These mesenchymal and epithelial cells also expressed Bmi-1, a marker that is required for the self-renewal of adult stem cells (cf., Park et al., J. Clin. Invest. 113, 175-179 (2004) (FIG. 9-27) as well as leukemia inhibitory factor (LIF) (FIG. 9-28) that is considered to maintain the pluripotency of stem cells and embryonic cells and has thus, for example been used for isolation and expansion of human neural stem cells. These cells also highly expressed the other growth factors such as connective tissue growth factor (CTGF) (FIG. 9-6 and FIG. 9-7), vascular endothelial growth factor (VEGF) (FIG. 9-10 and FIG. 9-11), placenta-like growth factor PLGF (FIG. 9-4 and FIG. 9-5), STAT3 (FIG. 9-2 and FIG. 9-3), stem cell factor (SCF) (FIG. 9-16), Hepatoma-derived Growth Factor (HDGF) (FIG. 9-14 and FIG. 9-15), Fibroblast Growth Factor-2 (FGF-2) (FIG. 9-12 and FIG. 9-13), Platelet-derived Growth Factor (PDGF) (FIG. 9-8 and FIG. 9-9), alpha-Smooth Muscle Actin ($\alpha$-SMA) (FIG. 9-17), Fibronectin (FIG. 9-18 and FIG. 9-19), Decorin (FIG. 9-20), Syndecan-1,2,3,4 (FIG. 9-21 to FIG. 9-26). In FIG. 9-1 to FIG. 9-30, the expression of these genes is compared to human dermal fibroblasts, bone marrow mesenchymal cells (BMSC) and adipose-derived mesenchymal cells (ADMC). FIG. 9-29 shows Western blot data of the secretion of leukemia inhibitory factor (LIF) by both UCEC and UCMC.

FIG. 9-30 shows highly secreted Activin A and Follistatin (both of which proteins are well known to promote tissue repair and regeneration, enhanced angiogenesis, and maintain embryonic stem cell culture, so that expression of the respective genes is a sign for the embryonic properties and ability of the cells to differentiate) detected ELISA assay (FIG. 9-30) in supernatants of umbilical cord mesenchymal and epithelial stem cell culture in comparison with bone marrow, adipose derived stem cells, human dermal fibroblasts and epidermal keratinocytes. Also these results indicate that the cells of the invention are promising candidates in therapeutic application of these cells areas such as regenerative medicine, aging medicine, tissue repair and tissue engineering. In addition, FIG. 9-29 and FIG. 9-30 show the capability of the cells to secret an expression product into the culture medium.

Mesenchymal cells were further characterized by analysis of secreted cytokines and growth factors in comparison with human bone-marrow mesenchymal stem cells. The umbilical cord epithelial stem cells (UCEC) were analysed in comparison with human epidermal keratinocytes. This analysis was carried out as follows: Briefly, UCMC, UCEC, dermal fibroblasts, bone-marrow mesenchymal cells, epidermal keratinocytes were cultured in growth media until 100% confluence (37° C., 5% $CO_2$) and then synchronized in starvation medium (serum-free DMEM) for 48 hours. The next day, the medium was replaced the next against fresh serum-free DMEM and the cells then were cultivated for another 48 hours. Conditioned media were collected, concentrated and analyzed using a Cytokine Array (RayBiotech, Inc, GA, USA).

The results of this analysis show that UCMC secrete Interleukin-6 (IL-6); (MCP1); hepatocyte growth factor (HGF); Interleukin-8 (IL8); sTNFR1; GRO; TIMP1; TIMP2; TRAILR3; uPAR; ICAM1; IGFBP3; IGFBP6 (FIG. 11-1 to FIG. 11-4), whereas UCEC secrete IGFBP-4; PARC; EGF; IGFBP-2; IL-6; Angiogenin; GCP-2; IL1 Ra; MCP-1; RANTES; SCF; TNF$\beta$; HGF; IL8; sTNFR; GRO; GRO-$\alpha$; Amphiregulin; IL-1R4/ST2; TIMP1; TIMP2; uPAR; VEGF (FIG. 12-1 to FIG. 12-7).

Accordingly, this shows that both cells types secrete large amounts of cytokines and growth factors that play important roles in developmental biology, tissue homeostasis, tissue repair and regeneration and angiogenesis. This further demonstrates the versatility of the cells of the invention for use in the respective therapeutic applications.

In addition, the cells of the invention were further examined with respect to their safety profile using mouse teratoma formation assay as an indicator. Six SCID mice were used in these experiments. A suspension of more than 2 million UCMC was injected with a sterile 25G needle into the thigh muscle of each SCID mouse. Animals were kept up to 6 months and tumor formation was assessed. No tumor formation was observed in these mice (data not shown). This indicates that the cells of the invention are safe and do not have any capability to form tumors, benign or otherwise.

The UCMC were also analysed for their expression of human leukocyte antigen (HLA) molecules. When testing on major histocompatibility complex (MHC) class I molecules, this analysis showed that HLA-A molecules were present in high number (test result in arbitrary unit: 3201), meaning that the cells are HLA-A positive whereas expression of HLA-B molecules was insignificant (test result in arbitrary units: 35), meaning the cells are HLA-B negative. As HLA-B is mainly responsible for rejection reaction in transplantation, this result indicates that the cells of the invention are not only suitable for autologous transplantation but also for allogeneic transplantation. The cells were tested positive for Class II MHC molecule HLA-DR52 and tested negative for Class II MHC molecule HLA-DRB4. HLA-DRB1 was also found to be present (0301/05/20/22, Example 4

Cultivation of Stem/progenitor Cells in Serum Free Media

UCMC cells were cultured in DMEM containing 10 FCS and in serum-free media, PTT-1, PTT-2 and PTT-3. The three media PTT-1, PTT-2 and PTT-3 were prepared by one of the present inventors, Dr Phan. In brief, these 3 media do not contain fetal bovine or human serum, but contain different cytokines and growth factors such as IGF, EGF, TGF-beta, Activin A, BMPs, PDGF, transferrin, and insulin. The growth factor components vary between media to assess differential growth characteristics. The cultivation was carried out as follows: Different proportions of growth factors and cytokines were added in basal media. UCMC were thawed and maintained in these media for 10 days. Cell proliferation was monitored under light microscopy.

FIGS. 13-1 to FIG. 13-7 show good UCMC growth in the 4 different media groups (FIG. 13-1 to FIG. 13-5), wherein the morphology of UCMC cells is different depending on the ratio or proportion of cytokines or growth factors present in the respective media. In contrast, bone marrow and adipose-derived mesenchymal cells did not grow well in these serum-free media (FIG. 13-6 and FIG. 13-7). Accordingly, the good growth of the UCMC demonstrates the robustness of the cells of the invention and their high viability, indicating that their growth characteristics are superior to conventional sources of mesenchymal stem cells as bone marrow derived and adipose-derived mesenchymal cells. In this respect, it is worth to note that (bovine) serum free medium was used in these experiments and that the majority of human mesenchymal cells do not grow well in serum-free medium systems. Thus, using the cells of the invention in connection with defined serum-free media technologies is a big advantage in cell therapy as the risks of using fetal bovine serum for cell culture and expansion are removed. (Although use of bovine serum has been practiced for a long time and typically optimizes cell growth, concerns of its used have been raised as to the transmission of zoonoses as Bovine Spongiform Encephalopathy (Mad Cow Disease)).

Example 5

Characterization of the Gene Expression Profile of Umbilical Cord Epithelial and Mesenchymal Stem Cells The gene expression profile of umbilical cord epithelial and mesenchymal stem cells was analyzed using a DNA microarray. For this purpose, UCMC and UCEC were cultured in growth media at 37° C., 5% $CO_2$ until 100% confluence. Cells were synchronized in basal media for 48 hours then replaced with fresh basal media for another 48 hours. Total RNA was harvested and sent to Silicon Genetics Microarray Service. Data analysis was performed using GeneSpring 7.2). FIG. 14 summarizes the global gene expression. UCEC expressed a total of 28055 genes and UCMC expressed a total of 34407 genes. There are 27308 overlapping genes expressing in both cell types. 747 genes expressed were unique to UCEC and 7099 genes expressed were unique to UCMC. The selected genes of interest are presented in FIG. 14.

Both stem cell types expressed 140 genes related to embryonic stem cells and embryonic development, further supporting that the cells of the invention have embryonic stem cell-like properties: Nanog; Alpha-fetal protein; Pre-B-cell leukemia transcription factor 3; Laminin alpha 5; Carcinoembryonic antigen-like 1; abhydrolase domain containing 2; Delta-like 3 (*Drosophila*); Muscleblind-like (*Drosophila*); GNAS complex locus; Carcinoembryonic antigen-related cell adhesion molecule 3; Palmitoyl-protein thioesterase 2; Pregnancy specific beta-1-glycoprotein 2; Carcinoembryonic antigen-like 1; Embryonic ectoderm development; Maternal embryonic leucine zipper kinase; Chorionic somatomammotropin hormone 2; Forkhead box D3; radical fringe homolog (*Drosophila*); Kinesin family member 1B; Myosin, heavy polypeptide 3, skeletal muscle, embryonic; Split hand/foot malformation (ectrodactyly) type 3; TEA domain family member 3; Laminin, alpha 1; Chorionic somatomammotropin hormone 1; placental lactogen; Corticotropin releasing hormone receptor 1; thyrotrophic embryonic factor; Aryl-hydrocarbon receptor nuclear translocator 2; Membrane frizzled-related protein; Neuregulin 1'Collagen, type XVI, alpha 1; Neuregulin 1; Chorionic somatomammotropin hormone 1 (placental lactogen); CUG triplet repeat, RNA binding protein 1; Chorionic somatomammotropin hormone 1 (placental lactogen) Bystin-like; MyoD family inhibitor; Retinoic acid induced 2; GNAS complex locus; Pre-B-cell leukemia transcription factor 4; Laminin, alpha 2 (merosin, congenital muscular dystrophy); SMAD, mothers against DPP homolog 1 (*Drosophila*); *Homo sapiens* transcribed sequence with moderate similarity to protein pir:D28928 (*H. sapiens*) D28928 pregnancy-specific beta-1 glycoprotein IB, abortive—human (fragment); Kinesin family member 1B; Bruno-like 4, RNA binding protein (*Drosophila*); Embryo brain specific protein; Pregnancy-induced growth inhibitor; SMAD, mothers against DPP homolog 5 (*Drosophila*); Chorionic somatomammotropin hormone 2; Adenylate cyclase activating polypeptide 1 (pituitary); Carcinoembryonic antigen-related cell adhesion molecule; Laminin, alpha 3; Protein O-fucosyltransferase 1; Jagged 1 (Alagille syndrome); Twisted gastrulation homolog 1 (*Drosophila*); ELAV (embryonic lethal, abnormal vision, *Drosophila*)-like 3 (Hu antigen C); Thyrotrophic embryonic factor; Solute carrier family 43, member 3; Inversin; nephronophthisis 2 (infantile); inversion of embryonic turning; *Homo sapiens* inversin (INVS), transcript variant 2, mRNA; *Homo sapiens* transcribed sequences; Homeo box D8; Embryonal Fyn-associated substrate; ELAV (embryonic lethal, abnormal vision, *Drosophila*)-like 1 (Hu antigen R); Basic helix-loop-helix domain containing, class B, 2; Oxytocin receptor; Teratocarcinoma-derived growth factor 1; Fms-related tyrosine kinase 1 (vascular endothelial growth factor/vascular permeability factor receptor); Adrenomedullin; Nuclear receptor coactivator 6-CUG triplet repeat, RNA binding protein 1; Twisted gastrulation homolog 1 (*Drosophila*); Carcinoembryonic antigen-related cell adhesion molecule 4; Protein tyrosine phosphatase, receptor type, R; Acrg embryonic lethality (mouse) minimal region ortholog; EPH receptor A3; Delta-like 1 (*Drosophila*); Nasal embryonic LHRH factor; Transcription factor CP2-like 1; Split hand/foot malformation (ectrodactyly) type 3; Jagged 2; *Homo sapiens* transcribed sequence; Neuregulin 1; Split hand/foot malformation (ectrodactyly) type 1; Solute carrier family 43, member 3; Hydroxyacyl-Coenzyme A dehydrogenase/3-ketoacyl-Coenzyme A thiolase/enoyl-Coenzyme A hydratase (trifunctional protein), alpha subunit; Fucosyltransferase 10 (alpha (1,3) fucosyltransferase); Acrg embryonic lethality (mouse) minimal region ortholog; Carcinoembryonic antigen-related cell adhesion molecule 7; Nucleophosmin/nucleoplasmin, 2; Fc fragment of IgG, receptor, transporter, alpha; Twisted gastrulation homolog 1 (Drosophila); Homo sapiens similar to vacuolar protein sorting 35; maternal-embryonic 3 (LOC146485), mRNA; abhydrolase domain containing 2; T, brachyury homolog (mouse); A disintegrin and metalloproteinase domain 10; Ribosomal protein L29; Endothelin converting enzyme 2; ELAV (embryonic lethal, abnormal vision, Drosophila)-like 1 (Hu antigen R); Trophinin; Homeo box B6; Laminin, alpha 4; Homeo box B6; hypothetical protein FLJ13456; NACHT, leucine rich repeat and PYD containing 5; ELAV (embryonic lethal, abnormal vision, Drosophila)-like 1 (Hu antigen R); Undifferentiated embryonic cell transcription factor 1; Pregnancy-associated plasma protein A, pappalysin 1; Secretoglobin, family 1A, member 1 (uteroglobin); Parathyroid hormone-like hormone; Carcinoembryonic antigen-related cell adhesion molecule 1 (biliary glycoprotein); Laminin, alpha 1.

Both stem cell types also expressed thousands of genes related to developmental biology, cell growth and differentiation, cell homeostasis, cell and tissue repair and regeneration. Examples of such growth factors and their receptors is as follows: (G-CSF, FGFs, IGFs, KGF, NGF, VEGFs, PIGF, Angiopoietin, CTGF, PDGFs, HGF, EGF, HDGF, TGF-beta, Activins and Inhibins, Follistatin, BMPs, SCF/c-Kit, LIF, WNTs, SDFs, OncostatinM, Interleukins, Chemokines and many others); MMPs, TIMPs extracellular matrices (collagens, laminins, fibronectins, vitronectins, tenascins, intergrins, syndecans, decorin, fibromoludin, proteoglycans, sparc/osteonectin, mucin, netrin, glypican, cartilage associated protein, matrilin, hyaluronan, fibulin, ADAMTS, biglycan, discoidin, desmosome components, ICAMs, cadherins, catenins and many others); cytokeratins.

There are groups of genes present only in UCMC. These genes are related to the following: Normal Physiological Processes (Insulin-like growth factor 1 (somatomedin C); Insulin-like 4 (placenta); Relaxin 1; Plasminogen; Insulin-like growth factor 1 (somatomedin C); Insulin-like 5; Insulin-like growth factor 1 (somatomedin C); Insulin-like growth factor 2 (somatomedin A), Homeostasis (Radial spokehead-like 1; Hemochromatosis; Chemokine (C-C motif) ligand 5; Interleukin 31 receptor A; Chemokine (C-X-C motif) ligand 12 (stromal cell-derived factor 1); Nuclear receptor subfamily 3, group C, member 2; Hemochromatosis; Chemokine (C-C motif) ligand 23; Chemokine (C-C motif) ligand 23; Ferritin mitochondrial; Peroxisome proliferative activated receptor, gamma, coactivator 1, alpha; Surfactant, pulmonary-associated protein D; Chemokine (C-C motif) ligand 11; Chemokine (C-C motif) ligand 3; EgI nine homolog 2 (C. elegans); Peroxisome proliferative activated receptor, gamma, coactivator 1, beta; Chemokine (C-C motif) ligand 1; Chemokine (C-X-C motif) ligand 12 (stromal cell-derived factor 1); ATPase, Na+/K+ transporting, alpha 2 (+) polypeptide; Chemokine (C motif) ligand 2; Hemopexin; Ryanodine receptor 3), Morphogenesis (Spectrin, alpha, erythrocytic 1 (elliptocytosis 2); Homeo box D3; Eyes absent homolog 1 (Drosophila); Ras homolog gene family, member J; Leukocyte specific transcript 1; Ectodysplasin A2 receptor; Glypican 3; Paired box gene 7; Corin, serine protease; Dishevelled, dsh homolog 1 (Drosophila); Ras homolog gene family, member J; T-box 3 (ulnar mammary syndrome); Chondroitin beta1,4 N-acetylgalactosaminyltransferase; Chondroitin beta1,4 N-acetylactosaminyltransferase; SRY (sex determining region Y)-box 10; Myosin, heavy polypeptide 9, non-muscle; Luteinizing hormone/choriogonadotropin receptor; radical fringe homolog (Drosophila); Secreted frizzled-related protein 5; Wingless-type MMTV integration site family, member 11; Eyes absent homolog 2 (Drosophila); Muscleblind-like (Drosophila); T-box 5; Mab-21-like 1 (C. elegans); Growth arrest-specific 2; Sex comb on midleg homolog 1 (Drosophila); T-box 6; Filamin-binding LIM protein-1; Melanoma cell adhesion molecule; Twist homolog 1 (acrocephalosyndactyly 3; Saethre-Chotzen syndrome) (Drosophila); Homeo box A11; Keratocan; Fibroblast growth factor 1 (acidic); Carboxypeptidase M; CDC42 effector protein (Rho GTPase binding) 4; LIM homeobox transcription factor 1, beta; Engrailed homolog 1; Carboxypeptidase M; Fibroblast growth factor 8 (androgen-induced); Fibroblast growth factor 18; Leukocyte specific transcript 1; Endothelin 3; Paired-like homeodomain transcription factor 1), Embryonic Development (Pregnancy specific beta-1-glycoprotein 3; ELAV (embryonic lethal, abnormal vision, Drosophila)-like 4 (Hu antigen D); G protein-coupled receptor 10; Ectodysplasin A2 receptor; ATP-binding cassette, sub-family B (MDR/TAP), member 4; Pregnancy specific beta-1-glycoprotein 11; Nasal embryonic LHRH factor; Relaxin 1; Notch homolog 4 (Drosophila); Pregnancy specific beta-1-glycoprotein 6; pih-2P; Homo sapiens pregnancy-induced hypertension syndrome-related protein (PIH2); Oviductal glycoprotein 1, 120 kDa (mucin 9, oviductin); Progestagen-associated endometrial protein; Myosin, light polypeptide 4, alkali; atrial, embryonic; Prolactin; Notch homolog 4 (Drosophila); Pre-B-cell leukemia transcription factor 1; radical fringe homolog (Drosophila); Corticotropin releasing hormone; Nuclear receptor subfamily 3, group C, member 2; Neuregulin 2; Muscleblind-like (Drosophila); Myosin, light polypeptide 4, alkali; atrial, embryonic; Homo sapiens cDNA FLJ27401 fis, clone WMC03071; Extraembryonic, spermatogenesis, homeobox 1-like; Insulin-like 4 (placenta); Human processed pseudo-pregnancy-specific glycoprotein (PSG12) gene, exon B2C containing 3' untranslated regions of 2 alternative splice sites C1 and C2; Fms-related tyrosine kinase 1 (vascular endothelial growth factor/vascular permeability factor receptor); Pre-B-cell leukemia transcription factor 1; Pregnancy specific beta-1-glycoprotein 3; carcinoembryonic antigen-related cell adhesion molecule 1 (biliary glycoprotein); Steroid sulfatase (microsomal), arylsulfatase C, isozyme S; Homeo box B6; Protein O-fucosyltransferase 1; LIM homeobox transcription factor 1, beta; Carcinoembryonic antigen-related cell adhesion molecule 1 (biliary glycoprotein); Follicle stimulating hormone, beta polypeptide; Angiotensinogen (serine (or cysteine) proteinase inhibitor, clade A (alpha-1 antiproteinase, antitrypsin), member 8); Carcinoembryonic antigen-related cell adhesion molecule 6 (non-specific cross reacting antigen); Protein kinase C, alpha binding protein; Collectin sub-family member 10 (C-type lectin); Laminin, alpha 1), the Extracellular Space (Carboxylesterase 1 (monocyte/macrophage serine esterase 1); Fibroblast growth factor 5; Progastricsin (pepsinogen C); Sperm associated antigen 11; Proprotein convertase subtilisin/kexin type 2; Hyaluronan binding protein 2; Sema domain, immunoglobulin domain (Ig), short basic domain, secreted, (semaphorin) 3F; Interleukin 2; Chymotrypsin-like; Norrie disease (pseudoglioma); mucin 5, subtypes A and C, tracheobronchial/gastric; Carboxypeptidase B2 (plasma, carboxypeptidase U); radical fringe homolog (Drosophila); Pregnancy specific beta-1-glycoprotein 11; Meprin A, alpha (PABA peptide hydrolase); Tachykinin, precursor 1 (substance K, substance P, neurokinin 1, neurokinin 2, neuromedin L, neurokinin alpha, neuropeptide K, neuropeptide gamma); Fibroblast growth factor 8 (androgen-induced); Fibroblast growth factor 13; Hemopexin; Breast cancer 2, early onset; Fibroblast growth factor 14; Retinoschisis (X-linked, juvenile) 1; Chitinase 3-like 1 (cartilage glycoprotein-39); Dystonin; Secretoglobin, family 1D, member 2; Noggin; WAP four-disulfide core domain 2; CD5 antigen-like (scavenger receptor cysteine rich family); Scrapie responsive protein 1; Gremlin 1 homolog, cysteine knot superfamily (Xenopus laevis); Interleukin 16 (lymphocyte chemoattractant factor); Chemokine (C-C motif) ligand 26; Nucleobindin 1; Fibroblast growth factor 18; Insulin-like growth factor binding protein 1; Surfactant, pulmonary-associated protein A1; Delta-like 1 homolog (Drosophila); Cocaine- and amphetamine-regulated transcript; Meprin A, beta; Interleukin 17F; Complement factor H; Cysteine-rich secretory protein 2; Dystonin; WAP four-disulfide core domain 1; Prolactin; Surfactant, pulmonary-associated protein B; Fibroblast growth factor 5; Dickkopf homolog 2 (Xenopus laevis); Sperm associated antigen 11; Chemokine (C-C motif) ligand 11; Meprin A, alpha (PABA peptide hydrolase); Chitinase 3-like 2; C-fos induced growth factor (vascular endothelial growth factor D); Chemokine (C-C motif) ligand 4; Poliovirus receptor; Hyaluronoglucosaminidase 1; Oviductal glycoprotein 1, 120 kDa (mucin 9, oviductin); Chemokine (C-X-C motif) ligand 9; Secreted frizzled-related protein 5; Amelogenin (amelogenesis imperfecta 1, X-linked); Relaxin 1; Sparc/osteonectin, cwcv and kazal-like domains proteoglycan (testican); Chemokine (C-C motif) ligand 26; Fibroblast growth factor 1 (acidic); Angiopoietin-like 2; Fms-related tyrosine kinase 1 (vascular endothelial growth factor/vascular permeability factor receptor); Dystonin; Insulin-like 4 (placenta); Transcobalamin II; macrocytic anemia; Chemokine (C-C motif) ligand 1; Insulin-like growth factor binding protein, acid labile subunit; Complement factor H; Pregnancy specific beta-1-glycoprotein 6; Silver homolog (mouse); Proteoglycan 4; Fibroblast growth factor 16; Cytokine-like protein C17; Granulysin; Angiopoietin 2; Chromogranin B (secretogranin 1); Sema domain, immunoglobulin domain (Ig), and GPI membrane anchor, (semaphorin) 7A; Pleiotrophin (heparin binding growth factor 8, neurite growth-promoting factor 1); Chloride channel, calcium activated, family member 3; Secretoglobin, family 1D, member 1; Fibulin 1; Phospholipase A2 receptor 1, 180 kDa), and the Extracellular Matrix (ADAMTS-like 1; Periostin, osteoblast specific factor; Glypican 5; Leucine rich repeat neuronal 3; Transglutaminase 2 (C polypeptide, protein-glutamine-gamma-glutamyltransferase); A disintegrin-like and metalloprotease (reprolysin type) with thrombospondin type 1 motif, 2; Microfibrillar-associated protein 4; Glypican 3; Collagen, type V, alpha 3; Tissue inhibitor of metalloproteinase 2; Keratocan; Cartilage oligomeric matrix protein; Lumican; Hyaluronan and proteoglycan link protein 3; Statherin; A disintegrin-like and metalloprotease (reprolysin type) with thrombospondin type 1 motif, 3; Spondin 1, extracellular matrix protein; Chitinase 3-like 1 (cartilage glycoprotein-39); Collagen, type IV, alpha 3 (Goodpasture antigen); Wingless-type MMTV integration site family, member 7B; Collagen, type VI, alpha 2; Lipocalin 7; Hyaluronan and proteoglycan link protein 4; A disintegrin-like and metalloprotease (reprolysin type) with thrombospondin type 1 motif, 5 (aggrecanase-2); Fibronectin 1; Matrilin 1, cartilage matrix protein; Hypothetical protein FLJ13710; Chondroitin beta1,4 N-acetylgalactosaminyltransferase; Matrix metalloproteinase 16 (membrane-inserted); Von Willebrand factor; Collagen, type VI, alpha 2; Transmembrane protease, serine 6; Matrix metalloproteinase 23B; Matrix metalloproteinase 14 (membrane-inserted); Leucine rich repeat neuronal 3; SPARC-like (mast9, hevin); Sparc/osteonectin, cwcv and kazal-like domains proteoglycan (testican) 3; Dermatopontin; collagen, type XIV, alpha 1 (undulin); Amelogenin, Y-linked; Nidogen (enactin); ADAMTS-like 2; Hyaluronan and proteoglycan link protein 2; Collagen, type XV, alpha 1; Glypican 6; Matrix metalloproteinase 12 (macrophage elastase); Amelogenin (amelogenesis imperfecta 1, X-linked); A disintegrin-like and metalloprotease (reprolysin type) with thrombospondin type 1 motif, 15; Transmembrane protease, serine 6; A disintegrin-like and metalloprotease (reprolysin type) with thrombospondin type 1 motif, 16; Sparc/osteonectin, cwcv and kazal-like domains proteoglycan (testican); A disintegrin-like and metalloprotease (reprolysin type) with thrombospondin type 1 motif, 20; Collagen, type XI, alpha 1; Hyaluronan and proteoglycan link protein 1; Chondroitin beta1,4 N-acetylgalactosaminyltransferase; Asporin (LRR class 1); Collagen, type III, alpha 1 (Ehlers-Danlos syndrome type IV, autosomal dominant); Secreted phosphoprotein 1 (osteopontin, bone sialoprotein I, early T-lymphocyte activation 1); Matrix Gla protein; Fibulin 5; collagen, type XIV, alpha (undulin); Tissue inhibitor of metalloproteinase 3 (Sorsby fundus dystrophy, pseudoinflammatory); Collagen, type XXV, alpha 1; Cartilage oligomeric matrix protein; Collagen, type VI, alpha 1; Chondroadherin; Collagen, type XV, alpha 1; A disintegrin-like and metalloprotease (reprolysin type) with thrombospondin type 1 motif, 16; Collagen, type IV, alpha 4; Dentin matrix acidic phosphoprotein; Collagen, type IV, alpha 1; Thrombospondin repeat containing 1; Matrix metalloproteinase 16 (membrane-inserted); Collagen, type I, alpha 2; Fibulin 1; Tectorin beta; Glycosylphosphatidylinositol specific phospholipase D1; Upregulated in colorectal cancer gene 1). Cytoskeleton: (Filamin B, beta (actin binding protein 278); Centrin, EF-hand protein, 1; FERM domain containing 3; Bridging integrator 3; Parvin, gamma; Rho guanine nucleotide exchange factor (GEF) 11; Tyrosine kinase 2; Kelch-like 4 (Drosophila); Spectrin, beta, erythrocytic (includes spherocytosis, clinical type I); Arg/Abl-interacting protein ArgBP2; Advillin; Spectrin repeat containing, nuclear envelope 1; Catenin (cadherin-associated protein), delta 1; Erythrocyte membrane protein band 4.1 like 5; Catenin (cadherin-associated protein), alpha 2; Chemokine (C-C motif) ligand 3; Sarcoglycan, gamma (35 kDa dystrophin-associated glycoprotein); Nebulin; Thymosin, beta, identified in neuroblastoma cells; 3-phosphoinositide dependent protein kinase-1; Wiskott-Aldrich syndrome protein interacting protein; Dystonin; Huntingtin interacting protein 1; KIAA0316 gene product; Tropomodulin 4 (muscle); Deleted in liver cancer 1; Villin-like; Syntrophin, beta 1 (dystrophin-associated protein A1, 59 kDa, basic component 1); Protein kinase, cGMP-dependent, type I; Homo sapiens similar to keratin 8; cytokeratin 8; keratin, type II cytoskeletal 8 (LOC345751), mRNA; Adducin 1 (alpha); Protein kinase C and casein kinase substrate in neurons 3; Dystonin; Kell blood group; Filamin A interacting protein 1; Growth arrest-specific 2; Chromosome 1 open reading frame 1; Stathmin-like 2; Spectrin, alpha, erythrocytic 1 (elliptocytosis 2); FKSG44 gene; Kinesin family member 1C; Tensin; Kaptin (actin binding protein); Neurofibromin 2 (bilateral acoustic neuroma); Pleckstrin homology, Sec7 and coiled-coil domains 2 (cytohesin-2); Actin-related protein T1; Wiskott-Aldrich syndrome-like; Kelch-like 4 (Drosophila); Fascin homolog 1, actin-bundling protein (Strongylocentrotus purpuratus); Amphiphysin (Stiff-Man syndrome with breast cancer 128 kDa autoantigen); Polycystic kidney disease 2-like 1; Ankyrin 2, neuronal; CDC42 binding protein kinase alpha (DMPK-like); Hypothetical protein FLJ36144; Arg/Abl-interacting protein ArgBP2; Formin-like 3; Catenin (cadherin-associated protein), beta 1, 88 kDa; Profilin 2; Synaptopodin 2-like; Syntrophin, gamma 2; Phospholipase D2; Engulfment and cell motility 2 (ced-12 homolog, *C. elegans*); Neurofilament, light polypeptide 68 kDa; Dystonin; Actin-like 7B; Kinesin family member 1C; PDZ and LIM domain 3; Adducin 2 (beta); obscurin, cytoskeletal calmodulin and titin-interacting RhoGEF; Tubulin, beta polypeptide paralog; Filamin A interacting protein 1; Talin 1; *Homo sapiens* similar to [Segment 1 of 2] Piccolo protein (Aczonin) (LOC375597); CDC42 effector protein (Rho GTPase binding) 4; Syndecan 1; Filamin A, alpha (actin binding protein 280); Profilin 2; Tensin like C1 domain containing phosphatase; Hypothetical protein MGC33407; Rho family GTPase 1; Flavoprotein oxidoreductase MICAL2; Ca2+-dependent secretion activator; Rabphilin 3A-like (without C2 domains); Myosin XVA; Protein kinase, cGMP-dependent, type I; Myosin regulatory light chain interacting protein; Kinesin family member 13B; Muscle RAS oncogene homolog; Spectrin, beta, non-erythrocytic 1; TAO kinase 2; Filamin B, beta (actin binding protein 278); Neurofibromin 2 (bilateral acoustic neuroma); Catenin (cadherin-associated protein), alpha 3; obscurin, cytoskeletal calmodulin and titin-interacting RhoGEF; Coronin, actin binding protein, 1A; Erythrocyte membrane protein band 4.1-like 1; Spectrin, beta, non-erythrocytic 4; Thymosin, beta 4, Y-linked; Tektin 2 (testicular); Ras homolog gene family, member J; Serine/threonine kinase with Dbl- and pleckstrin homology domains; Dystrobrevin, beta; Actin, gamma 2, smooth muscle, enteric; Tara-like protein; Caspase 8, apoptosis-related cysteine protease; Kelch repeat and BTB (POZ) domain containing 10; Mucin 1, transmembrane; Microtubule-associated protein tau; Tensin; Ras homolog gene family, member F (in filopodia); Adducin 1 (alpha); Actinin, alpha 4; Erythrocyte membrane protein band 4.1 (elliptocytosis 1, RH-linked); Bicaudal D homolog 2 (*Drosophila*); Ankyrin 3, node of Ranvier (ankyrin G); Myosin VIIA (Usher syndrome 1B (autosomal recessive, severe)); Catenin (cadherin-associated protein), alpha 2; *Homo sapiens* similar to keratin 8, type II cytoskeletal—human (LOC285233); Fascin homolog 3, actin-bundling protein, testicular; Ras homolog gene family, member J; Beaded filament structural protein 2, phakinin; Desmin; Myosin X; Signal-induced proliferation-associated gene 1; Scinderin; Coactosin-like 1 (Dictyostelium); Engulfment and cell motility 2 (ced-12 homolog, *C. elegans*); Tubulin, beta 4; $Ca^{2+}$-dependent secretion activator; FERM domain containing 4A; Actin, alpha 1, skeletal muscle; Talin 1; Caldesmon 1; Filamin-binding LIM protein-1; Microtubule-associated protein tau; Syntrophin, alpha 1 (dystrophin-associated protein A1, 59 kDa, acidic component); Adducin 2 (beta); Filamin A interacting protein 1; PDZ and LIM domain 3; Erythrocyte membrane protein band 4.1 like 4B; FYN binding protein (FYB-120/130); Bridging integrator 3). Extracellular: (A disintegrin-like and metalloprotease (reprolysin type) with thrombospondin type 1 motif, 20; SPARC-like 1 (mast9, hevin); Serine (or cysteine) proteinase inhibitor, clade G (C1 inhibitor), member 1, (angioedema, hereditary); Urocortin; Chymotrypsin-like; Platelet-derived growth factor beta polypeptide (simian sarcoma viral (v-sis) oncogene homolog); BMP-binding endothelial regulator precursor protein; Complement factor H; Chorionic somatomammotropin hormone-like 1; Chemokine (C-C motif) ligand 18 (pulmonary and activation-regulated); Fibronectin 1; Pregnancy specific beta-1-glycoprotein 3; A disintegrin-like and metalloprotease (reprolysin type) with thrombospondin type 1 motif, 3; CocoaCrisp; Insulin-like 4 (placenta); Wingless-type MMTV integration site family, member 11; Cartilage oligomeric matrix protein; Transmembrane protease, serine 6; C-fos induced growth factor (vascular endothelial growth factor D); Family with sequence similarity 12, member B (epididymal); Protein phosphatase 1, regulatory subunit 9B, spinophilin; Transcobalamin II; macrocytic anemia; Coagulation factor V (proaccelerin, labile factor); Phospholipase A2, group IID; Tumor necrosis factor, alpha-induced protein 6; Collagen, type XV, alpha 1; Hyaluronan and proteoglycan link protein 3; collagen, type XIV, alpha 1 (undulin); Interleukin 19; Protease inhibitor 15; Cholinergic receptor, nicotinic, beta polypeptide 1 (muscle); Lysyl oxidase-like 3; Insulin-like growth factor binding protein 5; Growth hormone 1; Casein beta; NEL-like 2 (chicken); I factor (complement); Chemokine (C-C motif) ligand 23; Interferon, alpha 2; Matrix metalloproteinase 16 (membrane-inserted); Matrix metalloproteinase 12 (macrophage elastase); Glypican 5; Pregnancy specific beta-1-glycoprotein 3; Fibroblast growth factor 6; Gremlin 1 homolog, cysteine knot superfamily (*Xenopus laevis*); Protein S (alpha); Chondroitin beta1,4 N-acetylgalactosaminyl-transferase; Glycosylphosphatidylinositol specific phospholipase D1; Fibroblast growth factor 1 (acidic); Spondin 1, extracellular matrix protein; Bone morphogenetic protein 1; Surfactant, pulmonary-associated protein B; Dentin matrix acidic phosphoprotein; Lipoprotein, Lp(a); Mucin 1, transmembrane; Mannan-binding lectin serine protease 1 (C4/C2 activating component of Ra-reactive factor); Meprin A, beta; Secretoglobin, family 1D, member 1; Asporin (LRR class 1); Chemokine (C-C motif) ligand 25; Cytokine-like protein C17; Insulin-like 5; Meprin A, alpha (PABA peptide hydrolase); Scrapie responsive protein 1; Fibroblast growth factor 18; Chemokine (C-X-C motif) ligand 9; Inhibin, beta B (activin AB beta polypeptide); Fibroblast growth factor 8 (androgen-induced); Granulysin; Cocaine- and amphetamine-regulated transcript; Collagen, type I, alpha 2; Chemokine (C-C motif) ligand 17; Chemokine (C-C motif) ligand 23; Sparc/osteonectin, cwcv and kazal-like domains proteoglycan (testican) 3; Gamma-aminobutyric acid (GABA) A receptor, beta 3; Defensin, alpha 4, corticostatin; Leucine rich repeat neuronal 3; Glypican 6; Mitogen-activated protein kinase kinase 2; Coagulation factor XI (plasma thromboplastin antecedent); Chemokine (C-C motif) ligand 5; Dystonin; Frizzled-related protein; Coagulation factor XIII, A1 polypeptide; Insulin-like growth factor 1 (somatomedin C); Hypothetical protein MGC45438; Sperm associated antigen 11; Insulin-like growth factor 1 (somatomedin C); Periostin, osteoblast specific factor; Alpha-2-macroglobulin; Gamma-aminobutyric acid (GABA) A receptor, alpha 5; Serine (or cysteine) proteinase inhibitor, clade A (alpha-1 antiproteinase, antitrypsin), member 3; Silver homolog (mouse); Frizzled-related protein; Chondroadherin; Chondroitin beta1,4 N-acetylgalactosaminyltransferase; 5-hydroxytryptamine (serotonin) receptor 3, family member C; Collagen, type VI, alpha 2; Toll-like receptor 9; Amelogenin, Y-linked; Vascular endothelial growth factor B; Radial spokehead-like 1; Fms-related tyrosine kinase 1 (vascular endothelial growth factor/vascular permeability factor receptor); Protease inhibitor 16; Interleukin 2; Clusterin (complement lysis inhibitor, SP-40,40, sulfated glycoprotein 2, testosterone-repressed prostate message 2, apolipoprotein J); Follicle stimulating hormone, beta polypeptide; A disintegrin-like and metalloprotease (reprolysin type) with thrombospondin type 1 motif, 16; Lysozyme (renal amyloidosis); radical fringe homolog (*Drosophila*); Insulin-like growth factor binding protein 5; Taxilin; Apolipoprotein A-V; Platelet derived growth factor C; Chemokine (C-C motif) ligand 3-like 1; Fibroblast growth factor 16; Collagen, type VI, alpha 2; Serine (or cysteine) proteinase inhibitor, clade C (antithrombin), member 1; Chemokine (C-C motif) ligand 11; Collagen, type IV, alpha 4; Bruton agammaglobulinemia tyrosine kinase; Insulin-like growth factor 2 (somatomedin A); Kazal-type serine protease inhibitor domain 1; Fibrinogen, A alpha polypeptide; Chemokine (C-C motif) ligand 1; Inhibin, beta E; Sex hormone-binding globulin; Collagen, type IV, alpha 1; Lecithin-cholesterol acyltransferase; Cysteine-rich secretory protein 2; Hyaluronan and proteoglycan link protein 1; Natriuretic peptide precursor C; Ribonuclease, RNase A family, k6; Fibroblast growth factor 14; ADAMTS-like 2; Collagen, type IV, alpha 3 (Goodpasture antigen); Angiopoietin 2; Apolipoprotein L, 3; Chemokine (C-X-C motif) ligand 12 (stromal cell-derived factor 1); Hyaluronan binding protein 2; Coagulation factor VII (serum prothrombin conversion accelerator); collagen, type XIV, alpha 1 (undulin); Oviductal glycoprotein 1, 120 kDa (mucin 9, oviductin); Matrilin 1, cartilage matrix protein; mucin 5, subtypes A and C, tracheobronchial/gastric; Tumor necrosis factor receptor superfamily, member 11 b (osteoprotegerin); Transglutaminase 2 (C polypeptide, protein-glutamine-gamma-glutamyltransferase); Keratocan; Collagen, type V, alpha 3; WAP four-disulfide core domain 2; Chemokine (C-X3-C motif) ligand 1; Serine (or cysteine) proteinase inhibitor, clade D (heparin cofactor), member 1; Secretory protein LOC348174; Coagulation factor X; Interleukin 16 (lymphocyte chemoattractant factor); Pancreatic lipase-related protein 2; HtrA serine peptidase 3; Glycine receptor, alpha 3; CD5 antigen-like (scavenger receptor cysteine rich family); Hypothetical protein MGC39497; Coagulation factor VIII, procoagulant component (hemophilia A); Dermatopontin; Noggin; Secreted LY6/PLAUR domain containing 1; ADAMTS-like 1; Alpha-1-B glycoprotein; Chromosome 20 open reading frame 175; Wingless-type MMTV integration site family, member 8B; Fibulin 1; Fibulin 5; Cathepsin S; Nidogen (enactin); Chemokine (C-C motif) ligand 26; Endothelial cell-specific molecule 1; Chitinase 3-like 1 (cartilage glycoprotein-39); Gamma-aminobutyric acid (GABA) A receptor, beta 1; Secretoglobin, family 1D, member 2; Mannan-binding lectin serine protease 1 (C4/C2 activating component of Ra-reactive factor); ADAMTS-like 1; Sema domain, immunoglobulin domain (Ig), and GPI membrane anchor, (semaphorin) 7A; A disintegrin-like and metalloprotease (reprolysin type) with thrombospondin type 1 motif, 15; Proprotein convertase subtilisin/kexin type 2; Insulin-like growth factor 1 (somatomedin C); Retinoschisis (X-linked, juvenile) 1; A disintegrin-like and metalloprotease (reprolysin type) with thrombospondin type 1 motif, 16; Chemokine (C motif) ligand 2; Fibroblast growth factor 5; Sperm associated antigen 11; Microfibrillar-associated protein 4; Poliovirus receptor; Extracellular signal-regulated kinase 8; Transmembrane protease, serine 6; Protein kinase C, alpha; Chitinase 3-like 2; Interleukin 9; Apolipoprotein L, 6; Surfactant, pulmonary-associated protein A1; Collagen, type VI, alpha 1; Apolipoprotein L, 6; Hypothetical protein FLJ13710; Carboxypeptidase B2 (plasma, carboxypeptidase U); Bactericidal/permeability-increasing protein-like 2; Fibroblast growth factor 5; Secreted phosphoprotein 1 (osteopontin, bone sialoprotein I, early T-lymphocyte activation 1); HtrA serine peptidase 3; Deleted in liver cancer 1; Endothelial cell-specific molecule 1; Von Willebrand factor; A disintegrin-like and metalloprotease (reprolysin type) with thrombospondin type 1 motif, 5 (aggrecanase-2); Sema domain, immunoglobulin domain (Ig), short basic domain, secreted, (semaphorin) 3A; Chemokine (C-X-C motif) ligand 12 (stromal cell-derived factor 1); Statherin; Extracellular signal-regulated kinase 8; Tissue inhibitor of metalloproteinase 3 (Sorsby fundus dystrophy, pseudoinflammatory); Platelet factor 4 (chemokine (C-X-C motif) ligand 4); Surfactant, pulmonary-associated protein D; Complement factor H; Delta-like 1 homolog (*Drosophila*); WAP four-disulfide core domain 1; Insulin-like growth factor binding protein, acid labile subunit; Breast cancer 2, early onset; Pre-B lymphocyte gene 1; Corticotropin releasing hormone; Hypothetical protein DKFZp434B044; Prolactin-induced protein; RAS guanyl releasing protein 4; Progastricsin (pepsinogen C); Sema domain, immunoglobulin domain (Ig), short basic domain, secreted, (semaphorin) 3F; Upregulated in colorectal cancer gene 1; Proteoglycan 4; Cholinergic receptor, nicotinic, delta polypeptide; Cartilage oligomeric matrix protein; ABO blood group (transferase A, alpha 1-3-N-acetylgalactosaminyltransferase; transferase B, alpha 1-3-galactosyltransferase); Interleukin 12A (natural killer cell stimulatory factor 1, cytotoxic lymphocyte maturation factor 1, p35); Fibroblast growth factor 7 (keratinocyte growth factor); Kin of IRRE like 3 (*Drosophila*); Cholinergic receptor, nicotinic, alpha polypeptide 2 (neuronal); Palate, lung and nasal epithelium carcinoma associated; Collagen, type XV, alpha 1; Pleiotrophin (heparin binding growth factor 8, neurite growth-promoting factor 1); Angiopoietin-like 2; Norrie disease (pseudoglioma); Chemokine (C-C motif) ligand 3; Chitinase 3-like 1 (cartilage glycoprotein-39); Inter-alpha (globulin) inhibitor H3; Amelogenin (amelogenesis imperfecta 1, X-linked); Epidermal growth factor (beta-urogastrone); Fibroblast growth factor 13; Wingless-type MMTV integration site family, member 7B; Cholinergic receptor, nicotinic, gamma polypeptide; Pregnancy specific beta-1-glycoprotein 6; Matrix metalloproteinase 14 (membrane-inserted); Chemokine (C-C motif) ligand 26; Interferon, alpha 6; Tachykinin, precursor 1 (substance K, substance P, neurokinin 1, neurokinin 2, neuromedin L, neurokinin alpha, neuropeptide K, neuropeptide gamma); Secreted frizzled-related protein 5; Hyaluronan and proteoglycan link protein 4; Complement component 4B; Matrix metalloproteinase 16 (membrane-inserted); Fibroblast growth factor 7 (keratinocyte growth factor); Apolipoprotein C-II; Chloride channel, calcium activated, family member 3; Tetranectin (plasminogen binding protein); Collagen, type III, alpha 1 (Ehlers-Danlos syndrome type IV, autosomal dominant); KIAA0556 protein; Chemokine (C-C motif) ligand 4; Hemopexin; Inter-alpha (globulin) inhibitor H1; Relaxin 1; Matrix Gla protein; A disintegrin-like and metalloprotease (reprolysin type) with thrombospondin type 1 motif, 2; Interferon (alpha, beta and omega) receptor 2; Acid phosphatase, prostate; Guanine nucleotide binding protein (G protein), gamma 8; Matrix metalloproteinase 23B; Meprin A, alpha (PABA peptide hydrolase); Hyaluronoglucosaminidase 1; Angiotensinogen (serine (or cysteine) proteinase inhibitor, clade A (alpha-1 antiproteinase, antitrypsin), member 8); Cartilage intermediate layer protein, nucleotide pyrophosphohydrolase; Purinergic receptor P2X, ligand-gated ion channel, 7; Glypican 3; Tectorin beta; Interferon, alpha 5; Lipocalin 7; Platelet factor 4 variant 1; Nucleobindin 1; Collagen, type XI, alpha 1; Gastric inhibitory polypeptide; Thrombospondin repeat containing 1; 5-hydroxytryptamine (serotonin) receptor 3 family member D; Collagen, type XXV, alpha 1; Growth differentiation factor 9; Hypothetical protein DKFZp434B044; Endothelin 3; Chemokine (C motif) ligand 2; Prokineticin 2; Tumor necrosis factor receptor superfamily, member 11b (osteoprotegerin); Tissue inhibitor of metalloproteinase 2; Dystonin; Chromogranin B (secretogranin 1); Hyaluronan and proteoglycan link protein 2; Leucine rich repeat neuronal 3; Lumican; Matrilin 1, cartilage matrix protein; Phospholipase A2, group IIA (platelets, synovial fluid); Carboxylesterase 1 (monocyte/macrophage serine esterase 1); Sparc/osteonectin, cwcv and kazal-like domains proteoglycan (testican); Dickkopf homolog 2 (*Xenopus laevis*); Gamma-aminobutyric acid (GABA) A receptor, alpha 3; Pregnancy specific beta-1-glycoprotein 11; Insulin-like growth factor binding protein 1; Defensin, beta 106; Interleukin 17F; Ligand-gated ion channel subunit; Phospholipase A2 receptor 1, 180 kDa; I factor (complement); Dystonin; LAG1 longevity assurance homolog 1 (*S. cerevisiae*); Prolactin; Testis expressed sequence 264; Sema domain, immunoglobulin domain (Ig), short basic domain, secreted, (semaphorin) 3D; secreted frizzled-related protein 2; secreted frizzled-related protein 4).

There are groups of genes present only in UCEC. These genes are related to the following: Homeostasis (Albumin; Calcium-sensing receptor; Aquaporin 9; Lactotransferrin. Morphogenesis: Homeo box HB9; Epithelial V-like antigen 1). Embryonic Development (Relaxin 2; Carcinoembryonic antigen-related cell adhesion molecule 8; Indoleamine-pyrrole 2,3 dioxygenase; EPH receptor A3; Thyrotrophic embryonic factor; Pregnancy specific beta-1-glycoprotein 1; Laminin, alpha 3), the Extracellular Space (Surfactant, pulmonary-associated protein A1; Pregnancy specific beta-1-glycoprotein 1; Lactotransferrin; TGF-alpha; Albumin; FGF-23; S100 calcium binding protein A9 (calgranulin B)), the Extracellular Matrix (Laminin, beta 4; Laminin, alpha 3; Zona pellucida glycoprotein 4. Structural Molecule Activity: Chromosome 21 open reading frame 29; Laminin, alpha 3; Microtubule-associated protein 2; Laminin, beta 4; Keratin 6B; Ladinin 1; Keratin 6A; Occludin; Loricrin; Erythrocyte membrane protein band 4.1 (elliptocytosis 1, RH-linked); Crystallin, beta A2; eye lens structural protein; Contactin associated protein-like 4; Claudin 19; Hypothetical protein LOC144501; Keratin 6E; Keratin 6L; Lens intrinsic membrane protein 2, 19 kDa), the Cytoskeleton (Microtubule-associated protein 2; Erythrocyte membrane protein band 4.1 like 5; *Homo sapiens* trichohyalin (THH); Keratin 6B; Keratin 6A; Epithelial V-like antigen 1; Hook homolog 1 (*Drosophila*); Loricrin; Erythrocyte membrane protein band 4.1 (elliptocytosis 1, RH-linked); Tropomodulin 1; MAP/microtubule affinity-regulating kinase 1; Keratin 6E; Actin binding LIM protein family, member 2), Cell Adhesion Molecules (Cadherin 19, type 2; Myeloid/lymphoid or mixed-lineage leukemia; Chromosome 21 open reading frame 29; Kin of IRRE like 2; Laminin, alpha 3; Sialoadhesin; CD84 antigen (leukocyte antigen); Lectin, galactoside-binding, soluble, 2 (galectin 2); Epithelial V-like antigen 1; CD96 antigen; Tubulointerstitial nephritis antigen; Carcinoembryonic antigen-related cell adhesion molecule 8; IL-18; Immunoglobulin superfamily, member 1; Integrin, beta 8; Ornithine arbamoyltransferase; Integrin, beta 6; Contactin associated protein-like 4; Collagen, type XVII, alpha 1; Cadherin-like 26; Mucin and cadherin-like), Cell Differentiation proteins (Protein tyrosine phosphatase, receptor-type, Z polypeptide 1; Laminin, alpha 3; CD84 antigen (leukocyte antigen); EDRF2; *Homo sapiens* erythroid differentiation-related factor 2; Tumor protein p73-like; NB4 apoptosis/differentiation related protein; *Homo sapiens* PNAS-133; Similar to seven in absentia 2; Interleukin 24; Keratin 6B; Keratin 6A; Dehydrogenase/reductase (SDR family) member 9; Gap junction protein, beta 5 (connexin 31.1); Iroquois homeobox protein 4; Ventral anterior homeobox 2; Chemokine (C-X-C motif) ligand 10; Tumor necrosis factor receptor superfamily, member 17; Calcium channel, voltage-dependent, beta 2 subunit; Parkinson disease (autosomal recessive, juvenile) 2, parkin; Kallikrein 7 (chymotryptic, stratum corneum); Glial cells missing homolog 2; AP-2 alpha; Protein tyrosine phosphatase, receptor-type, Z polypeptide 1; Troponin T1; Sciellin; Glucosaminyl (N-acetyl) transferase 2, I-branching enzyme; Collagen, type XVII, alpha 1; Suppressor of cytokine signaling 2; Distal-less homeo box 1; Zygote arrest 1; Interleukin 20; Growth differentiation factor 3; FGF-23; Wingless-type MMTV integration site family, member 8A. Extracellular: Chromosome 21 open reading frame 29; Laminin, alpha 3; Laminin, beta 4; Interleukin 24; Pregnancy specific beta-1-glycoprotein 1; Chemokine (C-X-C motif) ligand 11; Surfactant, pulmonary-associated protein A1; Prepronociceptin; 5-hydroxytryptamine (serotonin) receptor 3B; Carcinoembryonic antigen-related cell adhesion molecule 8; Chemokine (C-X-C motif) ligand 10; IL-18 (interferon-gamma-inducing factor); Lactotransferrin; Albumin; Fas ligand (TNF superfamily, member 6); Cholinergic receptor, nicotinic, beta polypeptide 4; Cathelicidin antimicrobial peptide; Airway trypsin-like protease; S100 calcium binding protein A9 (calgranulin B); TGF-alpha; Kallikrein 10; Serine protease inhibitor, Kunitz type 1; WNT1 inducible signaling pathway protein 3; Relaxin 2; Interferon, kappa; Defensin, beta 103A; IL-20; Zona pellucida glycoprotein 4; Growth differentiation factor 3; FGF-23; Wingless-type MMTV integration site family, member 8A; Complement factor H-related 5), Developmental proteins (EPH receptor A3; NIMA (never in mitosis gene a)-related kinase 2; Zinc finger protein 282; TANK-binding kinase 1; MRE11 meiotic recombination 11 homolog A; E2F transcription factor 2; Protein tyrosine phosphatase, receptor-type, Z polypeptide 1; *Homo sapiens* clone 161455 breast expressed mRNA from chromosome X; Laminin, alpha 3; v-myb myeloblastosis viral oncogene homolog (avian)-like 1; Regulator of G-protein signalling 11; Microtubule-associated protein 2; Transmembrane protein 16A; Adenomatosis polyposis *coli* 2; Homeo box HB9; Centromere protein F, 350/400 ka (mitosin); CD84 antigen (leukocyte antigen); EDRF2; *Homo sapiens* erythroid differentiation-related factor 2; Tumor protein p73-like; NB4 apoptosis/differentiation related protein; *Homo sapiens* PNAS-133; Forkhead box P2; *Homo sapiens* gastric-associated differentially-expressed protein YA61 P (YA61); Tenascin N; Chromosome 6 open reading frame 49; Zinc finger protein 462; Zinc finger protein 71 (Cos26); SRY (sex determining region Y)-box 7; Triggering receptor expressed on myeloid cells-like 4; Interleukin 24; Pregnancy specific beta-1-glycoprotein 1; Chondroitin sulfate proteoglycan 5 (neuroglycan C); Keratin 6B; Keratin 6A; Dehydrogenase/reductase (SDR family) member 9; Epithelial V-like antigen 1; Gap junction protein, beta 5 (connexin 31.1); G protein-coupled receptor 51; Interferon regulatory factor 6; Neurotrophin 5 (neurotrophin 4/5); CD96 antigen; Iroquois homeobox protein 4; Interleukin 1 receptor-like 1; G-2 and S-phase expressed 1; Nuclear receptor subfamily 2, group E, member 3; Ventral anterior homeobox 2; Zinc finger protein 215; DNA segment on chromosome 4 (unique) 234 expressed sequence; Carcinoembryonic antigen-related cell adhesion molecule 8; Chemokine (C-X-C motif) ligand 10; IL-18; Indoleamine-pyrrole 2,3 dioxygenase; Albumin; Calcium-sensing receptor (hypocalciuric hypercalcemia 1, severe neonatal hyperparathyroidism); Fas ligand (TNF superfamily, member 6); TNFR superfamily, member 17; Calcium channel, voltage-dependent, beta 2 subunit; Parkinson disease (autosomal recessive, juvenile) 2, parkin; Kallikrein 7 (chymotryptic, stratum corneum); Glial cells missing homolog 2; TGF-alpha; Thyrotrophic embryonic factor; AP-2 alpha (activating enhancer binding protein 2 alpha); Kallikrein 10; Regulator of G-protein signalling 7; Protein tyrosine phosphatase, receptor-type, Z polypeptide 1; Serine protease inhibitor, Kunitz type 1; WNT1 inducible signaling pathway protein 3; Zic family member 3 heterotaxy 1 (odd-paired homolog, *Drosophila*); TTK protein kinase; Troponin T1, skeletal, slow; Sciellin; TGFB-induced factor 2-like, X-linked; Kallikrein 8 (neuropsin/ovasin); Glucosaminyl (N-acetyl) transferase 2, I-branching enzyme; Ankyrin repeat domain 30A; Relaxin 2; Collagen, type XVII, alpha 1; Gene differentially expressed in prostate; Phosphatase and actin regulator 3; Suppressor of cytokine signaling 2; Nuclear receptor subfamily 4, group A, member 3; Angiotensin I converting enzyme (peptidyl-dipeptidase A) 1; Hypothetical protein MGC17986; Distal-less homeo box 1; LAG1 longevity assurance homolog 3 (*S. cerevisiae*); Zygote arrest 1; Interferon, kappa; IL-20; ICEBERG caspase-1 inhibitor; Growth differentiation factor 3; FGF-23; Testis expressed sequence 15; Wingless-type MMTV integration site family, member 8A; SRY (sex determining region Y)-box 7; Carnitine deficiency-associated, expressed in ventricle 1; Prokineticin 1; CAMP responsive element binding protein 3-like 3; Caspase recruitment domain family, member 15; FLJ23311 protein).

Example 6

Direct Differentiation of Umbilical Cord Epithelial Stem Cells (UCEC) into Skin Epidermal Keratinocytes For differentiation into skin epidermal keratinocytes, umbilical cord epithelial stem cells, UCEC cells, were cultured according to a standard protocol for the cultivation of keratinocytes. Cell isolation techniques were as described above. UCEC were then cultured in serum-free keratinocyte growth media, KGM, KGM-2 (Cambrex), EpiLife (Cascade Biologics) or in Green's medium in the presence of irradiated or Mytomycin-C treated 3T3 mouse embryonic feeder layer at 37° C., 5% $CO_2$). UCEC cell morphology thus differentiated resembled human epidermal keratinocytes. Epithelial cells have similar morphology under light microscope and can be easily turned into fibroblasts using conventional and commercially available media (cf., FIG. 2).

Immunofluorescent analysis shows that the cultivated UCEC also express epidermal keratinocyte molecular markers such as keratins, desmosome, hemidesmosome and basement membrane components (see also FIG. 10 that shows that UCEC are qualified to be epithelial cells in general by expressing a variety of these epithelial cell markers). Accordingly, these results show that umbilical cord epithelial progenitor/stem cells of the present invention can be differentiated into skin cells such as epidermal keratinocytes which can be used for wound healing and have great potential for the development of cultured skin equivalents.

Example 7

Figures 9, 10, 11, 12, 13, 14, 15, 16:
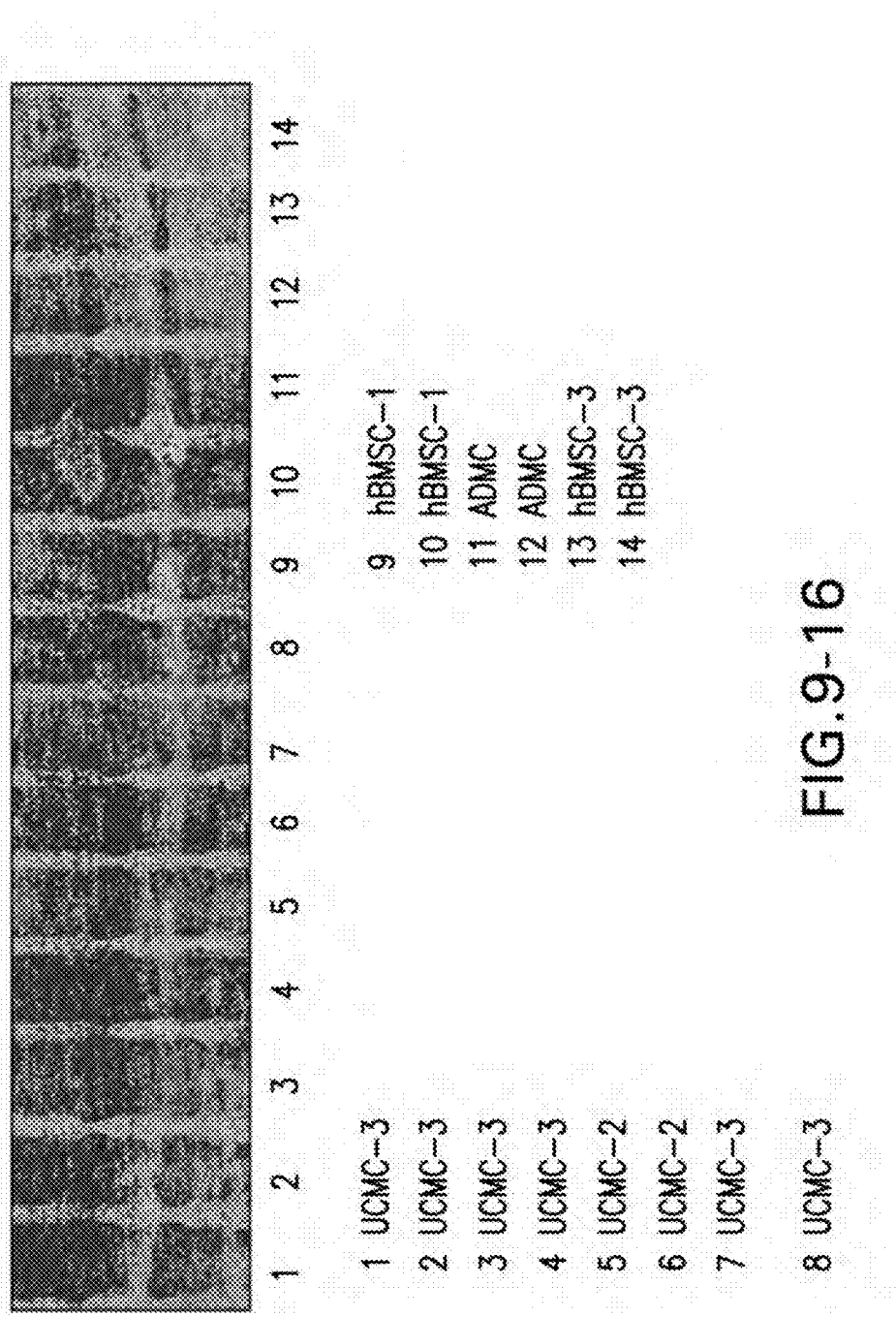

Expansion of Umbilical Cord Epithelial and Mesenchymal Stem Cells Using Repetitive Tissue Explants of Umbilical Cord Lining Membrane Tissues Umbilical cord epithelial and mesenchymal stem cells of the invention were expanded using repetitive explants of umbilical cord amniotic membrane tissue as follows. Briefly, at day 1 of process, tissue explants were plated onto tissue culture dishes in growth media (DMEM/10% FCS, EpiLife, KGM, KGM-2 or M171) at 37° C., 5% $CO_2$; media was changed every 2 or 3 days. Cell outgrowths started and continued migrating from the explants for 7 days. After that, tissue explants were transferred to other dishes to allow further cell outgrowth. This process was continued until the explants had diminished in size, preventing further explanation. In this connection it is noted that the explants progressively shrink in size until they are too small for further tissue explant since during the process of cells outgrowing and migrating from tissue explants, the cells produce proteases to digest and break down tissue. FIG. 16 schematically illustrates the rapid and robust expansion process of umbilical cord epithelial and mesenchymal stem cells achieved using this protocol. Thus, this study demonstrates the high yield of UCMC and UMEC cells can be obtained from this source, further reflecting the high viability and pro-growth characteristics oft these cells in comparison with other sources of cells as bone-marrow or adipose-derived stem cells. In addition, being a solid tissue, the successful repetitive explant technique used herein demonstrates that the cells of the invention can be uniformly extracted from the entire tissue instead of only certain portions. This allows the maximum number of cells that can be derived at a low passage instead of passing the cells through many generations causing deterioration of cells.

Example 8

Direct Differentiation of Umbilical Cord Mesenchymal Cells (UCMC) into Skin Dermal Fibroblasts For differentiation into skin dermal fibroblasts, umbilical cord mesenchymal stem cells, UCMC cells were cultured according to a standard protocol for the cultivation of fibroblasts. Cell isolation techniques were as described above in Example 6. UCMC were then cultured in DMEM or commercially available fibroblast growth media (FGM). UCMC cell morphology thus differentiated resembled human dermal fibroblasts. Mesenchymal cells have similar morphology under light microscope and can be easily turned into fibroblasts using conventional and commercially available media (cf., FIG. 3).

Example 9

Figures 9, 10, 11, 12, 13, 14, 15, 16, 17:
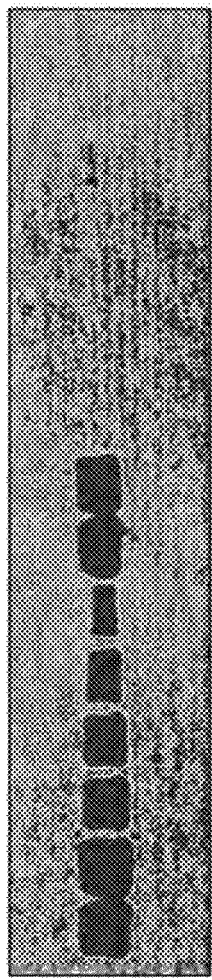
Figures 9, 10, 11, 12, 13, 14, 15, 16, 17, 18:
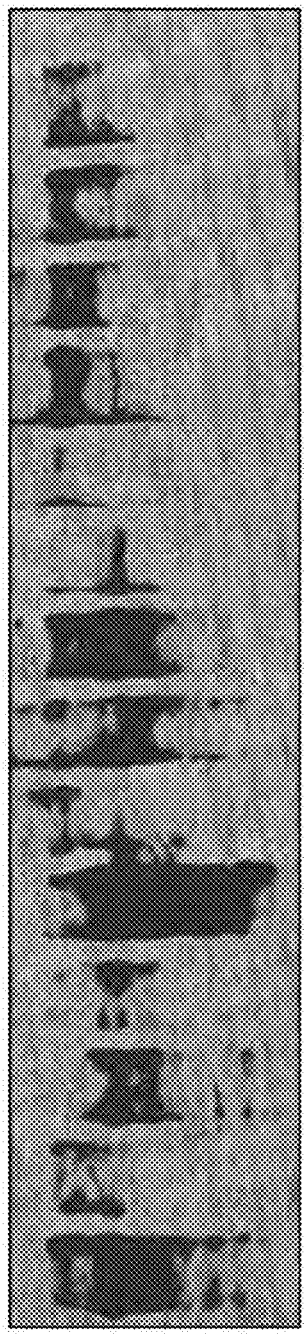
Figures 9, 10, 11, 12, 13, 14, 15, 16, 17, 18, 19:
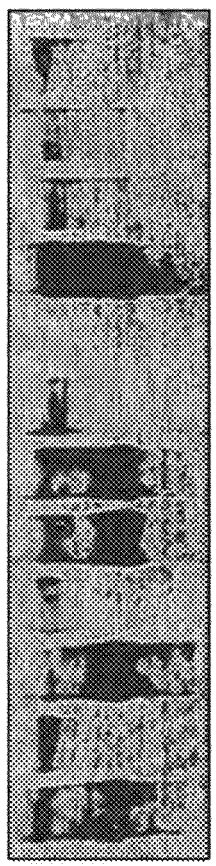
Figures 9, 10, 11, 12, 13, 14, 15, 16, 17, 18, 19, 20:
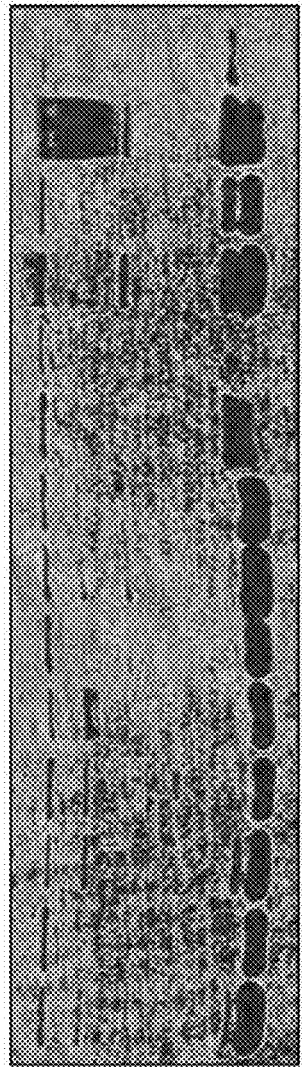
Figures 9, 10, 11, 12, 13, 14, 15, 16, 17, 18, 19, 20, 21:
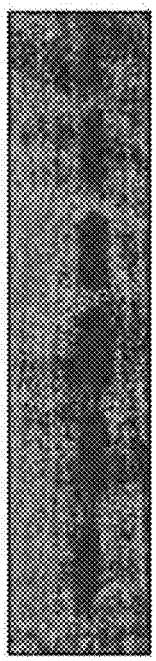
Figures 9, 10, 11, 12, 13, 14, 15, 16, 17, 18, 19, 20, 21, 22:
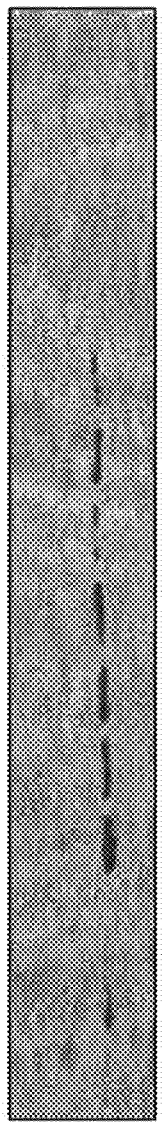
Figures 9, 10, 11, 12, 13, 14, 15, 16, 17, 18, 19, 20, 21, 22, 23:
Figures 9, 10, 11, 12, 13, 14, 15, 16, 17, 18, 19, 20, 21, 22, 23, 24:
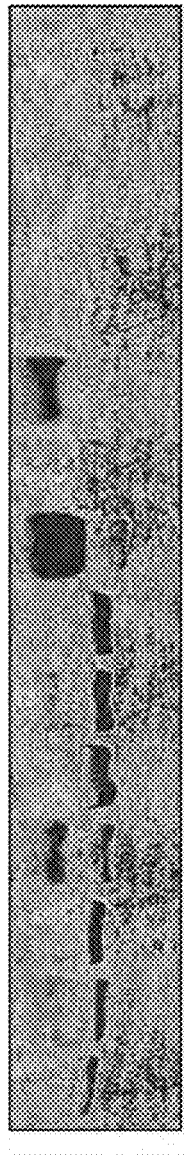
Figures 9, 10, 11, 12, 13, 14, 15, 16, 17, 18, 19, 20, 21, 22, 23, 24, 25:
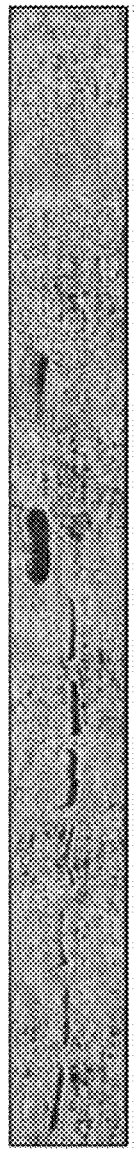
Figures 9, 10, 11, 12, 13, 14, 15, 16, 17, 18, 19, 20, 21, 22, 23, 24, 25, 26:
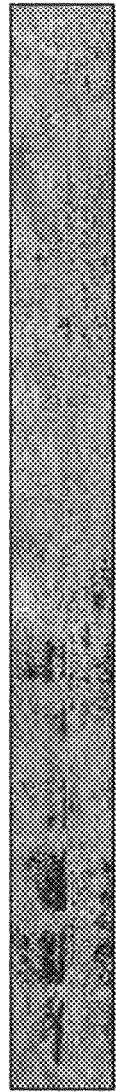
Figures 9, 10, 11, 12, 13, 14, 15, 16, 17, 18, 19, 20, 21, 22, 23, 24, 25, 26, 27:
Figures 9, 10, 11, 12, 13, 14, 15, 16, 17, 18, 19, 20, 21, 22, 23, 24, 25, 26, 27, 28:
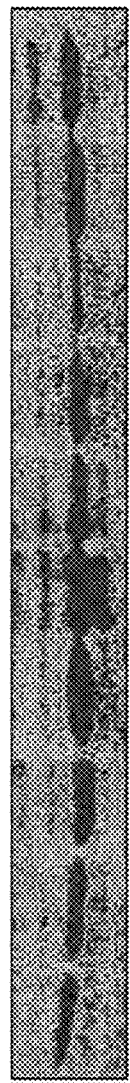
Figures 9, 10, 11, 12, 13, 14, 15, 16, 17, 18, 19, 20, 21, 22, 23, 24, 25, 26, 27, 28, 29:
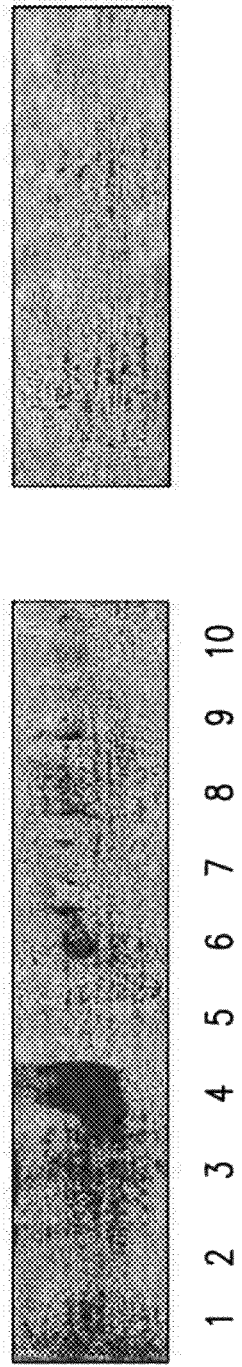

Direct Differentiation of Epithelial Stem/progenitor Cells into Skin Epidermal Keratinocytes In an approach similar to Example 6, epithelial stem/progenitor cells of the amniotic membrane of the umbilical cord (UCEC) were isolated as described in Example 2. For differentiation of UCEC into epidermal keratinocytes, the cells were cultured in keratinocyte media (EpiLife or KGM) until 100% (cultivation after 5 days shown in FIG. 17-A) confluent before changing the media to DMEM/10% FCS for 3 days to form epidermal cell sheets. As shown in FIG. 17-A (in which photographs of two experiments termed "UCEC-10" and UCEC-17 are depicted), after cultivation in DMEM/10% FCS, UCEC, had differentiated into epidermal keratinocytes that formed cell sheets (photograph of FIG. 17-A taken after 10 days). These results thus provide further evidence for the pluripotency of the cells of the present invention.

Example 10

Direct Differentiation of Mesenchymal Stem/progenitor Cells into Osteoblasts

Mesenchymal stem/progenitor cells of the amniotic membrane of the umbilical cord (UCMC) were isolated as described in Example 2. For differentiation of UCMC into osteoblasts, cells were cultured in DMEM/10% FCS until 100% confluent, and then in starvation medium of serum-free DMEM for another 48 hours. UCMC were subjected to osteogenic induction media for 4 weeks before subjecting the cells to von Kossa staining (bone cell staining). The osteogenic induction medium contained DMEM/10% FCS; 1% antibiotic (streptomycin and penicillin)/antimycotic (fungizone); 0.01 μM 1,25-dihydroxyvitamin D3, 50 μM ascorbate-2-phosphate, 10 mM β-glycerophosphate, 1% antibiotic (streptomycin and penicillin)/antimycotic (fungizone).

Figure 17A:
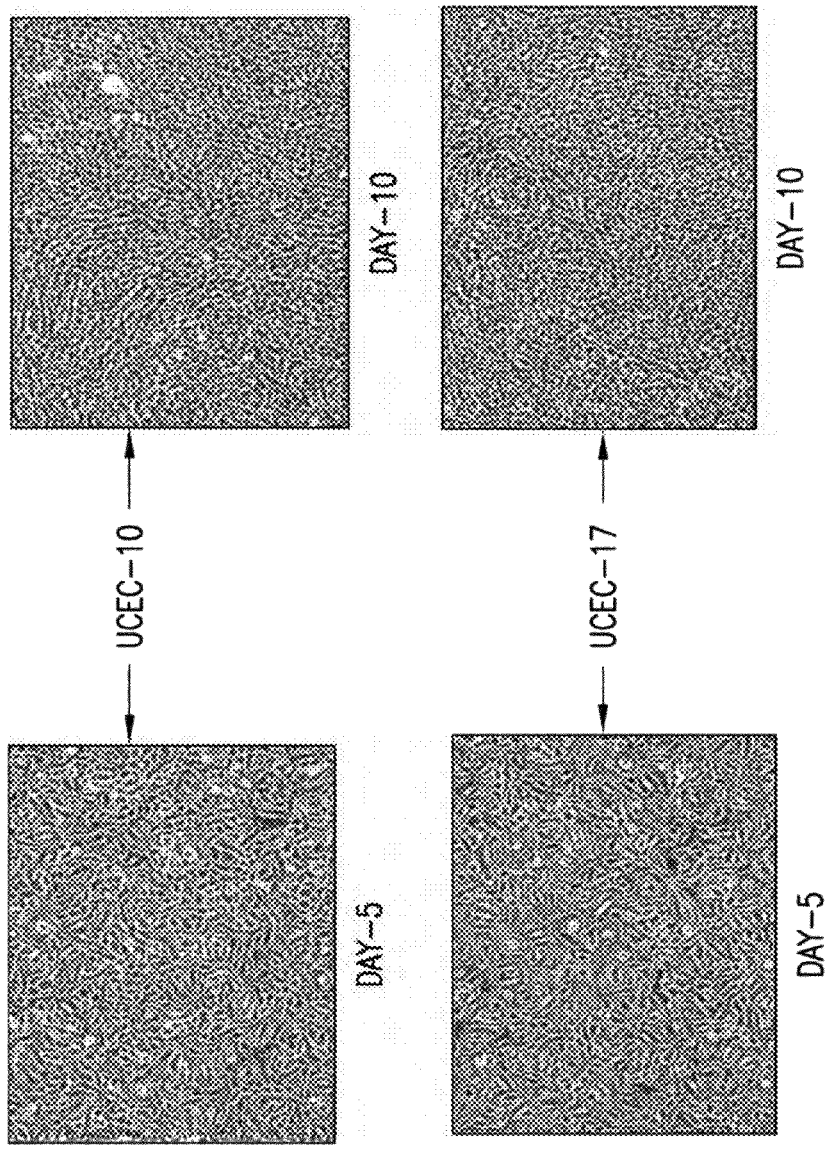
FIG. 17A depicts direct (in-vitro) differentiation of epithelial cells isolated from the amniotic membrane of umbilical cord (UCEC) into skin epidermal keratinocytes.
Figure 17B:
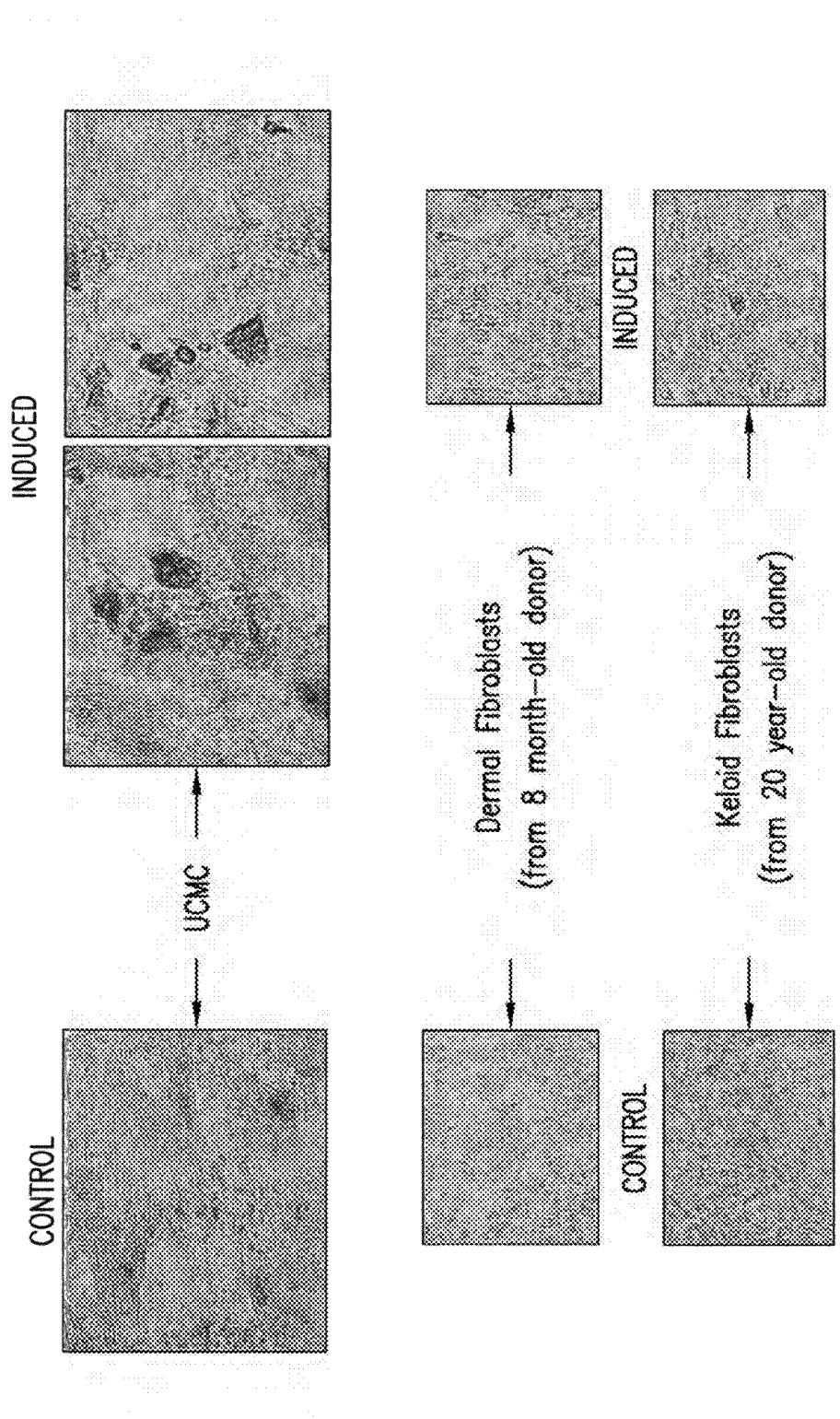
FIG. 17B depicts in-vitro differentiation of mesenchymal cells isolated from the amniotic membrane of umbilical cord (UCMC) into osteoblasts.

As shown in FIG. 17B, von Kossa staining of UCMC cells that were cultivated in the osteogenic induction medium indicated bone nodule formation in the UCMC and thus differentiation of the UCMC into osteoblasts whereas no such differentiation was indicated in untreated UCMC which were cultured in DMEM/10% FCS without induction under otherwise same conditions as negative control. As a further negative control, dermal fibroblasts from an 8 months old donor and keloid fibroblasts from an 20 year old donor were cultivated under the same conditions as the induced or un-induced UCMC. Both cell types did not yield a positive result using von Kossa staining, which is a further evidence for the pluripotency of UCMC of the present invention and thus to differentiate, for example, also into osteoblasts.

Example 11

Direct Differentiation of Mesenchymal Stem/progenitor Cells into Adipocytes

Mesenchymal stem/progenitor cells from the amniotic membrane of the umbilical cord (UCMC) were isolated as described in Example 2. For differentiation of UCMC into adipocytes, cells were cultured in DMEM/10% FCS until 100% confluent, and then in starvation medium of serum-free DMEM for another 48 hours. UCMC were subjected to adipogenic induction media for 4 weeks before subjecting the cells to Oil-Red-O staining. The adipogenic induction medium contained DMEM/10% FCS; 1% antibiotic (streptomycin and penicillin)/antimycotic (fungizone)); 0.5 mM isobutyl-methylxanthine (IBMX), 1 μM dexamethasone, 10 μM insulin, and 200 μM indomethacin.

Oil-Red-O staining of UCMC cells that were cultivated in the adipogenic induction medium indicated fat accumulation in the UCMC and thus differentiation of the UCMC into adipocytes whereas no such differentiation was indicated in untreated UCMC which were cultured in DMEM/10% FCS without induction under otherwise same conditions as negative control. As a further negative control, dermal fibroblasts from an 8 month old donor and keloid fibroblasts from a 20 year old donor were cultivated under the same conditions as the induced or un-induced UCMC. Both cell types did not yield a positive result in the staining with Oil-Red-O, which is a further evidence for the pluripotency of UCMC of the present invention and to differentiate, for example, also into adipocytes.

What is claimed is:

1. A method of treating a subject having a disorder comprising:
administering to the subject an effective amount of an epithelial or mesenchymal stem/progenitor cell isolated from the amniotic membrane of the umbilical cord or an effective amount of a cellular extract thereof, wherein the cellular extract contains growth factors and peptides and is in the form of a supernatant into which the epithelial or mesenchymal stem/progenitor cell secretes the growth factors and peptides, wherein the epithelial or mesenchymal stem/progenitor cell expresses the following genes: POU5f1, Bmi-1, leukemia inhibitory factor (LIF), and secretes Activin A and Follistatin, wherein the disorder is a wound.

2. The method of claim 1 wherein the wound is a burn or a surface wound.

3. The method of claim 1, wherein the subject is a mammal.

4. The method of claim 3, wherein the mammal is selected from the group consisting of a mouse, rat, guinea pig, rabbit, goat, dog, cat, horse, sheep, monkey and human.

5. The method of claim 1, wherein the stem/progenitor cells or the cellular extract thereof are administered systemically or topically.

6. The method of claim 5, wherein the stem/progenitor cells or the cellular extract thereof are administered in a topical formulation selected from the group consisting of an ointment, a cream, and a lotion.

* * * * *